United States Patent
Hammock et al.

(10) Patent No.: US 10,377,744 B2
(45) Date of Patent: Aug. 13, 2019

(54) POTENT SOLUBLE EPDXIDE HYDROLASE INHIBITORS

(71) Applicant: Eicosis, LLC, Davis, CA (US)

(72) Inventors: Bruce D. Hammock, Davis, CA (US); Kin Sing Stephen Lee, Davis, CA (US); Ahmet Bora Inceoglu, Davis, CA (US)

(73) Assignee: Eicosis, LLC, Davis, CA (US)

( * ) Notice: Subject to any disclaimer, the term of this patent is extended or adjusted under 35 U.S.C. 154(b) by 0 days.

(21) Appl. No.: 15/128,933

(22) PCT Filed: Mar. 27, 2015

(86) PCT No.: PCT/US2015/023048
§ 371 (c)(1),
(2) Date: Sep. 23, 2016

(87) PCT Pub. No.: WO2015/148954
PCT Pub. Date: Oct. 1, 2015

(65) Prior Publication Data
US 2017/0174665 A1    Jun. 22, 2017

Related U.S. Application Data

(60) Provisional application No. 61/971,410, filed on Mar. 27, 2014.

(51) Int. Cl.
*C07D 211/58* (2006.01)
*C07D 405/06* (2006.01)
*C07D 401/06* (2006.01)

(52) U.S. Cl.
CPC .......... *C07D 405/06* (2013.01); *C07D 211/58* (2013.01); *C07D 401/06* (2013.01)

(58) Field of Classification Search
CPC .................................................. C07D 211/58
See application file for complete search history.

(56) References Cited

U.S. PATENT DOCUMENTS

| 9,296,693 B2 | 3/2016 | Hammock et al. |
| 2008/0175914 A1 | 7/2008 | Allen et al. |
| 2013/0143925 A1* | 6/2013 | Hammock ........... A61K 31/445 514/329 |

FOREIGN PATENT DOCUMENTS

| WO | WO-2008051873 A2 * | 5/2008 | ........... C07D 211/58 |
| WO | WO-2012054093 A2 * | 4/2012 | ........... A61K 31/445 |
| WO | WO 2013/116690 A1 | 8/2013 | |
| WO | WO-2013116713 A1 * | 8/2013 | ......... A61K 31/4468 |
| WO | WO 2013/138118 A1 | 9/2013 | |
| WO | WO 2014/008992 A1 | 1/2014 | |

OTHER PUBLICATIONS

Ulu, A. "Pharmacokinetics and in vivo potency of soluble epoxide hydrolase inhibitors in cynomolgus monkeys." British Journal of Pharmacology. (2012), vol. 165, pp. 1401-1412.*
Enceoglu et al., "Epoxy Fatty Acids and Inhibition of the Soluble Epoxide Hydrolase Selectively Modulate GABA Mediated Neurotransmission to Delay Onset of Seizures," *PLOS ONE* (2013), 8(12), e80922:1-10.
Extended European Search Report dated Jul. 27, 2017, regarding EP 15 75 8180.
Rose, Tristan E. et al.: "*1-Aryl-3-(1-acylpiperidin-4-yl)urea inhibitors of Human and Murine Soluble Epoxide Hydrolase: Structure-Activity Relationships, Pharmaco-kinetics, and Reduction of Inflammatory Pain*"; Journal of Medicinal Chemistry, vol. 53, No. 19, (2010), pp. 7067-7075. Supporting Information, pp. S1-S39.

* cited by examiner

*Primary Examiner* — Noble E Jarrell
*Assistant Examiner* — John S Kenyon
(74) *Attorney, Agent, or Firm* — DLA Piper LLP (US)

(57) ABSTRACT

The invention discloses a new series of inhibitors of soluble epoxide hydrolase (sEH) with improved physical properties that enhance their druglikeness to treat sEH associated diseases such as chronic diabetic neuropathic pain.

2 Claims, 8 Drawing Sheets

POTENT SOLUBLE EPDXIDE HYDROLASE INHIBITORS

CROSS-REFERENCE TO RELATED APPLICATIONS

This application is a 35 USC § 371 National Stage application of International Application No. PCT/US2015/023048 filed Mar. 27, 2015, now expired; which claims the benefit under 35 USC § 119(e) to U.S. Application Ser. No. 61/971,410 filed Mar. 27, 2014. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. R43ES025598 awarded by the National Institutes of Health. The government has certain rights in the invention.

BACKGROUND OF THE INVENTION

Field of Invention

The present invention relates generally to chemical compounds, and more specifically to compounds that inhibit soluble epoxide hydrolase (sEH) well as methods of making and using the compounds.

Background Information

Soluble epoxide hydrolase (sEH, EC 3.3.2.10) is a bifunctional enzyme that in mammals is encoded by the Ephx2 gene. sEH found in cytosol and cytosolic peroxisomal fractions, hydrolyzes specific epoxides including epoxy fatty acids, to corresponding 1,2-diols while a different region of the protein also has a lipid phosphate phosphatase activity.

Epoxy fatty acids (EpFAs), metabolites from the cytochrome P450 (CYP450) pathway in the arachidonic acid cascade are important lipid mediators. Epoxyeicosatrienoic acids (EETs), epoxyeicosatetraenoic acids and epoxydocosapentaenoic acids, which are epoxide metabolites of arachidonic acid, eicosapentaenoic acid and docosahexaenoic acid respectively from CYP450 pathway, have been proven to be anti-inflammatory, vasoregulatory, analgesic and angiogenic.

EpFAs are majorly predominantly metabolized by the sEH to their corresponding 1,2-diols which diminishes their activities. Therefore, stabilization of EETs in vivo through inhibition of sEH can be anti-inflammatory, anti-hypertensive and analgesic through stabilization of EETs in vivo. Thus, the sEH is an important pharmaceutical target.

Most of diabetic patients will ultimately develop renal failure, hypertension and/or stroke. In addition, about 65% of diabetic patients will develop peripheral neuropathy. In addition to many other co-morbidities, people suffering from diabetic neuropathic pain experience spontaneous pain, hyperalgesia and allodynia which greatly affect the patients' quality of life. It has been suggested that hyperglycemia is the initiating cause of peripheral nerve fiber degeneration which results in pain. However, aggressive glycemic control can only control the progress of neuron degeneration but not reverse the neuropathy. Although semi-effective treatments of diabetic neuropathy are available which include tricyclic antidepressants and selective serotonin reuptake inhibitors, they have side effects that limit their use. Therefore, an alternative therapy with no or greatly reduced side effects is needed.

Recent studies indicate that soluble epoxide hydrolase (sEH) inhibitors are analgesic in diabetic neuropathic pain models. It was demonstrated that the sEH inhibitors are more potent, efficacious, and with fewer side effects than the clinically approved drug gabapentin.

Over the years, several groups reported the syntheses and the evaluation of sEH inhibitors having different central pharmacophores including but not limited to amides, carbamate and ureas with potency varying from micromolar to nanomolar ranges. The di-substituted urea is one of the potent central pharmacophores being used to inhibit sEH because the urea nitrogens make tight hydrogen bonding with the active residue Asp337 and the chemistry is easily accessible.

The physical properties of many of the most potent compounds are generally poor. Efforts to improve physical properties including water solubility, hydrophilicity, decrease clogP and lower melting point have generally resulted in a decrease in potency and less desirable pharmacokinetics. This can also result in poor absorption, inferior pharmacokinetic properties and can demand heroic formulation. Therefore, it is necessary to further optimize the structures to improve their physical properties which can ease the drug formulation processes and improve the oral bioavailability of the sEH inhibitors carrying a di-substituted ureas as a central pharmacophores.

Evidence is strong that residence time (t1/2) of the inhibitor on the target enzyme is one of the most important parameters affecting in vivo efficacy. Inhibitors with long residence time have long duration of action on the enzyme target which translates to long in vivo efficacy. However, most of the sEH inhibitors reported to date do not have optimum residence time on the enzyme. The sEH inhibitors with methyl at $R_7$ of Formula (II) below have short t1/2 and this could explain their lack of efficacy in man. Therefore, sEH inhibitors with longer residence time (t1/2) are essential to engage this pharmaceutical target.

SUMMARY OF THE INVENTION

In one aspect, the present invention provides compounds of structural Formula (I), or an optically pure stereoisomer or pharmaceutically acceptable salt thereof.

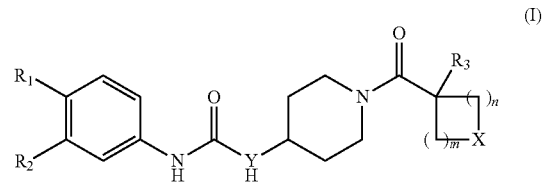

wherein:
$R_1$ is selected from the group consisting of trifluoromethyl- or trifluoromethoxy-;
$R_2$ is selected from the group consisting of H— or F—;
$R_3$ is selected from the group consisting of H—, trifluoromethyl- or —$CH_2CO_2H$;
X is selected from carbon, nitrogen or oxygen;
Y is selected from carbon, nitrogen or oxygen;
subscript m is 0, 1 or 2; and
subscript n is 1 or 2.

In another aspect, the present invention provides compounds of structural Formula (II), or an optically pure stereoisomer or pharmaceutically acceptable salt thereof.

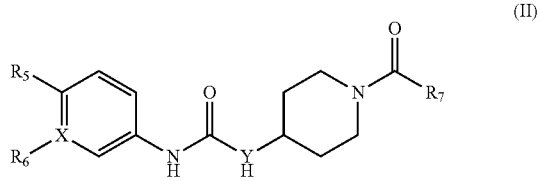

wherein:

X is selected from carbon or nitrogen;

Y is selected from carbon, nitrogen or oxygen;

$R_5$ is selected from the group consisting of trifluoromethyl- or trifluoromethoxy-;

$R_6$ is selected from the group consisting of H— or F—; and $R_7$ is selected from the group consisting of 1H-pyrrole, furan, pyran, tetrahydropyran, 4,5-dihydrofuran, 2-methylfuran, 3-methylfuran, ethyl-, isopropyl-, cyclopropyl-, 2-methylbutyl- and (S)-2-methylbutyl-group.

The compounds include all pharmaceutically acceptable derivatives thereof, such as salts, prodrugs, soft drugs, solvates and hydrates.

Certain embodiments also provide pharmaceutical compositions comprising one or more compounds disclosed herein together with a pharmaceutically acceptable carrier, as well as methods of making and using the compounds and compositions.

In another aspect, the present invention provides a method for inhibiting a soluble epoxide hydrolase, comprising contacting the soluble epoxide hydrolase with an inhibiting amount of a compound having the Formula (I) or (II), above.

In a related aspect, the present invention provides methods of treating diseases modulated by soluble epoxide hydrolases, the method comprising administering to a subject in need of such treatment an effective amount of a compound having a formula selected from Formula (I) or (II), above. In one aspect, the effective amount is a therapeutically effective amount.

In another aspect, the present invention provides a method for increasing the water solubility of a compound of Formula (I) by incorporating a heteroatom at X.

In a related aspect, the present invention provides a method for increasing the water solubility of a compound of Formula (II) by incorporating a heterocycle at $R_7$.

In another aspect, the present invention provides a method for decreasing the melting point of a compound of Formula (I) by incorporating fluorine at $R_2$.

In a related aspect, the present invention provides a method for decreasing the melting point of a compound of Formula (II) by incorporating fluorine at $R_6$.

In another aspect, the present invention provides a method for increasing water solubility of a compound of Formula (I) in the range of pH 1-7, by incorporating oxygen at X and subscript m is 0, 1 or 2 and n is 1 or 2.

In a related aspect, the present invention provides a method for increasing water solubility of a compound of Formula (II) in the range of pH 1-7, by incorporating a heterocycle at $R_7$.

In another aspect, the present invention provides a method for increasing the residence time (t1/2) on soluble epoxide hydrolase of a compound of Formula (I) by incorporating trifluoromethoxy- group at $R_1$.

In a related aspect, the present invention provides a method for increasing residence time (t1/2) on soluble epoxide hydrolase of a compound of Formula (II) by incorporating trifluoromethoxy- group at $R_5$ and isopropyl-, cyclopropyl-, 2-methylbutyl- or (S)-2-methylbutyl- group at $R_7$.

In another aspect, the present invention provides a method for monitoring the activity of a soluble epoxide hydrolase (sEH). The method includes contacting the soluble epoxide hydrolase with an amount of a compound of Formula (I) or (II) sufficient to produce a detectable change in optical fluorescence of the soluble epoxide hydrolase by interaction with one or more tryptophan residues present in a catalytic site of the sEH.

In another aspect, the present invention provides a method for treating a disease or disorder in a subject. The method includes administering to the subject in need of such treatment an effective amount of a compound having a formula selected from Formula (I) or (II), above. In embodiments the disease or disorder is pain, such as diabetic neuropathic pain, inflammatory pain or post-surgical pain. In some embodiments, the neuropathic pain may be the result of nerve injury as a result of diabetes, either congenital or otherwise, or other types of nervous system disorders such injury resulting from external forces such as an accident, surgery or disease state including infection, or a drug used for the treatment of another ailment. In related embodiments, the disease is an epileptic disorder.

DETAILED DESCRIPTION OF THE INVENTION

Abbreviations and Definitions

Figure 1:
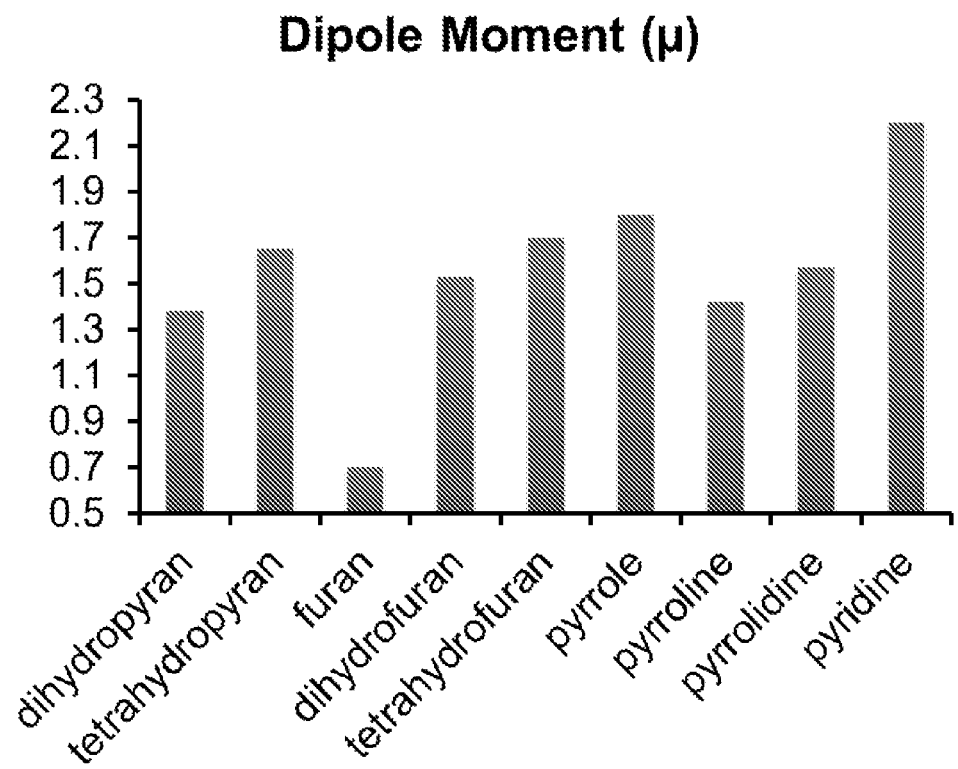
FIG. 1 is a graph showing that the dipole moment relationship of different heterocycles attached at $R_7$ of Formula (II) and it does not correlate with the enhanced solubility that was achieved as shown in Table II.

"Epoxide hydrolases" ("EH;" EC 3.3.2.3) are enzymes in the alpha/beta-hydrolase fold family that add water to 3 membered cyclic ethers termed epoxides.

"Soluble epoxide hydrolase" ("sEH") is an enzyme which in endothelial, smooth muscle and other cell types converts EETs to dihydroxy derivatives called dihydroxyeicosatrienoic acids ("DHETs"). The cloning and sequence of the murine sEH is set forth in Grant et al., *J. Biol. Chem.* 268(23):17628-17633 (1993). The cloning, sequence, and accession numbers of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO: 1 of that patent. The evolution and nomenclature of the gene is discussed in Beetham et al., *DNA Cell Biol.* 14(1):61-71 (1995). Soluble epoxide hydrolase represents a single highly conserved gene product with over 90% homology between rodent and human (Arand et al., *FEBS Lett.,* 338:251-256 (1994)).

The terms "treat", "treating" and "treatment" refer to any method of alleviating or abrogating a disease or its attendant symptoms.

The term "therapeutically effective amount" refers to that amount of the compound being administered sufficient to prevent or decrease the development of one or more of the symptoms of the disease, condition or disorder being treated.

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

The term "compound" as used herein is intended to encompass not only the specified molecular entity but also its pharmaceutically acceptable, pharmacologically active derivatives, including, but not limited to, salts, prodrug conjugates such as esters and amides, metabolites and the like.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "sEH mediated disorder or disease" and the like refers to a disease or condition characterized by less than or greater than normal, sEH activity. A she mediated disorder or disease is one in which modulation of sEH results in some effect on the underlying condition or disease (e.g., a sEH inhibitor or antagonist results in some improvement in patient well-being in at least some patients). Such disorders and diseases may include seizure disorders, such as epilepsy, nephropathy, cardiomyopathy, hypertension, pain, inflammation, inflammatory pain, post-surgical pain, neuropathic pain, diabetic neuropathic pain, tissue wounds or pain therefrom, acute inflammation, inflammation from sepsis, pancreatitis, multiple trauma such as injury to the brain, and tissue injury, such as laceration of the musculature, brain surgery, hemorrhagic shock, and immune-mediated organ injuries, adult respiratory distress syndrome, emphysema, chronic bronchitis, obstructive pulmonary disease, chronic obstructive pulmonary disease (COPC), small airway disease, interstitial lung disease (ILD), idiopathic pulmonary fibrosis, burning or pain in dermatoses such as dermatitis, chemical burns, thermal burns, reddening of the skin, and chemically induced lesions, neuralgia, pain caused by trauma or irritation to peripheral nerves near the surface of the skin.

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "aralkyl," "alkylamino" and similar terms. In some embodiments, alkyl groups are those containing 1 to 24 carbon atoms. All numerical ranges in this specification and claims are intended to be inclusive of their upper and lower limits. Lower alkyl refers to those alkyl groups having 1 to 4 carbon atoms. Additionally, the alkyl and heteroalkyl groups may be attached to other moieties at any position on the alkyl or heteroalkyl radical which would otherwise be occupied by a hydrogen atom (such as, for example, 2-pentyl, 2-methylpent-1-yl and 2-propyloxy). Divalent alkyl groups may be referred to as "alkylene", and divalent heteroalkyl groups may be referred to as "heteroalkylene" such as those groups used as linkers in the present invention. The alkyl, alkylene, and heteroalkyl moieties may also be optionally substituted with halogen atoms, or other groups such as oxo, cyano, nitro, alkyl, alkylamino, carboxyl, hydroxyl, alkoxy, aryloxy, and the like.

The terms "cycloalkyl" and "cycloalkenyl" refer to a saturated hydrocarbon ring and includes bicyclic and polycyclic rings. Similarly, cycloalkyl and cycloalkenyl groups having a heteroatom (e.g., N, O or S) in place of a carbon ring atom may be referred to as "heterocycloalkyl" and heterocycloalkylene," respectively. Examples of cycloalkyl and heteroaryl groups are, for example, cyclohexyl, norbornyl, adamantly, morpholinyl, thiomorpholinyl, dioxothiomorpholinyl, and the like. The cycloalkyl and heterocycloalkyl moieties may also be optionally substituted with halogen atoms, or other groups such as nitro, alkyl, alkylamino, carboxyl, alkoxy, aryloxy and the like. In some embodiments, cycloalkyl and cycloalkenyl moieties are those having 3 to 12 carbon atoms in the ring (e.g., cyclohexyl, cyclooctyl, norbornyl, adamantyl, and the like). In some embodiments, heterocycloalkyl and heterocycloalkylene moieties are those having 1 to 3 hetero atoms in the ring (e.g., morpholinyl, thiomorpholinyl, dioxothiomorpholinyl, piperidinyl and the like). Additionally, the term "(cycloalkyl)alkyl" refers to a group having a cycloalkyl moiety attached to an alkyl moiety. Examples are cyclohexylmethyl, cyclohexylethyl and cyclopentylpropyl.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy, aryloxy and t-butoxy).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g., N, O or S) in place of a carbon ring atom are referred to as "heteroaryl". Examples of aryl and heteroaryl groups are, for example, phenyl, naphthyl, biphenyl, diphenylmethyl, 2,2-diphenyl-1-ethyl, thienyl, pyridyl and quinoxalyl. The aryl and heteroaryl moieties may also be optionally substituted with halogen atoms, or other groups such as nitro, alkyl, alkylamino, carboxyl, alkoxy, phenoxy and the like. Additionally, the aryl and heteroaryl groups may be attached to other moieties at any position on the aryl or heteroaryl radical which would otherwise be occupied by a hydrogen atom (such as, for example, 2-pyridyl, 3-pyridyl and 4-pyridyl). Divalent aryl groups are "arylene", and divalent heteroaryl groups are referred to as "heteroarylene" such as those groups used as linkers in the present invention.

The terms "arylalkyl", "arylalkenyl" and "aryloxyalkyl" refer to an aryl radical attached directly to an alkyl group, an alkenyl group, or an oxygen which is attached to an alkyl group, respectively. For brevity, aryl as part of a combined term as above, is meant to include heteroaryl as well.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_1$-$C_6$ haloalkyl" is mean to include trifluoromethyl, 2,2,2-trifluoroethyl, 4-chlorobutyl, 3-bromopropyl, and the like.

The term "hetero" as used in a "heteroatom-containing alkyl group" (a "heteroalkyl" group) or a "heteroatom-containing aryl group" (a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur or more that none non-carbon atom (e.g., sulfonamide). Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrophobic radical" or "hydrophobic group" refers to a group which lowers the water solubility of a molecule. In some embodiments, hydrophobic radicals are groups containing at least 3 carbon atoms.

The term "hetero" as used in a "heteroatom" refers to any atom other than carbon or hydrogen, e.g., nitrogen, oxygen, sulfur, phosphorus or silicon.

The term "carboxylic acid analog" refers to a variety of groups having an acidic moiety that are capable of mimicking a carboxylic acid residue. Examples of such groups are sulfonic acids, sulfinic acids, phosphoric acids, phosphonic acids, phosphinic acids, sulfonamides, and heterocyclic moieties such as, for example, imidazoles, triazoles and tetrazoles.

The term "substituted" refers to the replacement of an atom or a group of atoms of a compound with another atom or group of atoms. For example, an atom or a group of atoms may be substituted with one or more of the following substituents or groups: halo, cyano, nitro, alkyl, alkylamino, hydroxyalkyl, haloalkyl, carboxyl, hydroxyl, alkoxy, alkoxyalkoxy, haloalkoxy, thioalkyl, aryl, aryloxy, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

General

Over the last decades, the 1,3-disubstituted urea has been one of the potent central pharmacophores for soluble epoxide hydrolase (sEH). However, sEH inhibitors with 1,3-disubstituted urea always suffer from poor solubility with high melting point, which make them difficult to formulate and less druglikeness.

Solubility and melting point are important parameters that affect druglikeness and the ease of formulation is greatly affected by these two parameters. However, these two parameters are difficult to predict and modify. In addition, modification of these two parameters in the past had a generally negative effect on the potency of the inhibitors.

Inhibitors with flexible substituents on one end of 1,3-disubstituted urea have lower melting points which facilitate the drug formulation process. However, such inhibitors generally, are metabolically unstable with poor oral bioavailability. Therefore, inhibitors with restricted or rigid substituents were synthesized but they suffered with much higher melting point (>180° C.) which makes them poor drug candidates and there are no reports of any specific modifications that decreases the melting point of the sEH inhibitors.

The binding pocket of sEH is very hydrophobic. Therefore, sEH inhibitors with very good potency at nM level always carry hydrophobic substituents on both ends of the 1,3-disubstituted urea. These substituents always lead to inhibitors with very poor water solubility over a wide range of pH. These properties result in difficulty a lot of problem in drug formulation and always result in poor bioavailability.

In order to enhance solubility of the sEH inhibitors, polar substituents were incorporated to the sEH inhibitors. However, such incorporation often results of a decrease of potency against sEH.

Residence time (t1/2) has been suggested to play an important role of in vivo efficacy but there is no report on increasing the residence time of sEH inhibitors. sEH inhibitors with short alky chain has been reported to have short t1/2 which can explain their lack of in vivo efficacy in human clinical trials.

Inhibitors that can penetrate blood brain barrier are important to treat neurological diseases. However, it is hard to identify that the compounds can cross blood-brain barrier as well as compounds that are peripherally restricted because they cannot penetrate the blood brain barrier.

The present invention derives from the discovery that certain sEH inhibitors may be further functionalized to provide more potent sEH inhibitors with improved physical properties.

As described herein, the introduction of heterocycles into the inhibitors increases water solubility and oral availability of sEH inhibitors. Further modifications were determined to decrease melting point and significantly increase potency on the target.

Compounds

In one aspect, the present invention provides compounds of structural Formula (I), or an optically pure stereoisomer or pharmaceutically acceptable salt thereof.

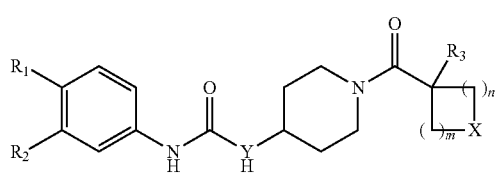

(I)

wherein:
$R_1$ is selected from the group consisting of trifluoromethyl- or trifluoromethoxy-;
$R_2$ is selected from the group consisting of H— or F—;
$R_3$ is selected from the group consisting of H—, trifluoromethyl- or —CH$_2$CO$_2$H;
X is selected from carbon, nitrogen or oxygen;
Y is selected from carbon, nitrogen or oxygen;
subscript m is 0, 1 or 2; and
subscript n is 1 or 2.

In another aspect, the present invention provides compounds of structural Formula (II), or an optically pure stereoisomer or pharmaceutically acceptable salt thereof.

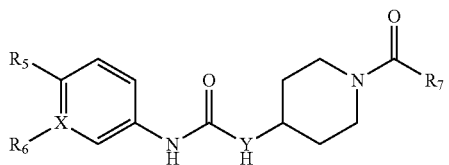

(II)

wherein:
X is selected from carbon or nitrogen;
Y is selected from carbon, nitrogen or oxygen;
$R_5$ is selected from the group consisting of trifluoromethyl- or trifluoromethoxy-;
$R_6$ is selected from the group consisting of H— or F—; and
$R_7$ is selected from the group consisting of 1H-pyrrole, furan, pyran, tetrahydropyran, 4,5-dihydrofuran, 2-methylfuran, 3-methylfuran, ethyl-, isopropyl-, cyclopropyl-, 2-methylbutyl- and (S)-2-methylbutyl- group.

The compounds include all pharmaceutically acceptable derivatives thereof, such as salts, prodrugs, soft drugs, solvates and hydrates.

Representative compounds of the present invention are presented in Table I below.

TABLE I sEH Inhibitors (physical properties and potency against human sEH)

| Structure and Compound No. | Mol. Weight | Exp. logP[a] | Cal. logP[b] | Ki (nM) human sEH[c] | $t_{1/2}$ (min) human sEH[d] |
|---|---|---|---|---|---|
| Compound 1 | 415.11 | 3.26 | 0.6 | 1.43 ± 0.01 | 14 |
| Compound 2 | 396.14 | 3.34 | 1.8 | 0.64 ± 0.17 | 15 |
| Compound 3 | 397.12 | 3.63 | 2.0 | 0.33 ± 0.34 | 17 |

TABLE I-continued
sEH Inhibitors (physical properties and potency against human sEH)
| Structure and Compound No. | Mol. Weight | Exp. logP[a] | Cal. logP[b] | Ki (nM) human sEH[c] | $t_{1/2}$ (min) human sEH[d] |
|---|---|---|---|---|---|
| 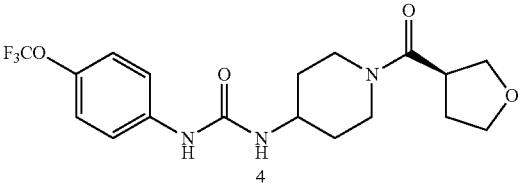 4 | 401.16 | 3.38 | 1.4 | 1.41 ± 0.11 | 17 |
| 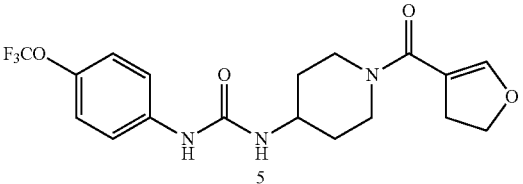 5 | 399.14 | 3.49 | 2.6 | 0.77 ± 0.02 | 13 |
| 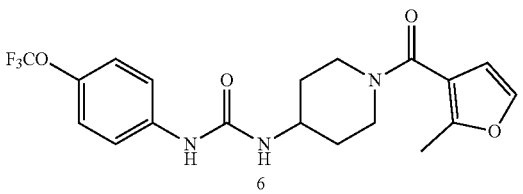 6 | 411.14 | 4.30 | 2.5 | 0.55 ± 0.06 | 15 |
| 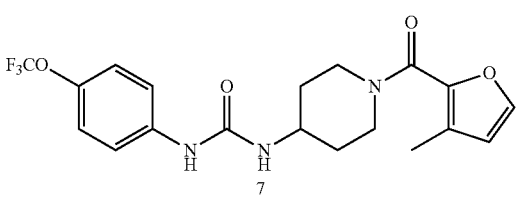 7 | 411.14 | 4.48 | 2.5 | 0.26 ± 0.11 | 21 |
| 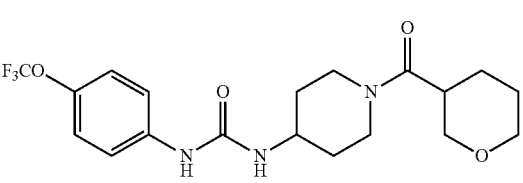 [SMILES: O=C(Nc1ccc(OC(F)(F)F)cc1)NC1CCN(C(=O)C2CCCOC2)CC1] 8 | 415.17 | 3.42 | 1.8 | 1.99 ± 0.23 | 13 |
| 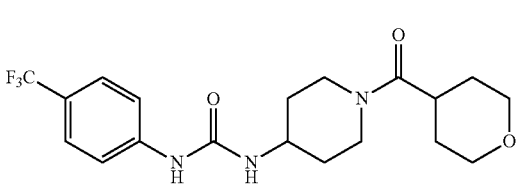 [SMILES: O=C(Nc1ccc(C(F)(F)F)cc1)NC1CCN(C(=O)C2CCOCC2)CC1] 9 | 399.18 | 3.16 | 0.8 | 1.73 ± 0.01 | 11 |
| 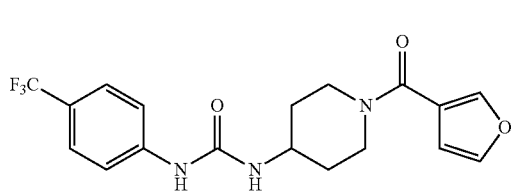 [SMILES: O=C(Nc1ccc(C(F)(F)F)cc1)NC1CCN(C(=O)c2ccoc2)CC1] 10 | 381.13 | 3.50 | 1.6 | 1.21 ± 0.2 | 11 |

TABLE I-continued
sEH Inhibitors (physical properties and potency against human sEH)
| Structure and Compound No. | Mol. Weight | Exp. logP[a] | Cal. logP[b] | Ki (nM) human sEH)[c] | t$_{1/2}$ (min) human sEH)[d] |
|---|---|---|---|---|---|
| 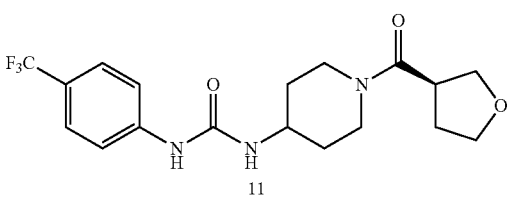 11 | 385.16 | 3.27 | 2.2 | 1.19 ± 0.08 | 13 |
| 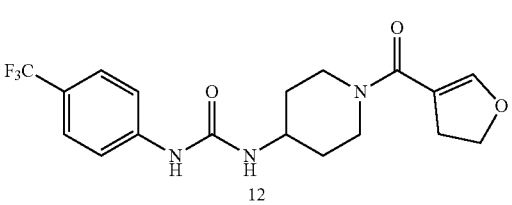 12 | 383.15 | 3.37 | 2.8 | 1.03 ± 0.20 | 8 |
| 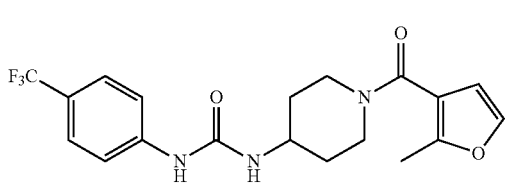 [SMILES: Cc1occc1C(=O)N1CCC(NC(=O)Nc2ccc(C(F)(F)F)cc2)CC1] 13 | 395.15 | 4.19 | 2.7 | 0.51 ± 0.03 | 11 |
| 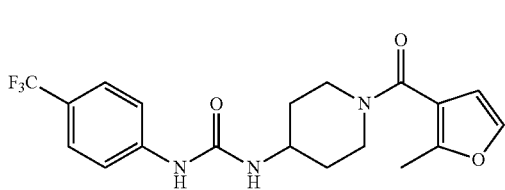 [SMILES: Cc1occc1C(=O)N1CCC(NC(=O)Nc2ccc(C(F)(F)F)cc2)CC1] 14 | 395.15 | 4.29 | 2.7 | 0.22 ± 0.01 | 15 |
| 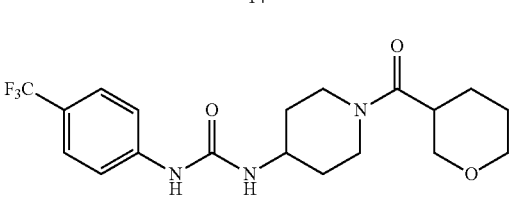 15 | 399.18 | 3.41 | 2.0 | 2.40 ± 0.08 | 11 |
| 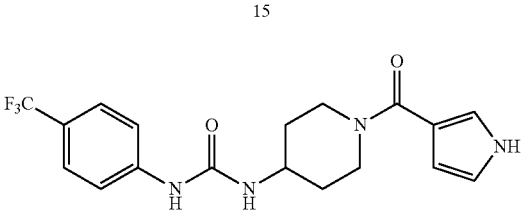 16 | 380.15 | 3.26 | 2.0 | 0.50 ± 0.01 | 10 |
| 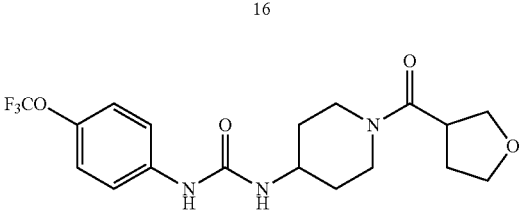 17 | 401.16 | 3.22 | 1.4 | 1.70 ± 0.01 | 12 |

TABLE I-continued
sEH Inhibitors (physical properties and potency against human sEH)
| Structure and Compound No. | Mol. Weight | Exp. logP[a] | Cal. logP[b] | Ki (nM) human sEH[c] | $t_{1/2}$ (min) human sEH[d] |
|---|---|---|---|---|---|
| 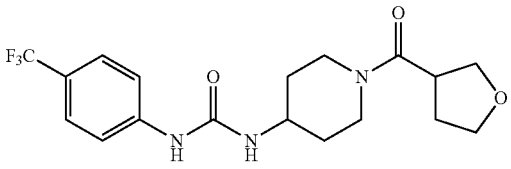 [SMILES: O=C(Nc1ccc(C(F)(F)F)cc1)NC1CCN(C(=O)C2CCOC2)CC1] 18 | 385.16 | 3.16 | 1.6 | 1.74 ± 0.11 | 10 |
| 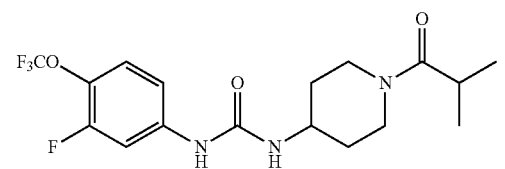 [SMILES: CC(C)C(=O)N1CCC(NC(=O)Nc2ccc(OC(F)(F)F)c(F)c2)CC1] 19 | 391.15 | 4.73 | 2.0 | 0.31 ± 0.01 | 22 |
| 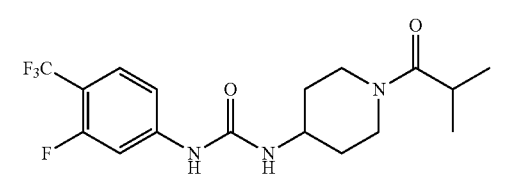 [SMILES: CC(C)C(=O)N1CCC(NC(=O)Nc2ccc(C(F)(F)F)c(F)c2)CC1] 20 | 375.16 | 4.40 | 2.3 | 0.49 ± 0.4 | 12 |
| 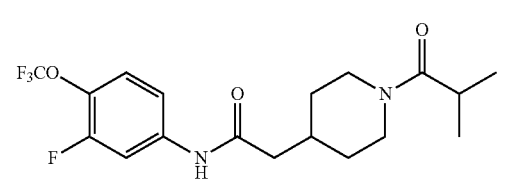 [SMILES: CC(C)C(=O)N1CCC(CC(=O)Nc2ccc(OC(F)(F)F)c(F)c2)CC1] 21 | 390.38 | 5.18 | 2.6 | 4.72 ± 0.70 | 3.4 |
| 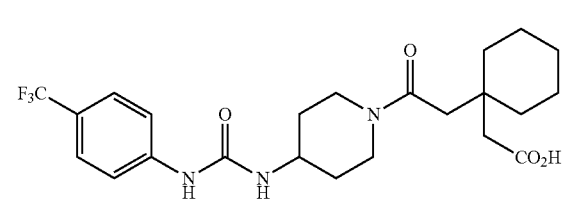 [SMILES: O=C(O)CC1(CC(=O)N2CCC(NC(=O)Nc3ccc(C(F)(F)F)cc3)CC2)CCCCC1] 22 | 469.22 | — | — | 10.2 ± 1.1 | — |
| 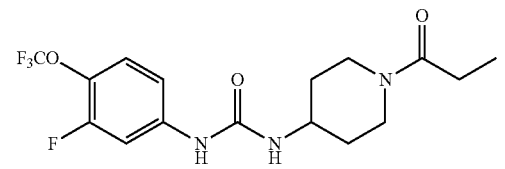 [SMILES: CCC(=O)N1CCC(NC(=O)Nc2ccc(OC(F)(F)F)c(F)c2)CC1] 23 | 377.34 | 4.00 | 1.7 | 0.87 ± 0.13 | 11 |
| 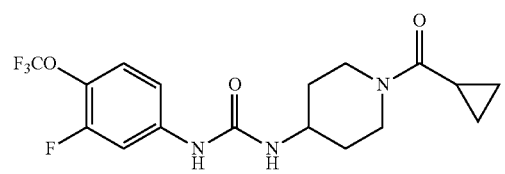 [SMILES: O=C(Nc1ccc(OC(F)(F)F)c(F)c1)NC1CCN(C(=O)C2CC2)CC1] 24 | 389.35 | 4.19 | 1.7 | 0.15 ± 0.04 | 19 |

TABLE I-continued
sEH Inhibitors (physical properties and potency against human sEH)
| Structure and Compound No. | Mol. Weight | Exp. logP[a] | Cal. logP[b] | Ki (nM) human sEH[c] | t$_{1/2}$ (min) human sEH[d] |
|---|---|---|---|---|---|
| 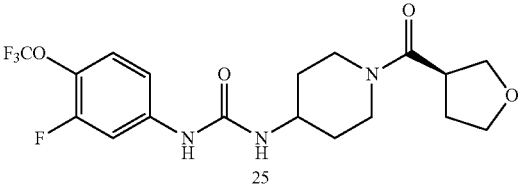 25 | 419.38 | 3.59 | 1.6 | 0.70 ± 0.01 | 13 |
| 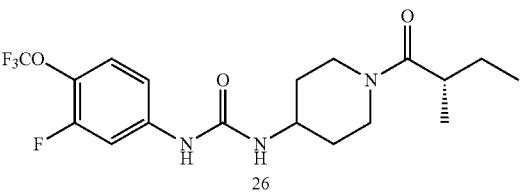 26 | 405.39 | 4.16 | 2.5 | <0.05 | 22 |
| 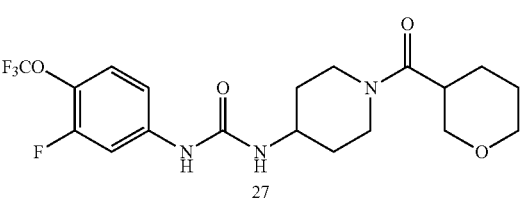 27 | 433.40 | 4.09 | 2.0 | 0.78 ± 0.19 | 12 |
| 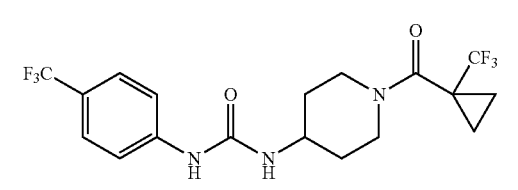 [SMILES: O=C(Nc1ccc(C(F)(F)F)cc1)NC1CCN(C(=O)C2(C(F)(F)F)CC2)CC1] 28 | 439.36 | 4.63 | 2.0 | 0.05 ± 0.04 | 24 |
| 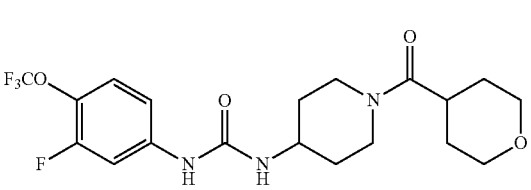 29 | 433.4 | 3.73 | 0.8 | 0.75 ± 0.05 | 11 |
| 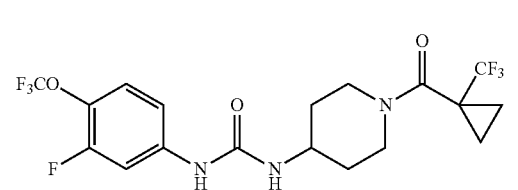 [SMILES: O=C(Nc1ccc(OC(F)(F)F)c(F)c1)NC1CCN(C(=O)C2(C(F)(F)F)CC2)CC1] 30 | 457.35 | 5.94 | 2.0 | <0.05 | 18 |
| 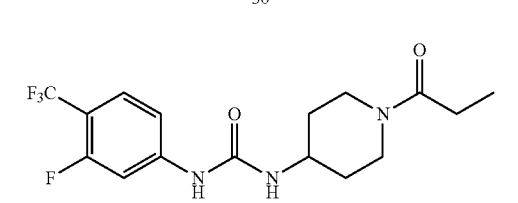 31 | 361.33 | 3.76 | 1.9 | 2.94 ± 0.01 | 3.3 |

TABLE I-continued
sEH Inhibitors (physical properties and potency against human sEH)
| Structure and Compound No. | Mol. Weight | Exp. logP$^a$ | Cal. logP$^b$ | Ki (nM) human sEH$^c$ | t$_{1/2}$ (min) human sEH$^d$ |
|---|---|---|---|---|---|
| 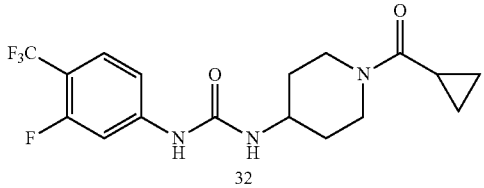 32 | 389.34 | 3.94 | 2.0 | 0.38 ± 0.08 | 8.2 |
| 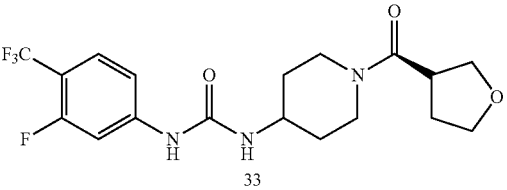 33 | 403.37 | 3.41 | 1.9 | 2.09 ± 0.24 | 5.3 |
| 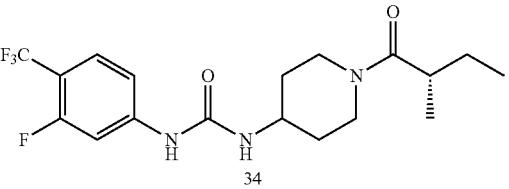 34 | 389.39 | 5.48 | 2.8 | 0.37 ± 0.03 | 13 |
| 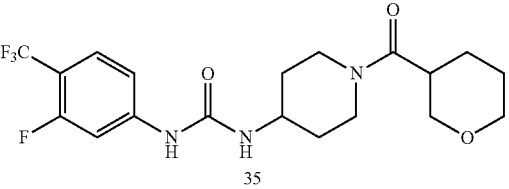 35 | 417.40 | 3.84 | 2.3 | 2.66 ± 0.19 | 6.8 |
| 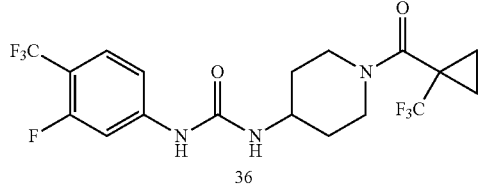 36 | 441.34 | 5.52 | 2.5 | 0.08 ± 0.01 | 21 |
| 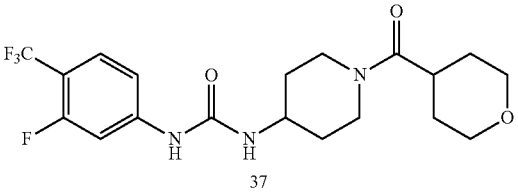 37 | 417.40 | 3.52 | 1.1 | 3.83 ± 0.41 | 6.9 |
| 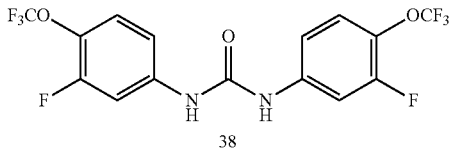 38 | 416.23 | ND | ND | 1.95 ± 0.30 | ND |

TABLE I-continued sEH Inhibitors (physical properties and potency against human sEH)

| Structure and Compound No. | Mol. Weight | Exp. logP[a] | Cal. logP[b] | Ki (nM) human sEH[c] | $t_{1/2}$ (min) human sEH[d] |
|---|---|---|---|---|---|
| 39 | 668.50 | ND | ND | 10.1 ± 1.8 | ND |
| 40 | 393.34 | 5.94 | 3.3 | <0.05 | 18 |
| 41 | 377.34 | 5.46 | 3.6 | 0.38 ± 0.03 | 7.6 |
| 42 | 372.39 | 3.22 | 1.7 | 45.0 ± 2.3 | 3.7 |
| 43 | 434.39 | 3.93 | 2.6 | 0.70 ± 0.06 | 15 |
| 44 | 421.85 | 7.70 | 3.0 | 3.35 ± 0.42 | 10 |
| 45 | 465.29 | 8.07 | 3.2 | 3.40 ± 1.38 | 9.3 |

TABLE I-continued
sEH Inhibitors (physical properties and potency against human sEH)
| Structure and Compound No. | Mol. Weight | Exp. logP[a] | Cal. logP[b] | Ki (nM) human sEH[c] | $t_{1/2}$ (min) human sEH[d] |
|---|---|---|---|---|---|
| 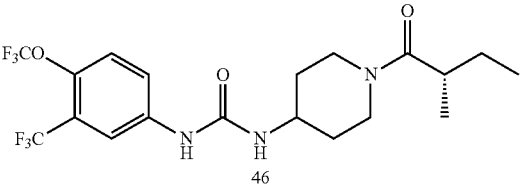 46 | 455.40 | 9.02 | 3.7 | 9.91 ± 3.37 | 5.9 |
| 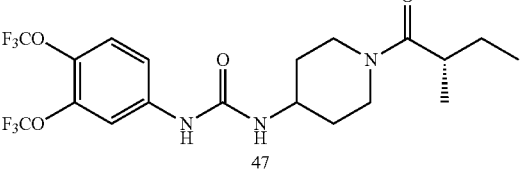 47 | 471.40 | 10.62 | 3.1 | 9.07 ± 0.36 | 11 |
| 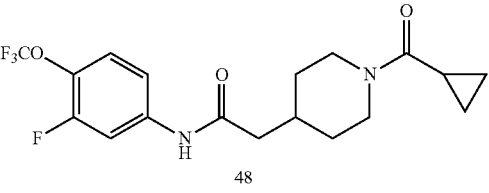 48 | 388.36 | 5.11 | 2.3 | 6.60 ± 0.01 | 3.3 |
| 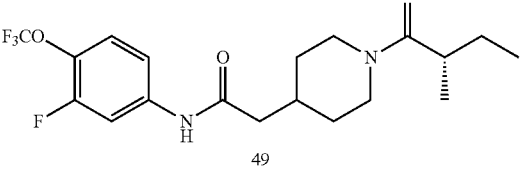 49 | 404.41 | 7.68 | 3.4 | 3.14 ± 0.70 | 4.5 |
| 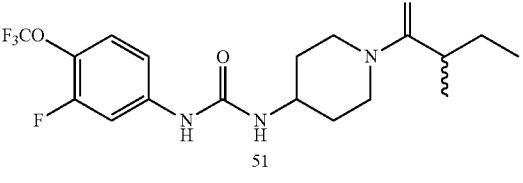 51 | 405.39 | ND | 2.5 | 0.06 ± 0.01 | ND |
| 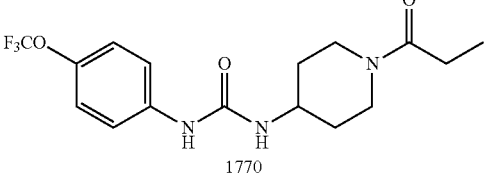 1770 | 359.34 | 3.23 | 1.50 | 0.91 ± 0.13 | 11 |
| 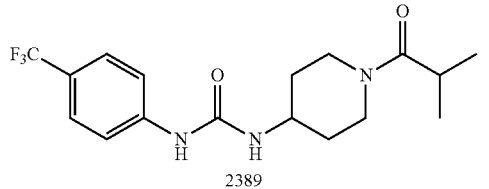 2389 | 357.37 | 3.37 | 2.00 | 0.66 ± 0.30 | 18 |

TABLE I-continued sEH Inhibitors (physical properties and potency against human sEH)

| Structure and Compound No. | Mol. Weight | Exp. logP[a] | Cal. logP[b] | Ki (nM) human sEH[c] | $t_{1/2}$ (min) human sEH[d] |
|---|---|---|---|---|---|
| 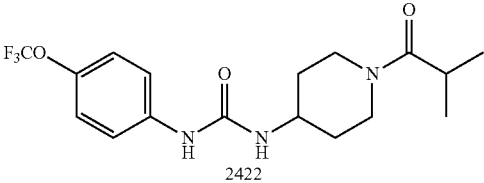 2422 | 373.37 | 3.56 | 1.81 | 0.31 ± 0.18 | 19 |
| 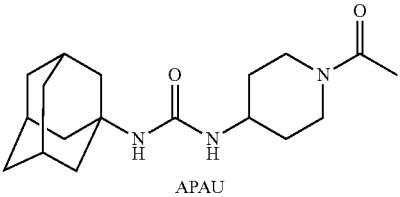 APAU | 319.44 | 1.5 | 0.8 | 19.5 ± 3.8 | 6 |

Abbreviation:
Mol. Weight: Molecular Weight;
Sol: Solubility;
$K_i$: Inhibition Constant with affinity purified recombinant human sEH;
elogP: Experimental log P;
clogP: Calculated log P;
—: Not Determined.
[a]elogP was determined by HPLC method calibrated with eLogP of 4 selected inhibitors determined by shake-flask method.
[b]cLogP was calculated by the CLogP Driver from Cambridge Soft CLogP available from ChemBioOffice 2012.
[c]The $K_i$ was measured by FRET-displacement assay published before (Lee et al. Anal. Chem. 2013. see Example 53)
[d]This enzymatic $t_{1/2}$ defined as the time required for half of the drug being dissociated from the recombinant affinity purified human sEH based on the fluorescence signals.

In exemplary embodiments, the present invention provides the following compounds from Table I: 1-(3-fluoro-4-(trifluoromethoxy)phenyl)-3-(1-isobutyrylpiperidin-4-yl) urea (Compound 19); 1-(1-(tetrahydro-2H-pyran-4-carbonyl)piperidin-4-yl)-3-(4-(trifluoromethoxy)phenyl) urea (Compound 1); 1-(1-(cyclopropanecarbonyl)piperidin-4-yl)-3-(3-fluoro-4-(trifluoromethoxy)phenyl)urea (Compound 24); (S)-1-(3-fluoro-4-(trifluoromethoxy)phenyl)-3-(1-(2-methylbutanoyl)piperidin-4-yl)urea (Compound 26); and 1-(3-fluoro-4-(trifluoromethoxy)phenyl)-3-(1-(tetrahydro-2H-pyran-4-carbonyl)piperidin-4-yl)urea (Compound 29).

Certain embodiments the present invention also provides pharmaceutical compositions comprising one or more compounds disclosed herein together with a pharmaceutically acceptable carrier, as well as methods of making and using the compounds and compositions.

Compound Preparation

The compounds of the present invention may be prepared by a variety of methods as outlined in the General Synthetic Scheme shown below which outlines three synthetic pathways, each of which is discussed in further detail in Example 1.

General Synthetic Scheme

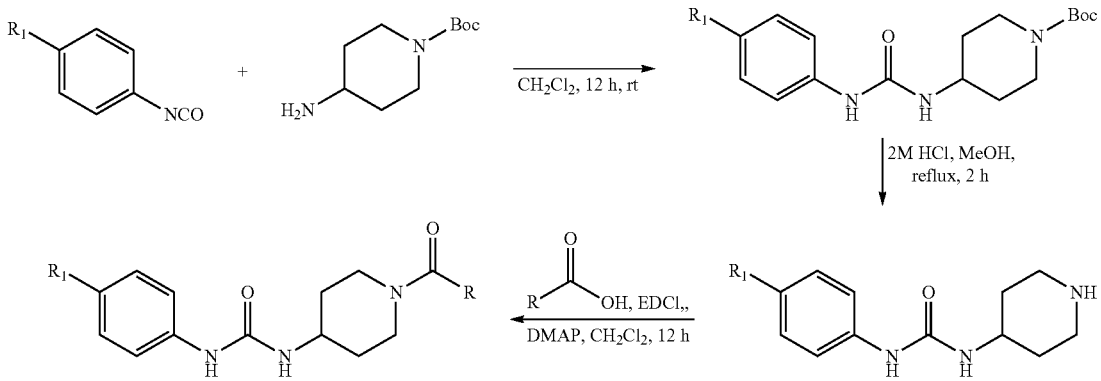

Synthetic Pathway 2

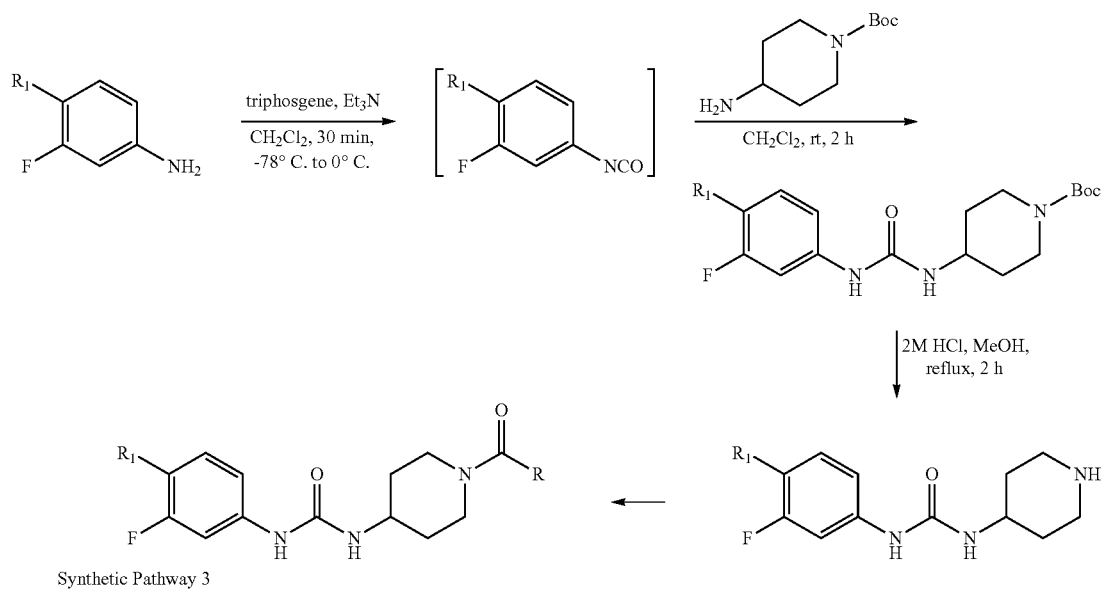

Synthetic Pathway 3

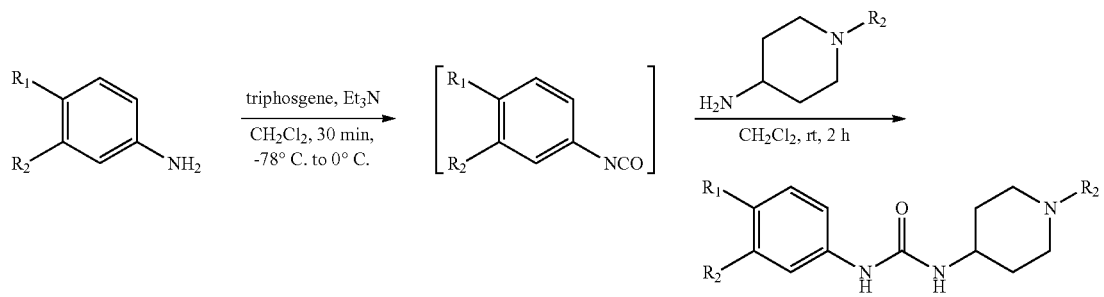

In order to enhance solubility, heterocycles were incorporated into the inhibitors (Formula II) at $R_7$. However, interestingly, most of the heterocycles were able to enhance the solubility of the inhibitors at pH 7.4 as compared to the sEH inhibitors of Formula (II) with hydrophobic alkyl group at $R_7$ as shown in Formula (II) (Table II and FIG. 3).

TABLE II

| Compound Solubility (at pH 7 and pH 3) | | |
|---|---|---|
| Structure | Solubility[a] (ug/mL) | Sol[b] (ug/mL) at pH3 |
| 1 | 91 | 1295 |
| 2 | 43 | 58 |

TABLE II-continued
Compound Solubility (at pH 7 and pH 3)
| Structure | Solubility$^a$ (ug/mL) | Sol$^b$ (ug/mL) at pH3 |
|---|---|---|
| 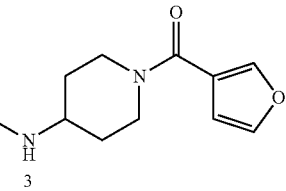 3 | 7.6 | 26 |
| 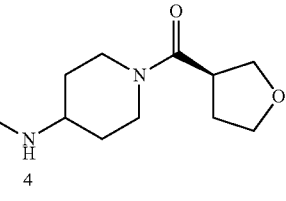 4 | 23 | 65 |
| 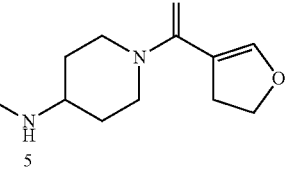 5 | 11 | 73 |
| 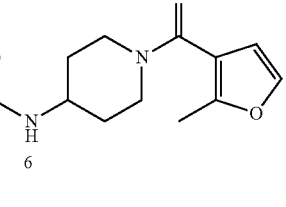 6 | 8.6 | 7.7 |
| 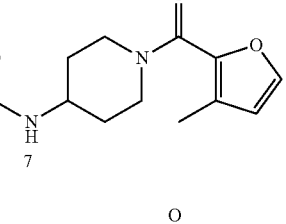 7 | 0.92 | 3.4 |
| 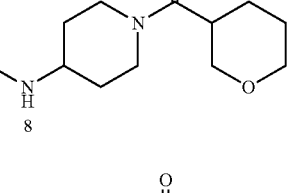 8 | 94 | 868 |
| 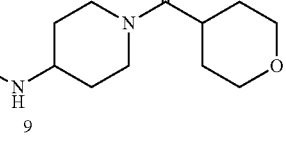 9 | 17.6 | 61 |

TABLE II-continued
Compound Solubility (at pH 7 and pH 3)
| Structure | Solubility[a] (ug/mL) | Sol[b] (ug/mL) at pH3 |
|---|---|---|
| 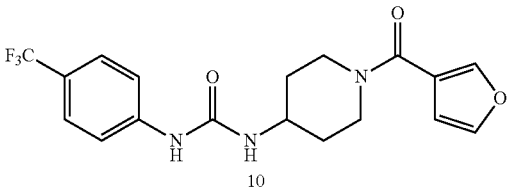 10 | 2.2 | 6 |
| 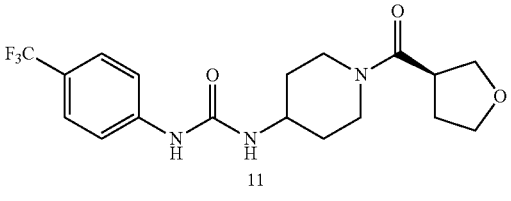 11 | 1.4 | 58 |
| 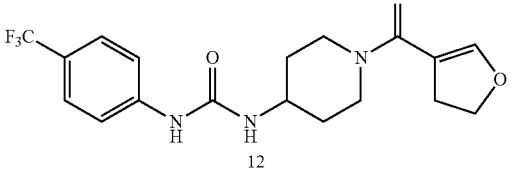 12 | 2.3 | 8.2 |
| 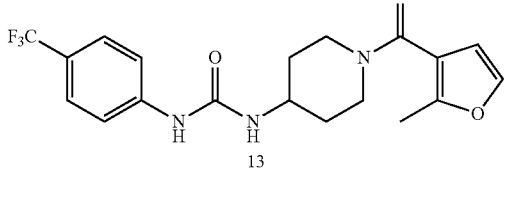 13 | 0.28 | 2.1 |
| 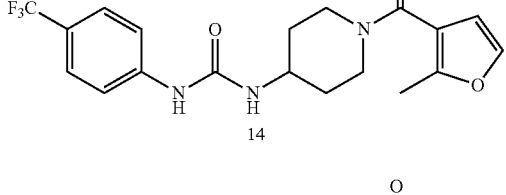 14 | 0.8 | 1.8 |
| 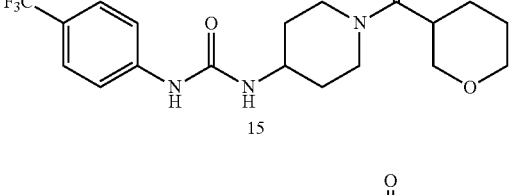 15 | 1.1 | 25 |
| 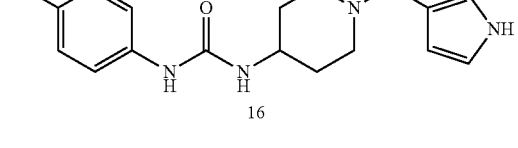 16 | 1.8 | 13 |

TABLE II-continued
Compound Solubility (at pH 7 and pH 3)
| Structure | Solubility[a] (ug/mL) | Sol[b] (ug/mL) at pH3 |
|---|---|---|
| 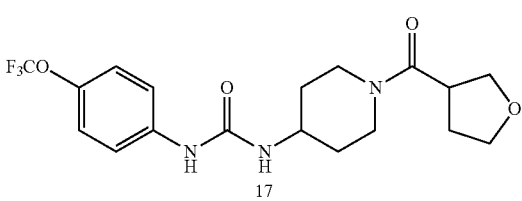 17 | 29 | 91 |
| 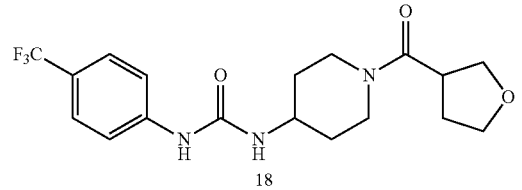 18 | 9.6 | 50 |
| 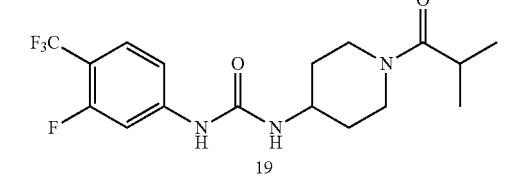 19 | 5.3 | 5.1 |
| 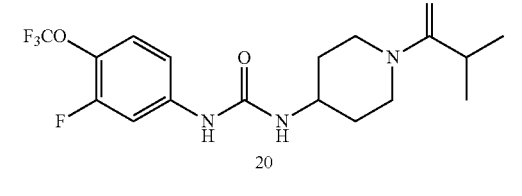 20 | 5.9 | 6 |
| 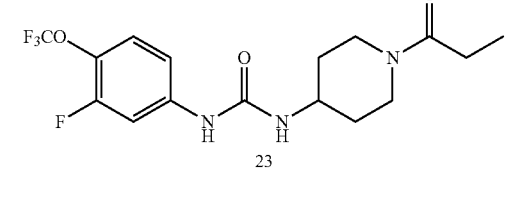 23 | 11 | N.D. |
| 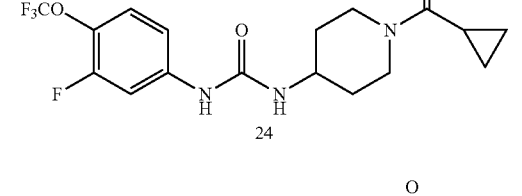 24 | 19 | N.D. |
| 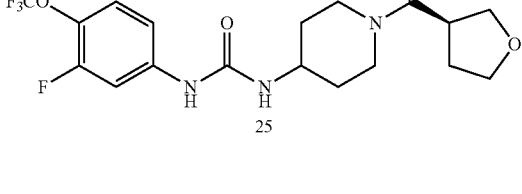 25 | 61 | 196 |

TABLE II-continued

Compound Solubility (at pH 7 and pH 3)

| Structure | Solubility$^a$ (ug/mL) | Sol$^b$ (ug/mL) at pH3 |
|---|---|---|
| 26 | 11 | N.D. |
| 27 | 174 | 522 |
| 28 | N.D. | N.D. |
| 29 | 77 | 206 |
| 30 | N.D. | N.D. |
| 31 | 3.9 | N.D. |
| 32 | 13 | N.D. |

TABLE II-continued

Compound Solubility (at pH 7 and pH 3)

| Structure | Solubility$^a$ (ug/mL) | Sol$^b$ (ug/mL) at pH3 |
|---|---|---|
| 33 | 1.9 | 3.1 |
| 34 | 0.46 | N.D. |
| 35 | 11 | 40 |
| 36 | 0.08 | N.D. |
| 37 | 42 | 122 |
| 40 | 0.35 | N.D. |
| 41 | N.D. | N.D. |

TABLE II-continued
Compound Solubility (at pH 7 and pH 3)
| Structure | Solubility[a] (ug/mL) | Sol[b] (ug/mL) at pH3 |
|---|---|---|
| 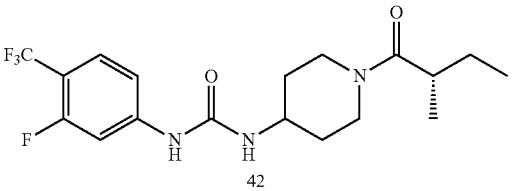 42 | 272 | 662 |
| 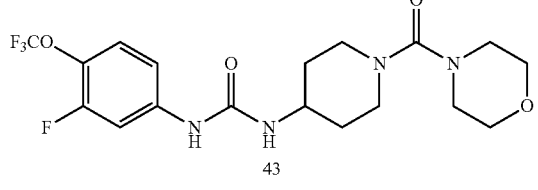 43 | 96 | N.D. |
| 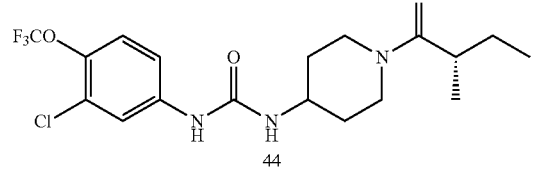 44 | 0.79 | N.D. |
| 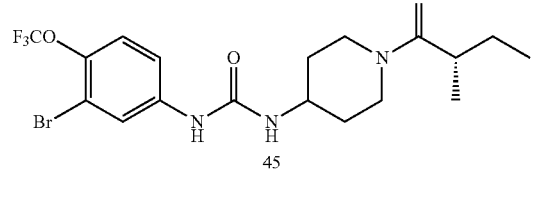 45 | 0.58 | N.D. |
| 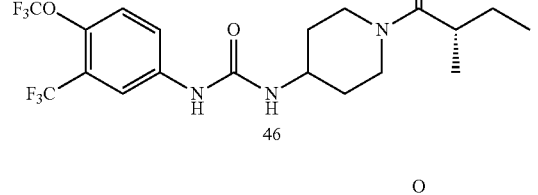 46 | 0.05 | N.D. |
| 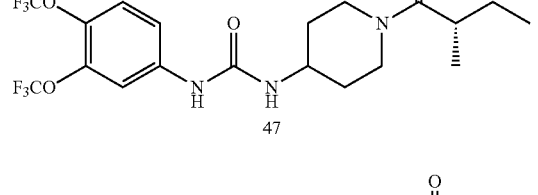 47 | 5.5 | N.D. |
| 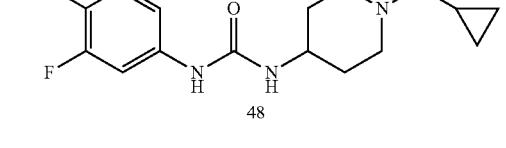 48 | 715 | N.D. |

TABLE II-continued

Compound Solubility (at pH 7 and pH 3)

| Structure | Solubility$^a$ (ug/mL) | Sol$^b$ (ug/mL) at pH3 |
|---|---|---|
| 49 | 21 | N.D. |
| 1770 | 60 | 58 |
| 2389 | 7.2 | N.D. |
| 2422 | 27 | N.D. |
| APAU | 277 | N.D. |

Abbreviation:
Sol: solubility;
$K_i$: inhibition constant;
ND: not determined
$^a$The solubility of the drugs were measured at Phosphate Buffer at pH 7.4
$^b$The solubility of the drugs were measured at Acetate Buffer at pH 3

Figure 3:
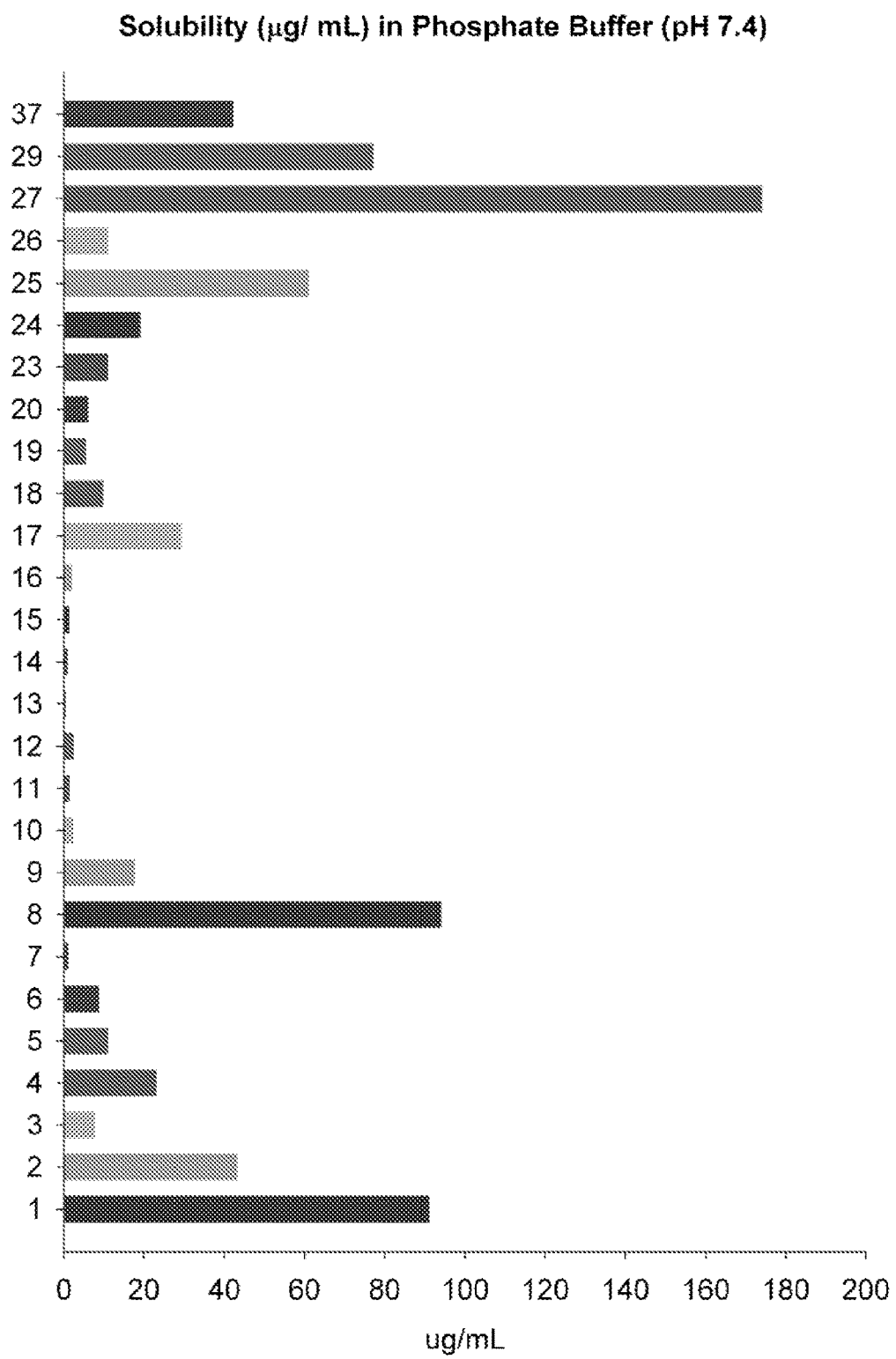
FIG. 3 is a graph showing the solubility of selected inhibitors at pH 7.4.

Unlike all the other heterocycles, the incorporation of tetrahydropyran to sEH inhibitors (Formula (II)) at $R_7$ is able to remarkably enhance the solubility of sEH inhibitors as compared to the sEH inhibitors with hydrophobic alkyl group at $R_7$ of Formula (II) (Table II and FIG. 3; Compounds 1, 8, 27 and 29).

Figure 2:
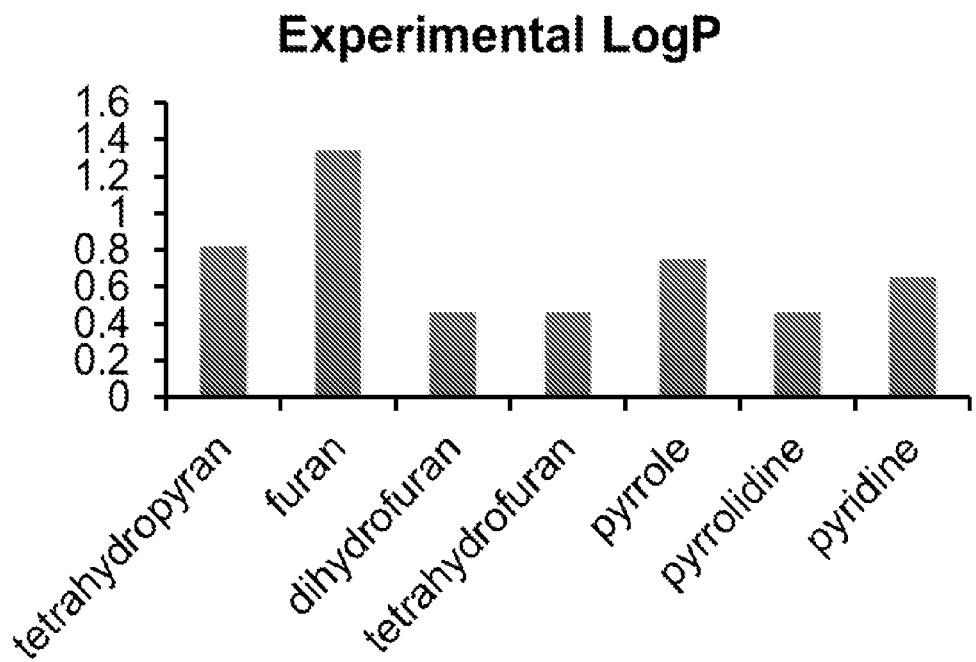
FIG. 2 is a graph showing the experimental logP relationship of different heterocycles attached at $R_7$ of Formula (II) and it does not correlate with the enhanced solubility that was achieved as shown in Table II.

The enhanced solubility from tetrahydropyran at $R_7$ is surprising because it does not correlated with the dipole moment of the heterocycles or the experimental logP of the heterocycles (FIGS. 1 and 2).

Figure 4:
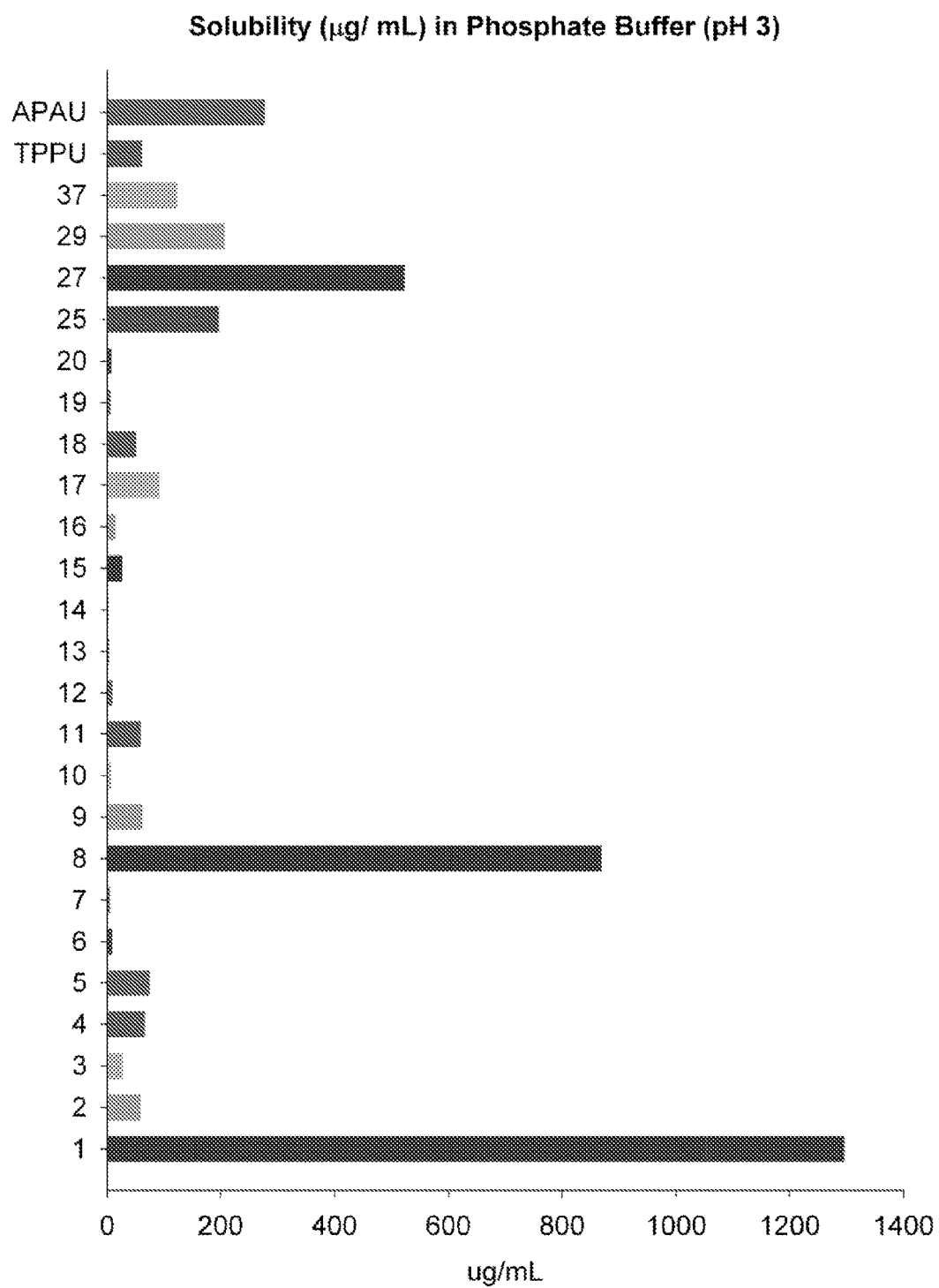
FIG. 4 is a graph showing the solubility of selected inhibitors at pH 3.0.
Figure 5:
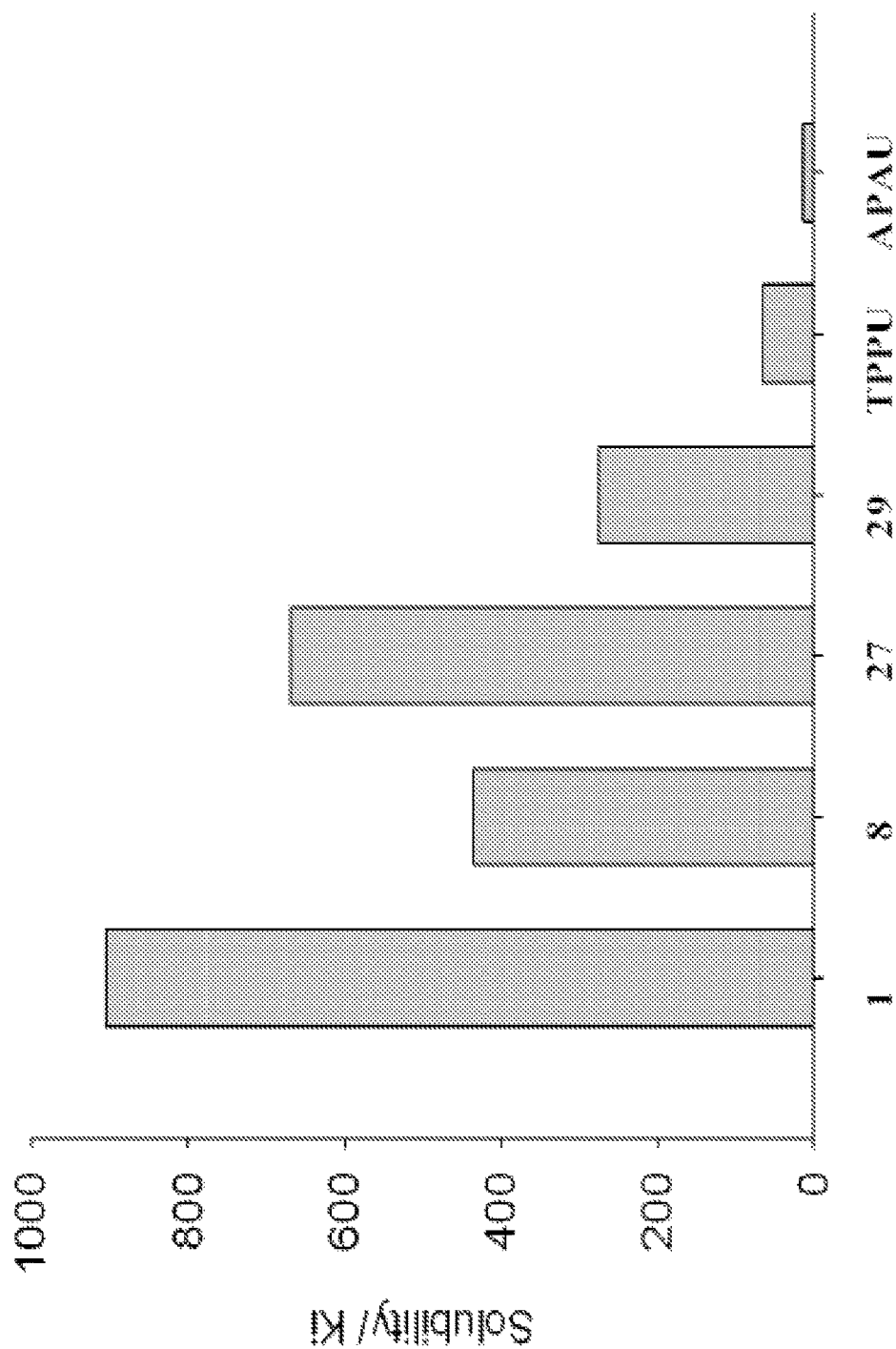
FIG. 5 is a plot showing the solubility of selected compounds at pH 3.0 over their potency ($K_i$).

Surprisingly, and in contrast to sEH inhibitors of Formula (II) with alkyl substituents (ethyl, cyclopropyl, 2-sec-butyl-group) at $R_7$, the sEH inhibitors with heterocycles show enhanced solubility of at least 3 fold at pH 3, a pH value of stomach acid, as compared to solubility at pH 7 while maintaining the potency of the inhibitor to single digit nanomolar level (Tables 1 and 2 and FIGS. 4 and 5).

Apart from other heterocycles, sEH inhibitors (Formula (II)) with tetrahydropyran at $R_7$ show an unexpected enhanced solubility at pH 3. The inhibitors with tetrahydropyran at $R_7$ have a solubility at acidic pH 3 at least 5 times better than any other sEH inhibitors Formula (II) with alky group at $R_7$ and the solubility of several of these inhibitors (Compounds 1, 8 and 27) at pH 3 are much better than the most soluble 1,3-disubstituted urea sEH inhibitors (Compound APAU) (Table II and FIG. 4). This enhances the druglikeness of these series of sEH inhibitors. Because one of the main organs for drug absorption: the stomach, has a strongly acidic environment. The exceptionally enhanced solubility at pH 3 by the inhibitors with tetrahydropyran improves their absorption and oral bioavailability fulfilling an important need in the area.

Accordingly, the present invention provides a method for increasing the water solubility of a compound of Formula (I) by incorporating a heteroatom at X.

In a related aspect, the present invention provides a method for increasing the water solubility of a compound of Formula (II) by incorporating a heterocycle at $R_7$.

Modifications of the structures of inhibitors usually have small and apparently random effects on melting point of the compounds. However, unexpectedly and surprisingly, addition of fluorine atom at $R_2$ of Formula I and at $R_6$ of Formula II, decreases the melting point of this series of sEH inhibitors by an average about 20° C. with improved potency (Tables I and III). The decrease of melting point not only eases the formulation process of drugs but also enhances the oral bioavailability of the drugs in general, and reduces problems with stable polymorphs. Therefore improvements made to decrease high melting point are always sought after in the industry.

TABLE III

Compound Melting Point (incorporation of fluorine at R2 position of Formula (I) or $R_6$ position of Formula (II) decreases melting point of the sEH inhibitors (° C.)

| Original inhibitor | Melting Point (° C.) | Meta-F Substituent Inhibitor | Melting Point (° C.) | Melting Point Decrease[a] (° C.) | Potency Enhancement[b] |
|---|---|---|---|---|---|
| 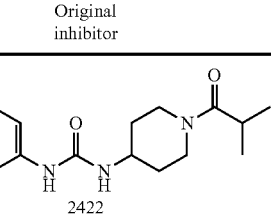 2422 | 179.1-180.3 (179.6) | 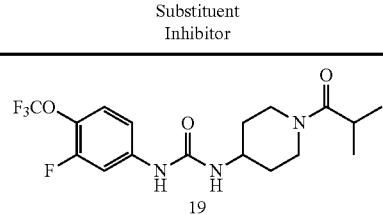 19 | 156.9-157.6 (157.2) | −22.4 | 1.00 |
| 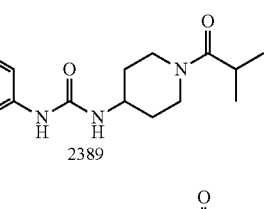 2389 | 234.1-235.4 (234.9) | 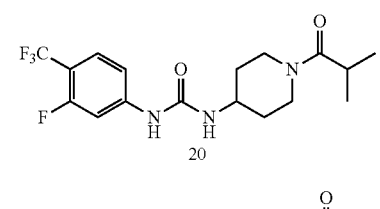 20 | 198.2-200.9 (199.2) | −35.7 | 1.35 |
| 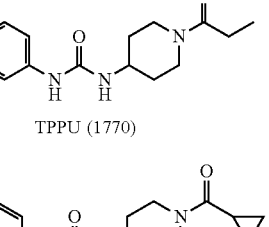 TPPU (1770) | 198.2-200.8 (199.5) | 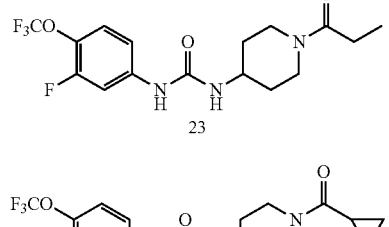 23 | 172.6-173.1 (172.8) | −26.7 | 1.05 |
| 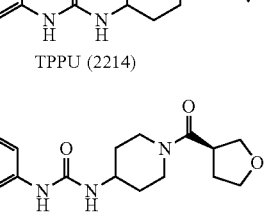 TPPU (2214) | 193.4-194.2 (193.8) | 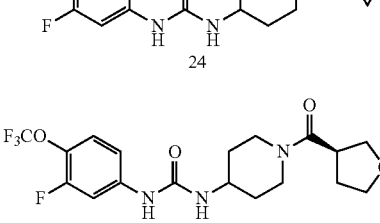 24 | 178.1-178.9 (178.5) | −15.3 | 3.67 |
| 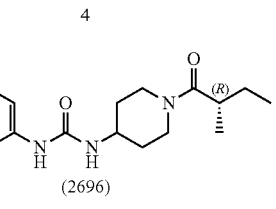 4 | 180.5-181.7 (180.8) | 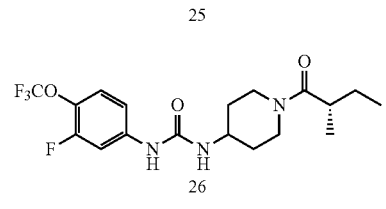 25 | 168.2-169.7 (168.9) | −11.9 | 2.10 |
| 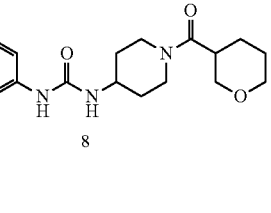 (2696) | 168.0-169.3 (168.7) | 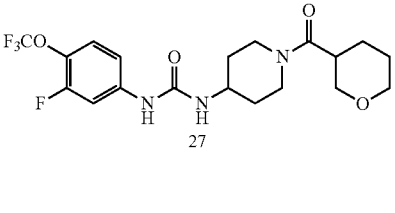 26 | 147.0-147.8 (146.2) | −22.5 | 3.80 |
|  8 | 176.2-177.7 (177.1) |  27 | 158.2-159 (158.4) | −18.7 | 2.55 |

TABLE III-continued

Compound Melting Point (incorporation of fluorine at R2 position of Formula (I) or R_6 position of Formula (II) decreases melting point of the sEH inhibitors (° C.)

| Original inhibitor | Melting Point (° C.) | Meta-F Substituent Inhibitor | Melting Point (° C.) | Melting Point Decrease[a] (° C.) | Potency Enhancement[b] |
|---|---|---|---|---|---|
| 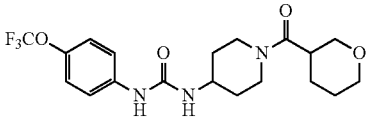 [SMILES: O=C(Nc1ccc(OC(F)(F)F)cc1)NC1CCN(C(=O)C2CCCOC2)CC1] 1 | 177.4-178.7 (177.9) | 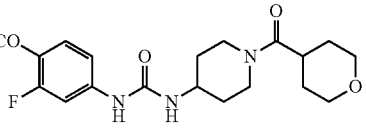 29 | 172.2-174.0 (173.1) | −4.8 | 2.31 |
| 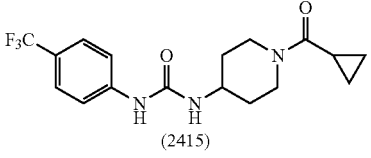 (2415) | 193.4-194.2 (193.7) | 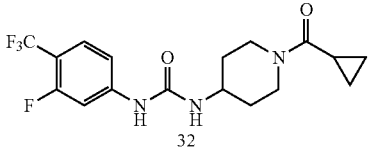 32 | 181.3-182.8 (182.1) | −11.6 | 1.29 |
| 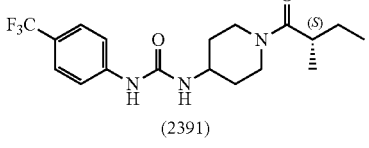 (2391) | 221.3-225.6 (221.6) | 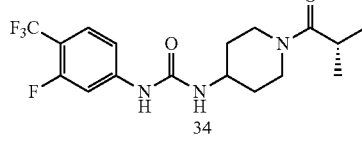 34 | 208.0-209.4 (208.7) | −12.9 | 0.59 |
| 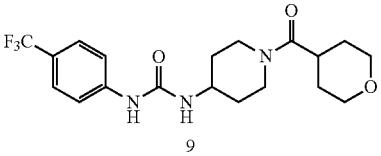 9 | 243.0-243.6 (243.2) | 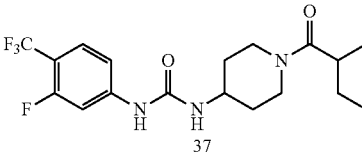 37 | 219.8-221.8 (220.8) | −22.4 | 0.45 |
| 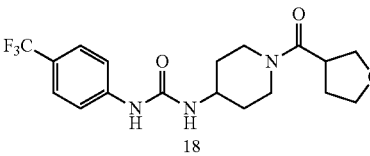 18 | 238.2-239.3 (238.6) | 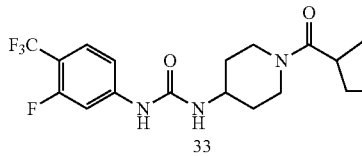 33 | 227.4-229.3 (228.0) | −10.6 | 0.57 |
| 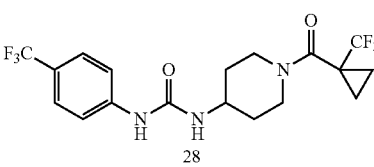 28 | 263.3-265.3 (264.3) | 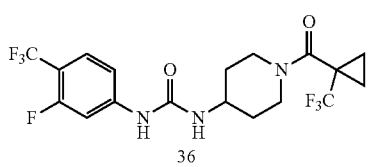 36 | 236.4-2383 (237.4) | −26.9 | 1 |
| 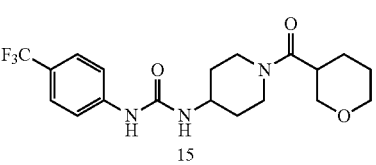 15 | 253.9-255.2 (254.2) | 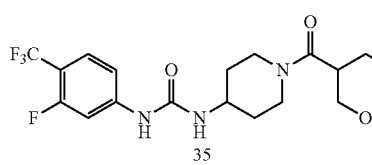 35 | 236.5-238.3 (237.4) | −16.8 | 0.90 |
| 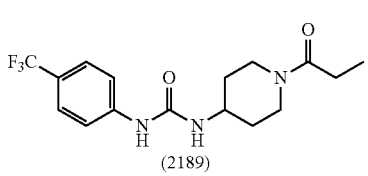 (2189) | 224-228 (226) | 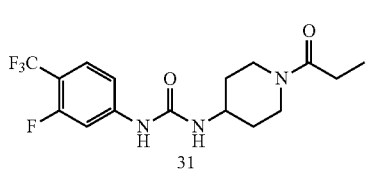 31 | 216.2-216.8 (216.5) | −9.5 | 1 |

Abbreviation:
Sol: solubility
[a]Melting point change = Melting point of inhibitors with meta-F substitution to urea of aryl group-Melting point of original inhibitors.
[b]Potency Enhancement = $K_i$ of original inhibitors/$K_i$ of meta-F substituted inhibitors.

Figure 6:
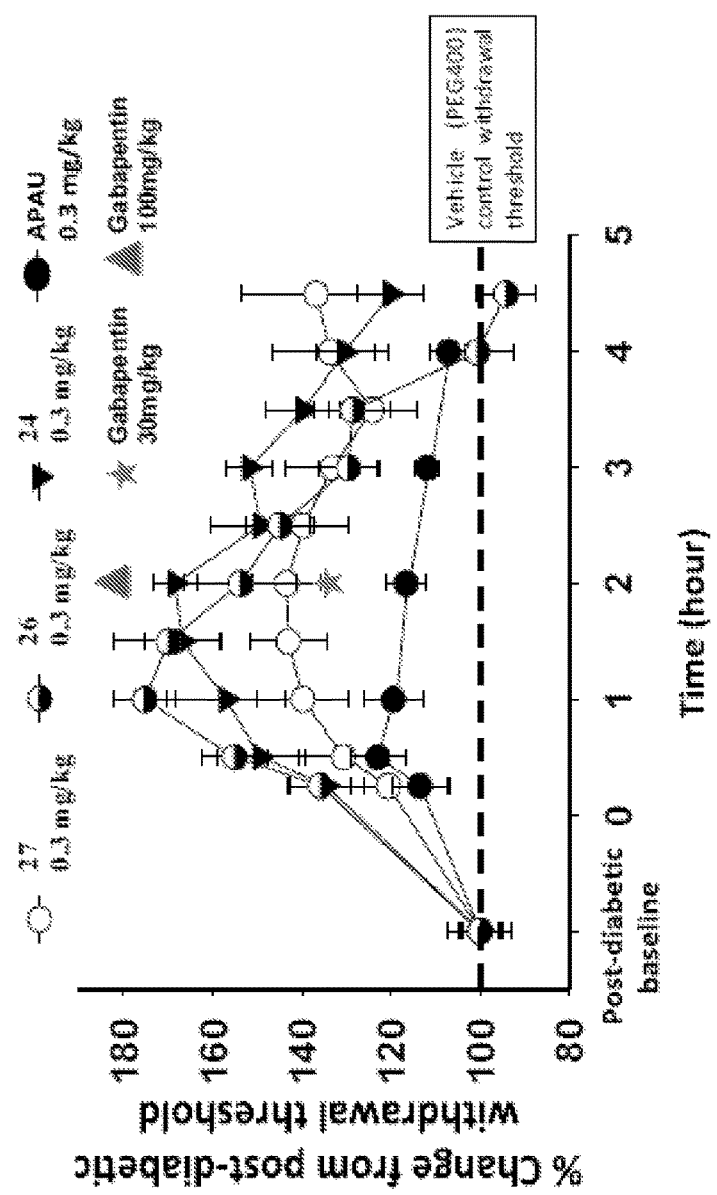
FIG. 6 is a graph showing the anti-nociceptive effects of inhibitors with enhanced drug-like properties and these inhibitors have much better in vivo efficacy than the clinical approved drug gabapentin at 100× dose.

The fluorine substitution at $R_6$ of Formula (II) is unique because substitution including halogens other than fluorine at $R_6$ of Formula (II) increases the melting point of the inhibitors and most of those substitutions hamper the potency of the inhibitors (Table I and FIG. 6).

Moreover, in this case, addition of fluorine atom at $R_2$ of Formula (I) or at $R_6$ of Formula (II) enhanced the potency of sEH inhibitors by about 2-fold (Table I). Thus, this modification reduces crystal stability and increases ease of formulation (as indicated by melting point reduction) by increasing potency on the target.

Accordingly, the present invention provides a method for decreasing the melting point of a compound of Formula (I) by incorporating fluorine at $R_2$.

In a related aspect, the present invention provides a method for decreasing the melting point of a compound of Formula (II) by incorporating fluorine at $R_6$.

Figure 9:
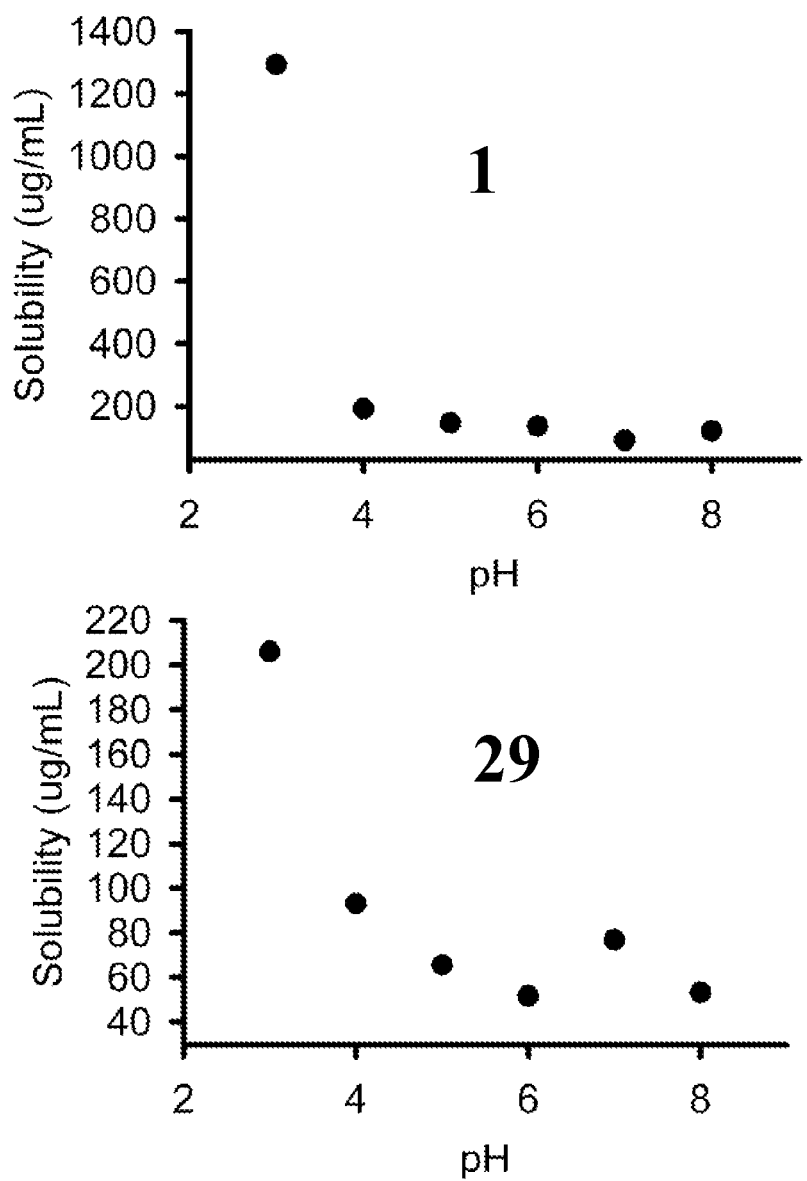
FIG. 9 is a series of graphs showing that the solubility of Compounds 1 and 29 increase with pH increases.

A combination of these distinct approaches to improve the inhibitors, i.e., incorporation of fluorine atom at $R_6$ and tetrahydropyran at $R_7$ of Formula (II), led to surprisingly ultrapotent, sub-nanomolar potency with remarkably high water solubility (>100 μg/mL) (Compound 27, Table 2 and FIGS. 3 and 4) and lower melting points (Table III). These modifications significantly enhance the druglikeness of the inhibitors compared to all earlier sEH inhibitors.

pH titration on Compounds 1 and 29 shows that the solubility increases dramatically when the pH is below 4 (FIG. 9).

Accordingly, the present invention provides a method for increasing water solubility of a compound of Formula (I) in the range of pH 1-7, by incorporating oxygen at X and subscript m is 2 and n is 2.

In a related aspect, the present invention provides a method for increasing water solubility of a compound of Formula (II) in the range of pH 1-7, by incorporating a heterocycle at $R_7$.

In embodiments, the range of pH is about 1-7, 2-5, 2-4, 3-4 or about 1, 2, 3, 4, 5, 6 or 7.

Incorporation of large alkyl group at $R_7$ and trifluoromethoxy- group at $R_5$ of Formula II (e.g., Compound 26) led to inhibitors with long residence time (t1/2~20 min) as compared to APAU (t1/2~6 min) that display better in vivo efficacy, validating the value of approaches disclosed in herein (Table I).

As such, the present invention provides a method for increasing the residence time (t1/2) on soluble epoxide hydrolase of a compound of Formula (I) by incorporating trifluoromethoxy- group at $R_1$.

TABLE IV

Compound Melting Point and $K_i$ (Incorporation of other substitute at $R_2$ position of Formula (I) or $R_6$ position of Formula (II) increases melting point of the sEH inhibitors (° C.) except fluorine)

| Structure | Mol. Weight | Melting Point (° C.) | Ki nM | Melting Point Change[a] (° C.) |
|---|---|---|---|---|
| 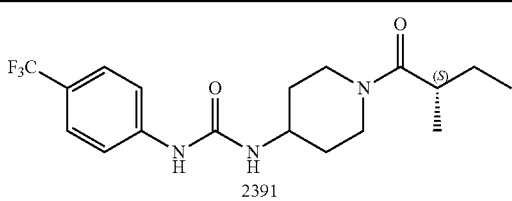 2391 | 371.40 | 221.3-225.6 (221.6) | 0.22 ± 0.04 | Not applicable |
| 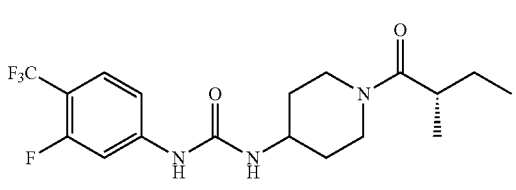 [SMILES: CC[C@H](C)C(=O)N1CCC(NC(=O)Nc2ccc(C(F)(F)F)c(F)c2)CC1] Syn34 | 389.39 | 208.0-209.4 (208.7) | 0.37 ± 0.03 | −12.9 |
| 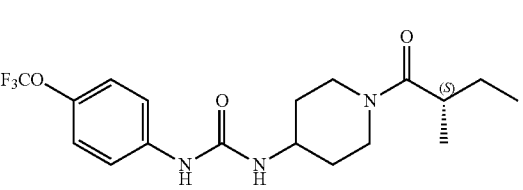 2696 | 387.40 | 168.0-169.3 (168.7) | 0.19 ± 0.04 | Not applicable |
| 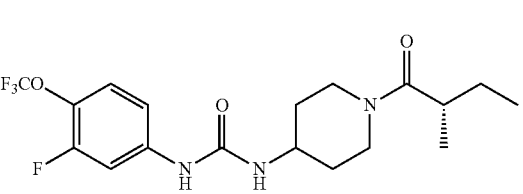 26 | 405.39 | 147.0-147.8 (146.2) | <0.05 | −22.5 |

TABLE IV-continued

Compound Melting Point and $K_i$ (Incorporation of other substitute at $R_2$ position of Formula (I) or $R_6$ position of Formula (II) increases melting point of the sEH inhibitors (° C.) except fluorine)

| Structure | Mol. Weight | Melting Point (° C.) | $K_i$ nM | Melting Point Change[a] (° C.) |
|---|---|---|---|---|
| 44 | 421.85 | 183.9-184.5 (184.2) | 3.35 ± 0.42 | +15.5 |
| 45 | 465.29 | 197.6-198.5 (198.0) | 3.40 ± 1.38 | +29.3 |
| 46 | 455.40 | 201.1-202.1 (201.6) | 9.91 ± 3.37 | +32.9 |
| 47 | 471.40 | 170.8-172.4 (171.6) | 9.07 ± 0.36 | +2.9 |

[a] Melting point change = Melting point of inhibitors with substitution to urea at aryl group-Melting point of original inhibitors.

Figure 7:
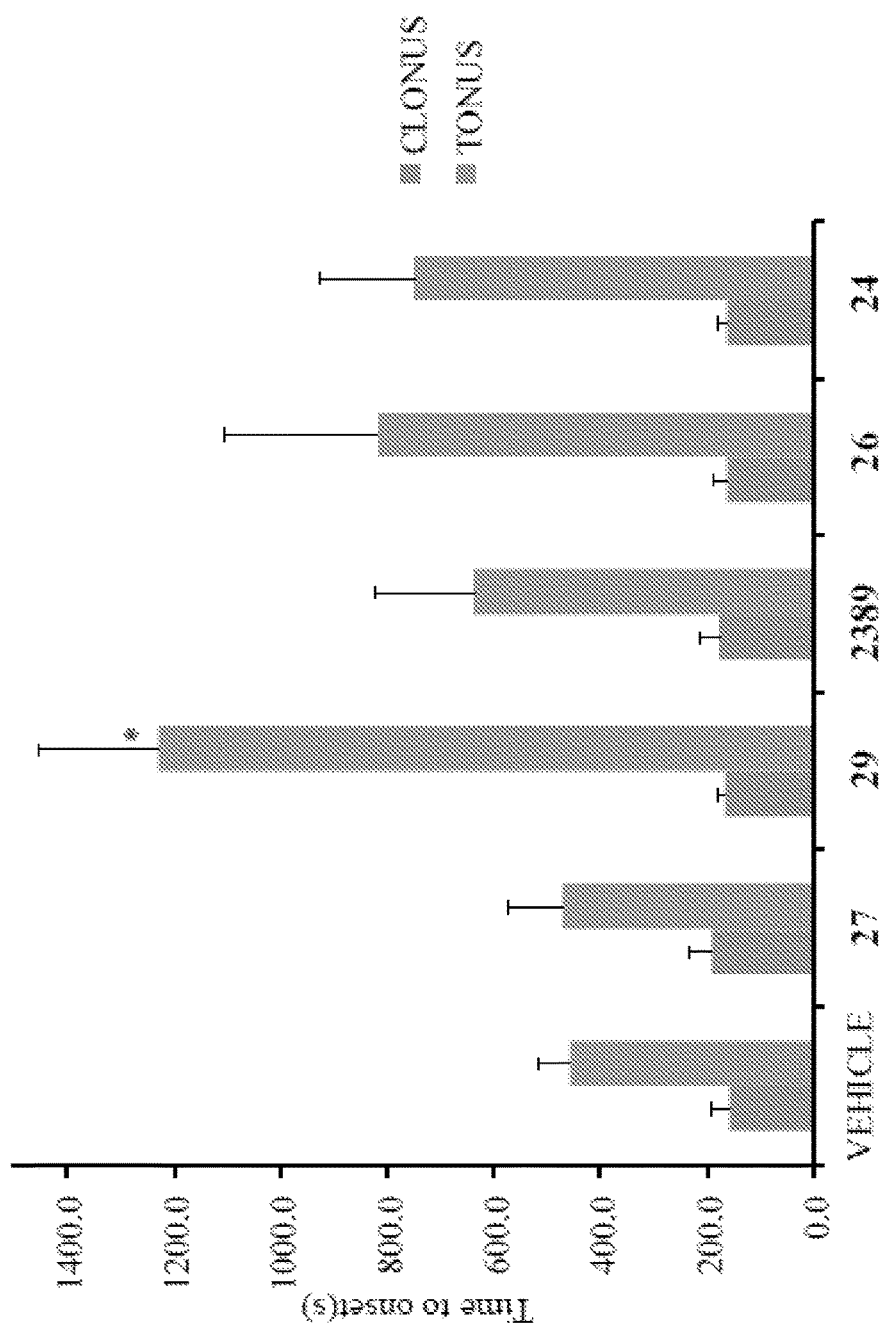
FIG. 7 is a graph showing the anticonvulsant efficacy of sEH inhibitors (0.3 mpk, subcutaneous injection) against subcutaneous pentylenetetrazole). Among five 1,3-disubstituted urea based sEH inhibitors, Compound 29 delayed onset of the tonic phase of seizure in wild type Swiss mice (*=p<0.05).

Through standard chemically induced seizure assay, compounds of the present disclosure were determined to protect mice from convulsions and associated lethality demonstrating that the present compound are able to cross a subject's blood-brain barrier (Example 52 and FIG. 7).

As discussed in Example 54 below, in nociceptive assays using type I diabetic rats, the compounds of the present disclosure outperformed a standard drug registered for neuropathic pain, gabapentin and a standard sEH inhibitor (Compound APAU). The compounds of the present disclosure reached high levels of efficacy more rapidly. Moreover, the compounds of the present disclosure displayed higher potency and also higher efficacy compared to standards in the field (FIG. 6).

Additionally, the compounds of the present disclosure displayed significant efficacy in a seizure assay due to the ability of the compounds to cross the blood brain barrier, thereby readily penetrating the CNS and protecting the subject from seizure (Example 52).

Methods and Therapeutic Uses

Administration of inhibitors of sEH, has been found to have a number of beneficial applications as described in U.S. Pat. Nos. 8,815,951, 8,513,302, 8,399,425, 8,501,783, 7,662,910 as well as U.S. Patent Publication Nos. 2015/0065540 and 2015/0017267 which are incorporated by reference herein in their entireties.

As such, the present invention provides a method for inhibiting a soluble epoxide hydrolase, comprising contacting the soluble epoxide hydrolase with an inhibiting amount of a compound having the Formula (I) or (II), above.

Preferably, the inhibitor inhibits sEH without also significantly inhibiting microsomal epoxide hydrolase ("mEH"). Preferably, at concentrations of 500 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 500 µM. Inhibitors with $IC_{50}$s of less than 500 µM are preferred, with $IC_{50}$s of less than 200 µM being more preferred, 100 µM being still more preferred and $IC_{50}$s of 50 µM, 40 µM, 30 µM, 25 µM, 20 µM, 15 µM, 10 µM, 5 µM, 3 µM, 2 µM, 1 µM or even less being the more preferred as the $IC_{50}$ decreases. Assays for determining sEH activity are known in the art and described elsewhere herein.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

As such, the present invention provides a method of treating an sEH mediated disease or condition as defined herein. The method includes administering to a subject in need of such treatment an effective amount of a compound having a formula selected from Formula (I) or (II). In one aspect, the effective amount is a therapeutically effective amount.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, drageemaking, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations of the present invention may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In preferred aspects, the formulations are for topical application to the eye, nose, or ear in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

For ophthalmic disorders, components of the invention may be delivered to the eye as a concentrated gel or a similar vehicle, or as dissolvable inserts that are placed beneath the eyelids.

The formulations of the present invention that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

Preferred formulations are prepared using a buffering system that maintains the formulation at a pH of about 4.5 to a pH of about 8. A most preferred formulation pH is from 6 to 8.

In particular embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower ($C_1$-$C_6$) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used.

The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose), synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g., orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetic neuropathic pain involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Examples 1-51

All reagents and solvent were purchased from commercial suppliers and were used directly without further purifications. All syntheses were carried out in a dry nitrogen atmosphere unless otherwise specified. Reactions were monitored by thin-layer chromatography (TLC, on Merck $F_{254}$ silica gel 60 aluminum sheets, spots were either visible under light or UV-light (254 mm) or stained with an oxidizing solution ($KMnO_4$ stain). The same TLC system was used to test purity, and all final products showed a single spot on TLC. Column chromatography was performed with silica gel.

$^1$H-NMR spectra were recorded on a Varian QE-300 spectrometer with deuterated chloroform ($CDCl_3$; $\delta=7.24$ ppm) or deuterated dimethyl sulfoxide ($DMSO-d_6$) containing TMS an internal standard. $^{13}$C-NMR spectra were recorded on a Varian QE-300™ spectrometer at 75 MHz.

The purity of the inhibitors reported herein were determined either by 1) HPLC-UV using Agilent 1200™ series HPLC series equipped with Phenomenex™ Luna2 C18 reverse phase column (C18, 4.6 mm×150 mm, 5 μm) coupled with Agilent G1314 UV-vis detector (Detection at 230 nm) with isocratic flow at Methanol:Water (2:1 by volume) for 90 min; or by 2) H-NMR. The lowest obtained purity was reported. The inhibitor was dissolved in EtOH at 100 μM and 10 μL was injected on HPLC. Purity was based on the percent of total peak area at 230 nm using HPLC-UV. This purity estimate was compared with that from the H-NMR. The presence of anilines in the final product was estimated from H-NMR. The lowest obtained purity was reported. The purity was also further supported as described in the supplementary materials by LC/MS with monitoring of total ion current, TLC in several systems, a sharp melting point and occasional other technique. The elemental analysis was conducted by MIDWESTMICRO lab, LCC.

The synthesis of tert-butyl 4-(3-(4-(trifluoromethyl)phenyl)ureido) piperidine-1-carboxylate, 1-(piperidin-4-yl)-3-(4-(trifluoromethyl)phenyl)urea, 1-(piperidin-4-yl)-3-(4-(trifluoromethoxy)phenyl)urea and tert-butyl 4-(3-(4-(trifluoromethoxy)phenyl)ureido)piperidine-1-carboxylate have been previously reported.

Example 1

General Synthetic Scheme for sEH Inhibitors

The compounds of the present invention are prepared by a variety of methods as outlined in the following general synthetic scheme.

Synthetic Pathway 1

Step 1

Corresponding isocyanate (1 equiv.) and 4-amino-1-Boc-piperidine (1.1 equiv.) was dissolved in $CH_2Cl_2$ (50 mM, corresponding to isocyanate) and stirred at rt for 12 h. The reaction was quenched by addition of water. The organic layer was isolated and the aqueous layer was extracted with EtOAc (EtOAc:Aqueous layer/1:1 (v:v)) for 4 times. The combined organic layer was dried over anhydrous magnesium sulfate and was concentrated under vacuo and was further purified by flash chromatography yielding corresponding Boc-protected urea.

General Synthetic Scheme

Synthetic Pathway 1

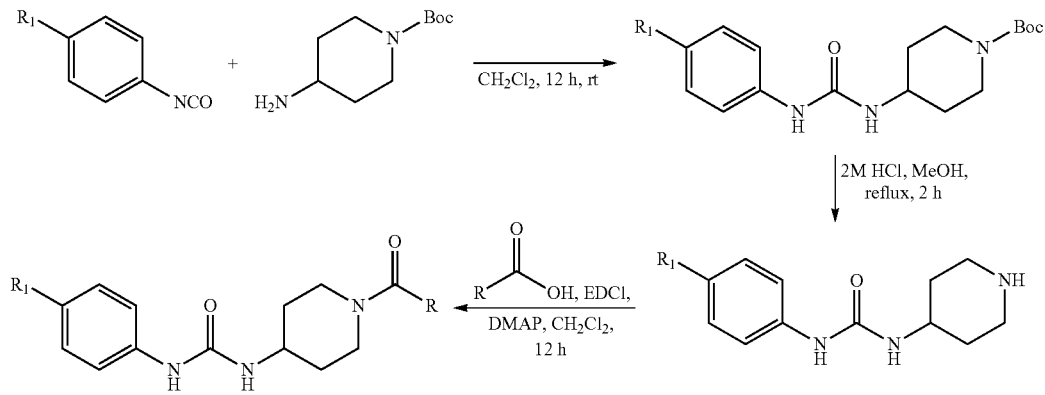

Synthetic Pathway 2

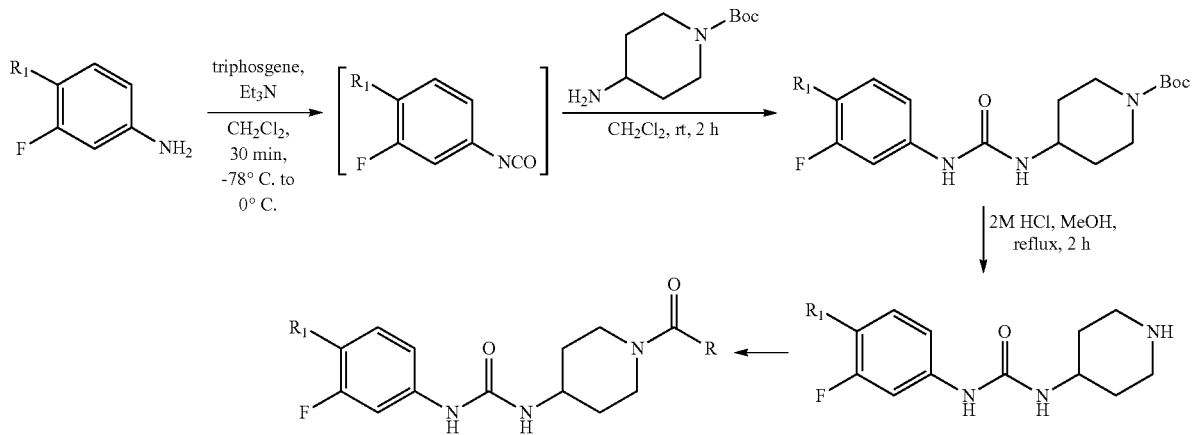

Synthetic Pathway 3

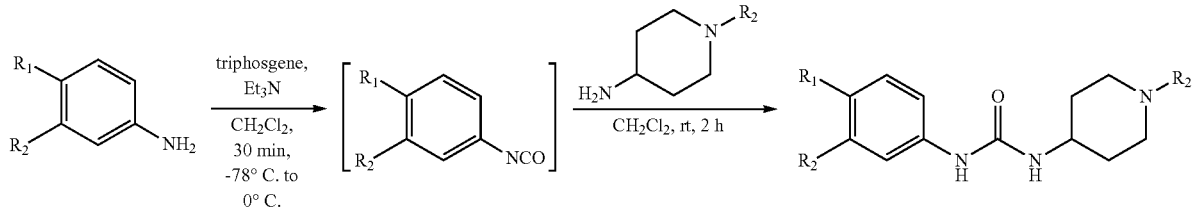

Step 2

The Boc protected urea from the step 1 was dissolved in HCl solution (2M, MeOH) to make reaction mixture (186 mM, Boc protected urea). The resulting solution was refluxed for 2 h. The solvent was removed under vacuo and the crude reaction product was adjusted to pH 12 with NaOH. The precipitates were filtered and dried under high vacuum. The final unprotected urea was served as a scaffold for the next step of synthesis.

Step 3

Unless specified, the unprotected urea (1 equiv.) from step 2, EDCI (1.5 equiv.), DMAP (1.5 equiv.) and corresponding carboxylic acid (1.5 equiv.) was dissolved in CH$_2$Cl$_2$ (8.3 mM, unprotected urea) and was stirred overnight (12 h) at rt. The reaction was quenched by addition of HCl solution (1M). The organic layer was collected and the aqueous layer was extracted with EtOAc (EtOAc:Aqueous layer/1:1(v:v)) for 4 times. The combined organic layer was dried over anhydrous magnesium sulfate and was concentrated in vacuo and further purified by flash chromatography.

Synthetic Pathway 2

Step 1

Corresponding amine (1 equiv.) and triethylamine (1.5 equiv.) was dissolved in CH$_2$Cl$_2$ (54 mM corresponding to amine) and stirred at −78° C. Triphosgene (0.45 equiv.) dissolved in CH$_2$Cl$_2$ (20 mM, corresponding triphosgene) was added dropwise at −78° C. The reaction was then warm to rt and was stirred for 30 min. The reaction was cooled to 0° C. Corresponding piperidine (1.5 equiv.) and triethylamine (1.5 equiv.) dissolved in CH$_2$Cl$_2$ (54 mM, corresponding piperidine) was added slowly and the reaction was further stirred at rt for 12 h. The reaction was quenched with the addition of HCl solution (2M). The organic layer was collected and the aqueous layer was further extracted with EtOAc (EtOAc:Aqueous layer/1:1) for three times. The combined organic layer was washed with sat. NaCl solution. The organic layer was dried over anhydrous magnesium sulfate and was concentrated in vacuo. The product was used without further purification.

Step 2

The Boc protected urea from the step 1 was dissolved in HCl solution (2M, MeOH) to make reaction mixture (186 mM, Boc protected urea). The resulting solution was refluxed for 2 h. The solvent was removed under vacuo and the crude reaction product was adjusted to pH 12 with NaOH. The precipitates were filtered and dried under high vacuum. The final unprotected urea was served as a scaffold for the next step of synthesis.

Step 3

Unless specified, the unprotected urea (1 equiv.) from step 2, EDCI (1.5 equiv.), DMAP (1.5 equiv.) and corresponding carboxylic acid (1.5 equiv.) was dissolved in CH$_2$Cl$_2$ (8.3 mM, unprotected urea) and was stirred overnight (12 h) at rt. The reaction was quenched by addition of HCl solution (1M). The organic layer was collected and the aqueous layer was extracted with EtOAc (EtOAc:Aqueous layer/1:1(v:v)) for 4 times. The combined organic layer was dried over anhydrous magnesium sulfate and was concentrated in vacuo and further purified by flash chromatography.

Synthetic Pathway 3

Corresponding amine (1 equiv.) and triethylamine (1.5 equiv.) was dissolved in CH$_2$Cl$_2$ (54 mM corresponding to amine) and stirred at −78° C. Triphosgene (0.45 equiv.) dissolved in CH$_2$Cl$_2$ (20 mM, corresponding triphosgene) was added dropwise at −78° C. The reaction was then warm to rt and was stirred for 30 min. The reaction was cooled to 0° C. Corresponding piperidine (1.5 equiv.) and triethylamine (1.5 equiv.) dissolved in CH$_2$Cl$_2$ (54 mM, corresponding piperidine) was added slowly and the reaction was further stirred at rt for 12 h. The reaction was quenched with the addition of HCl solution (2M). The organic layer was collected and the aqueous layer was further extracted with EtOAc (EtOAc:Aqueous layer/1:1) for three times. The combined organic layer was washed with sat. NaCl solution. The organic layer was dried over anhydrous magnesium sulfate and was concentrated in vacuo. The product was purified by flash chromatography.

Example 2

Synthesis of tert-butyl 4-(3-(3-fluoro-4-(trifluoromethoxy)phenyl)ureido)piperidine-1-carboxylate (A)

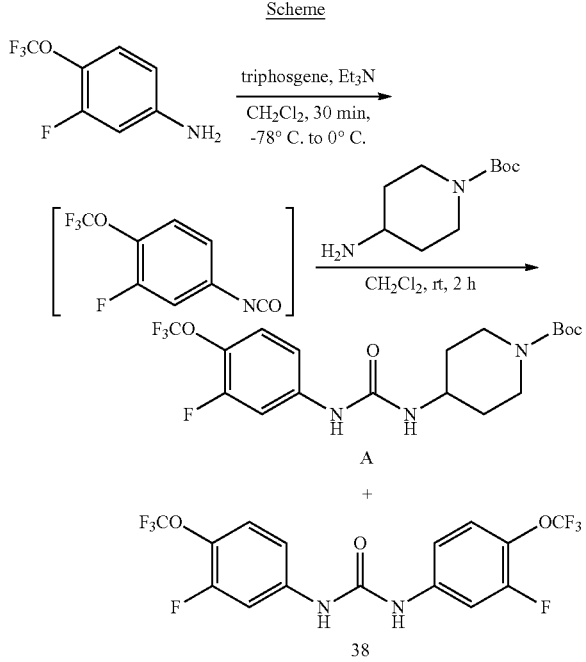

meta-Fluoro-4-(trifluoromethoxy)aniline (500 mg, 2.56 mmol) and triethylamine (388 mg, 3.84 mmol) were dissolved in CH$_2$Cl$_2$ (4 mL) and was added dropwisely into a solution of triphosgene (341 mg, 1.15 mmol) dissolved in CH$_2$Cl$_2$ (5 mL) at −78° C. The reaction mixture was stirred at 0° C. for 1 h and was then cooled to −78° C. 4-amino-1-Boc-piperidine (769 mg, 3.84 mmol) and triethylamine (388 mg, 3.84 mmol) were dissolved in CH$_2$Cl$_2$ (4 mL) and the suspension was added dropwisely to the reaction mixture at −78° C. The reaction mixture was stirred at rt for 2 h. The reaction was quenched by addition of water. The organic layer was isolated and the organic layer was further washed by HCl solution (1M) for 4 times. The organic layer was dried over anhydrous magnesium sulfate and concentrated in vacuo yielding final crude product (1.05 g, 86% pure, 2.13 mmol, 83.4% yield). The impurities 38 were purified by column chromatography using EtOAc:Hex (1:1).

$^1$H NMR (d$_6$-DMSO, 300 Mhz): A: ∂ 8.77 (s, 1H), 7.66 (dd, J=13.5, 2.4 Hz, 1H), 7.38 (t, J=8.1 Hz, 1H), 7.10 (d, J=9 Hz, 1H), 6.33 (d, J=7.5 Hz, 1H), 3.81 (d, J=12.9 Hz, 2H), 3.6-3.8 (m, 1H), 2.8-3.0 (m, 2H), 1.78 (dd, J=12.3 Hz, 3.3

Hz, 2H), 1.40 (s, 9H), 1.2-1.4 (m, 2H); 38: ∂ 9.28 (s, 1H), 7.69 (dd, J=14.9, 2.4 Hz, 1H), 7.46 (t, J=9 Hz, 1H), 7.2-7.3 (m, 1H)

Example 3

Synthesis of 1-(1-(tetrahydro-2H-pyran-4-carbonyl) piperidin-4-yl)-3-(4-(trifluoromethoxy)phenyl)urea

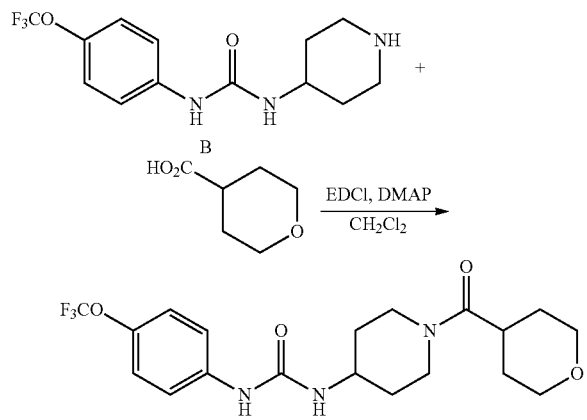

The reaction was carried out according to synthetic pathway 1, step 3. Piperidine B (80 mg, 264 μmol) was reacted with tetrahydro-2H-pyran-4-carboxylic acid (51.5 mg, 396 μmol). The product was purified by flash chromatography and eluted by ethyl acetate. The product was further purified by recrystallization with methanol and water. The white crystals were collected by filtration.

Yield: 56 mg, 135 μmol, 51% yield. Purity (H-NMR): ≥95%

$^1$H NMR (d$_6$-DMSO, 600 Mhz): ∂ 8.55 (s, 1H), 7.46-7.48 (m, 2H), 7.21 (d, J=9 Hz, 2H), 6.24 (d, J=7.8 Hz, 1H), 4.19 (d, J=13.2 Hz, 1H), 3.88 (d, J=13.8 Hz, 1H), 3.83 (m, 2H), 3.70-3.72 (m, 1H), 3.36-3.40 (m, 2H), 3.16 (t, J=12 Hz, 1H), 2.85-2.90 (m, 1H), 2.76-2.80 (m, 1H), 1.79-1.89 (m, 2H), 1.55-1.62 (m, 2H), 1.48-1.52 (m, 2H), 1.20-1.32 (m, 2H)

Example 4

Synthesis of 1-(1-(1H-pyrrole-3-carbonyl)piperidin-4-yl)-3-(4-(trifluoromethoxy)phenyl)urea

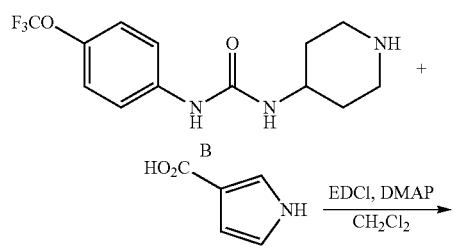

-continued

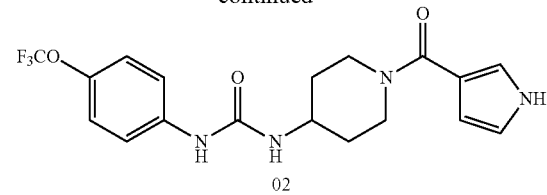

The reaction was carried out according to synthetic pathway 1, step 3. Piperidine B (80 mg, 264 μmol) was reacted with tetrahydro-2H-pyran-4-carboxylic acid (51.5 mg, 396 μmol). The product was purified by flash chromatography and eluted by ethyl acetate. The collected fraction was dried in vacuo giving white solid.

Yield: 61 mg, 154 μmol, 58.3% yield. Purity (H-NMR): ≥95%

$^1$H NMR (d$_6$-DMSO, 300 Mhz): ∂ 11.14 (s, 1H), 8.57 (s, 1H), 7.47 (d, J=9.6 Hz, 2H), 7.21 (d, J=9 Hz, 2H), 7.08 (d, J=1.2 Hz, 1H), 6.75-6.77 (m, 1H), 6.22-6.26 (m, 2H), 4.19 (d, J=13.5 Hz, 2H), 3.72-3.74 (m, 1H), 3.08-3.12 (m, 2H), 1.83-1.86 (m, 2H), 1.26-1.37 (m, 2H)

Example 5

Synthesis of 1-(1-(furan-3-carbonyl)piperidin-4-yl)-3-(4-(trifluoromethoxy)phenyl)urea

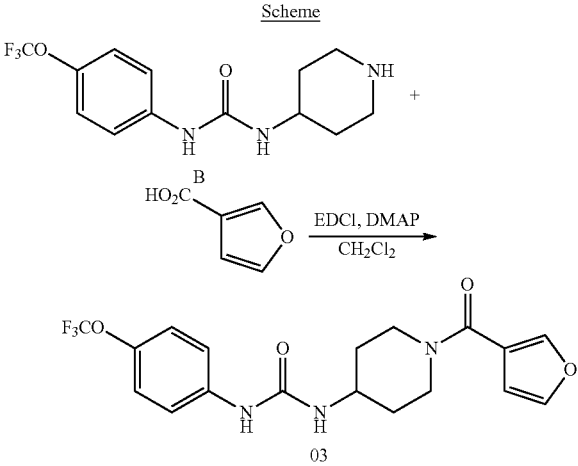

The reaction was carried out according to synthetic pathway 1, step 3. Piperidine B (80 mg, 264 μmol) was reacted with tetrahydro-2H-pyran-4-carboxylic acid (51.5 mg, 396 μmol). The product was purified by flash chromatography and eluted by ethyl acetate. The collected fraction was dried in vacuo giving white solid. The product was further purified by recrystallization using methanol and water.

Yield: 64 mg, 161 μmol, 61% yield. Purity (H-NMR): ≥95%

$^1$H NMR (d$_6$-DMSO, 300 Mhz): ∂ 8.59 (s, 1H), 8.02 (s, 1H), 7.74 (s, 1H), 7.47 (d, J=9.6 Hz, 2H), 7.21 (d, J=9 Hz, 2H), 6.65 (s, 1H), 6.26 (d, J=6.9 Hz, 2H), 3.8-4.4 (br, 2H), 3.74-3.65 (m, 1H), 2.9-3.2 (br, 2H), 1.87 (d, J=9.9 Hz, 2H), 1.29-1.40 (m, 2H)

Example 6

Synthesis of (R)-1-(1-(tetrahydrofuran-3-carbonyl)piperidin-4-yl)-3-(4-(trifluoromethoxy)phenyl)urea Scheme

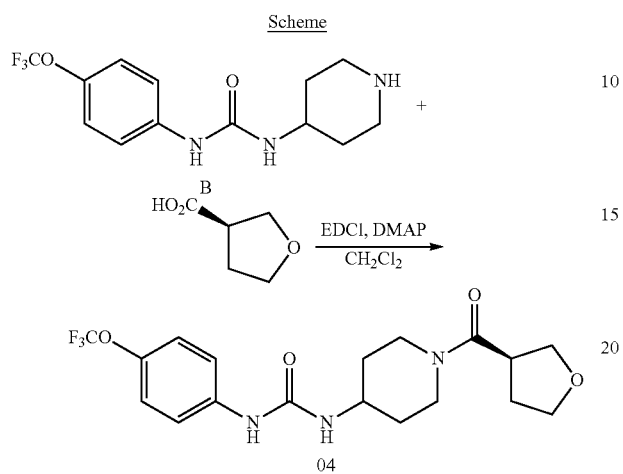

The reaction was carried out according to synthetic pathway 1, step 3. Piperidine B (80 mg, 264 μmol) was reacted with (R)-tetrahydrofuran-3-carboxylic acid (46.2 mg, 396 μmol). The product was purified by flash chromatography and eluted by ethyl acetate. The collected fraction was dried in vacuo giving white solid. The product was further purified by recrystallization using methanol and water.

Yield: 58 mg, 145 μmol, 55% yield. Purity (H-NMR): ≥95%

$^1$H NMR (d$_6$-DMSO, 300 Mhz): ∂ 8.53 (d, J=5.4 Hz, 1H), 7.47 (d, J=9.6 Hz, 2H), 7.21 (d, J=9 Hz, 2H), 6.23-6.26 (m, 1H), 4.65 (t, J=6.3 Hz, 1H), 4.05-4.10 (m, 1H), 3.89 (d, J=14.7 Hz, 1H), 3.6-3.8 (m, 3H), 3.15 (q, J=14.7 Hz, 1H), 2.81 (q, J=15.3 Hz, 1H), 1.9-2.1 (m, 2H), 1.7-1.9 (m, 4H), 1.2-1.4 (m, 2H)

Example 7

Synthesis of 1-(1-(4,5-dihydrofuran-3-carbonyl)piperidin-4-yl)-3-(4-(trifluoromethoxy)phenyl)urea Scheme

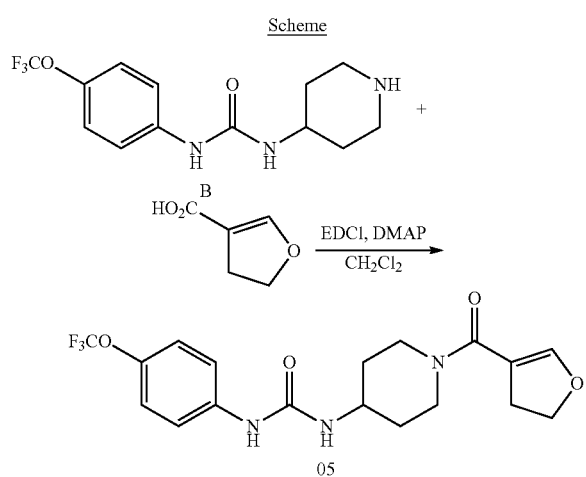

The reaction was carried out according to synthetic pathway 1, step 3. Piperidine B (80 mg, 264 μmol) was reacted with tetrahydro-2H-pyran-4-carboxylic acid (45.4 mg, 396 μmol). The product was purified by flash chromatography and eluted by ethyl acetate:hexane (8:2). The collected fraction was dried in vacuo giving white solid.

Yield: 68 mg, 170 μmol, 65% yield. Purity (H-NMR): ≥95%

$^1$H NMR (d$_6$-DMSO, 300 Mhz): ∂ 8.56 (s, 1H), 7.47 (d, J=8.7 Hz, 2H), 7.21 (d, J=8.7 Hz, 2H), 6.99 (s, 1H), 6.23 (d, J=7.8 Hz, 1H), 4.37 (t, J=9.6 Hz, 2H), 4.04 (d, J=13.5 Hz, 2H), 3.6-3.8 (m, 1H), 3.04 (t, J=11.4 Hz, 2H), 2.79 (t, J=10.5 Hz, 2H), 1.84 (d, J=9.6 Hz, 2H), 1.2-1.4 (m, 2H)

Example 8

Synthesis of 1-(1-(2-methylfuran-3-carbonyl)piperidin-4-yl)-3-(4-(trifluoromethoxy)phenyl)urea Scheme

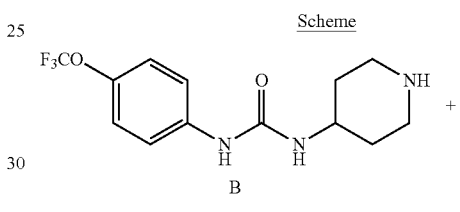

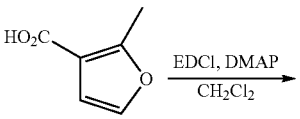

The reaction was carried out according to synthetic pathway 1, step 3. Piperidine B (80 mg, 264 μmol) was reacted with 2-methylfuran-3-carboxylic acid (50 mg, 396 μmol). The product was purified by flash chromatography and eluted by ethyl acetate:hexane (8:2). The collected fraction was dried in vacuo giving white solid. The product was further purified by recrystallization using methanol and water.

Yield: 59 mg, 144 μmol, 54% yield. Purity (H-NMR): ≥95%

$^1$H NMR (d$_6$-DMSO, 300 Mhz): ∂ 8.57 (s, 1H), 7.56 (d, J=1.8 Hz, 1H), 7.47 (d, J=8.7 Hz, 2H), 7.21 (d, J=8.7 Hz, 2H), 6.49 (d, J=1.8 Hz, 1H), 6.25 (d, J=7.5 Hz, 1H), 4.0-4.4 (br, 1H), 3.6-3.8 (m, 2H), 3.0-3.2 (m, 2H), 2.30 (s, 3H), 1.83-1.88 (m, 2H), 1.2-1.4 (m, 2H)

Example 9

Synthesis of 1-(1-(3-methylfuran-2-carbonyl)piperidin-4-yl)-3-(4-(trifluoromethoxy)phenyl)urea

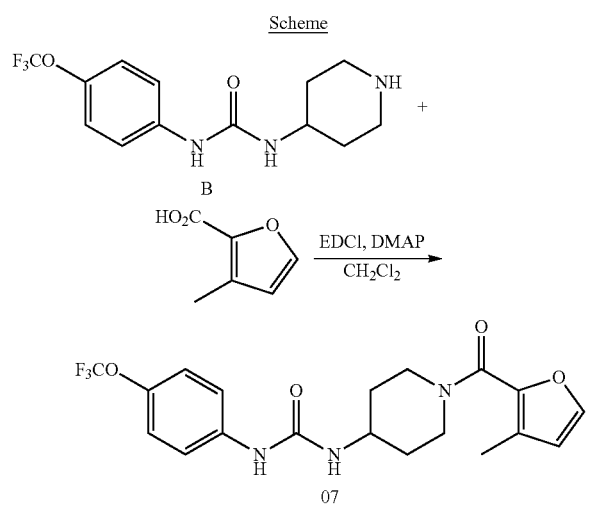

07

The reaction was carried out according to synthetic pathway 1, step 3. Piperidine B (80 mg, 264 μmol) was reacted with 3-methylfuran-2-carboxylic acid (50 mg, 396 μmol). The product was purified by flash chromatography and eluted by ethyl acetate:hexane (8:2). The collected fraction was dried in vacuo giving white solid. The product was further purified by recrystallization using methanol and water.

Yield: 53 mg, 129 μmol, 49% yield. Purity (H-NMR): ≥95%

$^1$H NMR (d$_6$-DMSO, 300 Mhz): ∂ 8.57 (s, 1H), 7.67 (s, 1H), 7.48 (d, J=9.6 Hz, 2H), 7.21 (d, J=8.7 Hz, 2H), 6.48 (s, 1H), 6.27 (d, J=7.8 Hz, 1H), 4.0-4.2 (br, 2H), 3.7-3.9 (m, 1H), 3.0-3.2 (br, 2H), 2.14 (s, 3H), 1.88 (d, J=9.3 Hz, 2H), 1.3-1.4 (m, 2H)

Example 10

Synthesis of 1-(1-(tetrahydro-2H-pyran-3-carbonyl)piperidin-4-yl)-3-(4-(trifluoromethoxy)phenyl)urea

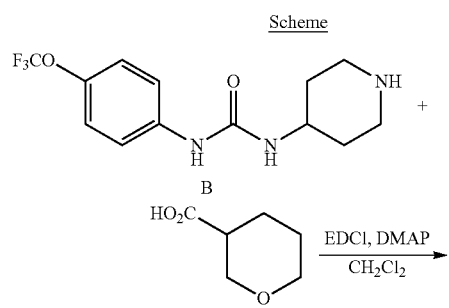

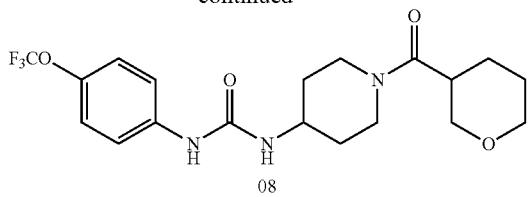

08

The reaction was carried out according to synthetic pathway 1, step 3. Piperidine B (80 mg, 264 μmol) was reacted with tetrahydro-2H-pyran-3-carboxylic acid (50 mg, 396 μmol). The product was purified by flash chromatography and eluted by ethyl acetate. The collected fraction was dried in vacuo giving white solid. The product was further purified by recrystallization using methanol and water.

Yield: 43 mg, 104 μmol, 39% yield. Purity (H-NMR): ≥95%

$^1$H NMR (d$_6$-DMSO, 300 Mhz): ∂ 8.55 (s, 1H), 7.47 (d, J=9.3 Hz, 2H), 7.21 (d, J=8.7 Hz, 2H), 6.23 (d, J=7.8 Hz, 1H), 4.1-4.2 (m, 1H), 3.6-3.9 (m, 4H), 3.1-3.4 (m, 3H), 2.7-2.9 (m, 2H), 1.7-1.9 (m, 3H), 1.5-1.7 (m, 3H), 1.1-1.4 (m, 2H)

Example 11

Synthesis of 1-(1-(tetrahydro-2H-pyran-4-carbonyl)piperidin-4-yl)-3-(4-(trifluoromethyl)phenyl)urea

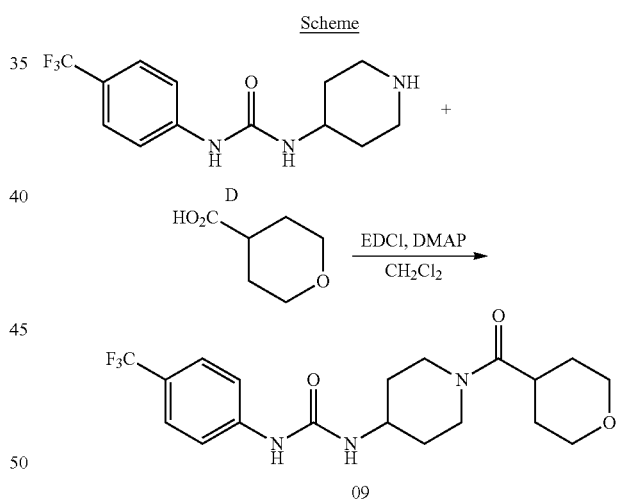

09

The reaction was carried out according to synthetic pathway 1, step 3. Piperidine D (47 mg, 164 μmol) was reacted with tetrahydro-2H-pyran-4-carboxylic acid (32 mg, 245 μmol). The product was purified by flash chromatography and eluted by ethyl acetate. The product was further purified by recrystallization with methanol and water. The white crystals were collected by filtration.

Yield: 50 mg, 125 μmol, 76.8% yield. Purity (H-NMR): ≥95%

$^1$H NMR (d$_6$-DMSO, 300 Mhz): ∂ 8.78 (s, 1H), 7.57 (s, 4H), 6.34 (d, J=7.5 Hz, 1H), 4.19 (d, J=12.3 Hz, 1H), 3.8-3.9 (m, 3H), 3.7-3.8 (m, 1H), 3.38 (t, J=11.4 Hz, 3H), 3.18 (t, J=9.9 Hz, 1H), 2.7-2.9 (m, 2H), 1.7-1.9 (m, 2H), 1.4-1.7 (m, 2H), 1.1-1.4 (m, 2H)

Example 12

Synthesis of 1-(1-(furan-3-carbonyl)piperidin-4-yl)-3-(4-(trifluoromethyl)phenyl)urea

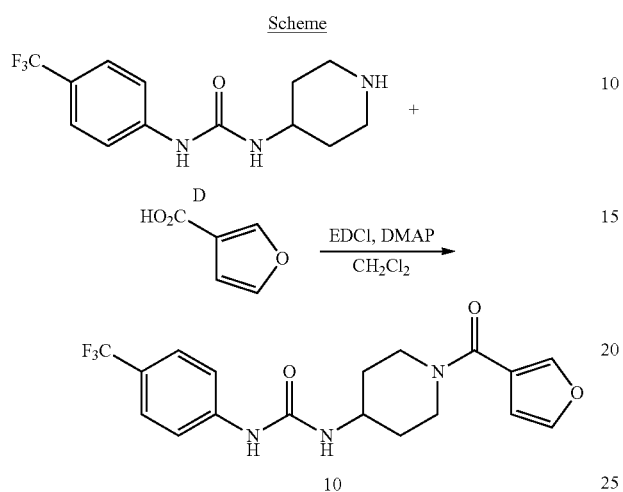

The reaction was carried out according to synthetic pathway 1, step 3. Piperidine D (47 mg, 164 μmol) was reacted with furan-3-carboxylic acid (32 mg, 245 μmol). The product was purified by flash chromatography and eluted by ethyl acetate:hexane (8:2). The product was further purified by recrystallization with methanol and water. The white crystals were collected by filtration.

Yield: 43 mg, 113 μmol, 69% yield. Purity (H-NMR): ≥95%

$^1$H NMR (d$_6$-DMSO, 300 Mhz): ∂ 8.81 (s, 1H), 8.03 (s, 1H), 7.74 (s, 1H), 7.57 (s, 4H), 6.65 (s, 1H), 6.36 (d, J=7.8 Hz, 1H), 3.8-4.4 (br, 2H), 3.7-3.9 (m, 1H), 3.0-3.4 (br, 2H), 1.87 (d, J=11.7 Hz, 2H), 1.3-1.5 (m, 2H)

Example 13

Synthesis of (R)-1-(1-(tetrahydrofuran-3-carbonyl)piperidin-4-yl)-3-(4-(trifluoromethyl)phenyl)urea

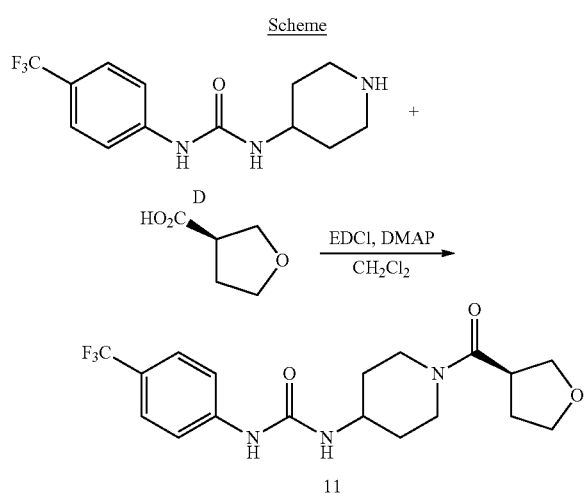

The reaction was carried out according to synthetic pathway 1, step 3. Piperidine D (47 mg, 164 μmol) was reacted with (R)-tetrahydrofuran-3-carboxylic acid (28.7 mg, 245 μmol). The product was purified by flash chromatography and eluted by ethyl acetate. The collected fraction was dried in vacuo giving white solid.

Yield: 42 mg, 109 μmol, 66.9% yield. Purity (H-NMR): ≥95%

$^1$H NMR (d$_6$-DMSO, 300 Mhz): ∂ 8.76 (d, J=4.8 Hz, 1H), 7.57 (s, 4H), 6.36 (d, J=4.2 Hz, 1H), 4.66 (t, J=6.3 Hz, 2H), 4.14 (t, J=13.2 Hz, 1H), 3.96 (d, J=15.9 Hz, 1H), 3.6-3.8 (m, 3H), 3.15 (q, J=14.4 Hz, 1H), 2.82 (d, J=12.3 Hz, 1H), 1.9-2.1 (m, 2H), 1.7-1.9 (m, 4H), 1.2-1.5 (m, 2H)

Example 14

Synthesis of 1-(1-(4,5-dihydrofuran-3-carbonyl)piperidin-4-yl)-3-(4-(trifluoromethyl)phenyl)urea

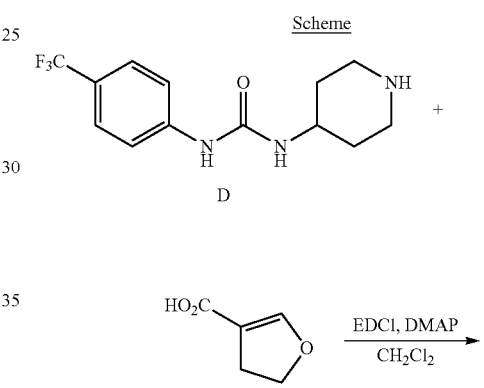

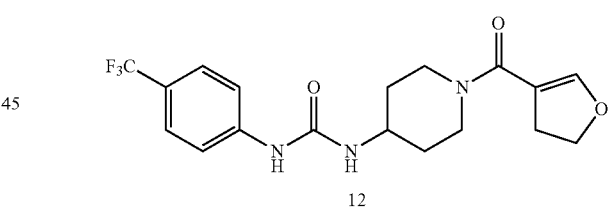

The reaction was carried out according to synthetic pathway 1, step 3. Piperidine D (47 mg, 164 μmol) was reacted with 4,5-dihydrofuran-3-carboxylic acid (28.4 mg, 245 μmol). The product was purified by flash chromatography and eluted by ethyl acetate. The collected fractions were dried in vacuo giving white solid.

Yield: 45 mg, 117 μmol, 72.1% yield. Purity (H-NMR): ≥95%

$^1$H NMR (d$_6$-DMSO, 300 Mhz): ∂ 8.78 (s, 1H), 7.57 (s, 4H), 6.99 (s, 1H), 6.34 (d, J=7.5 Hz, 1H), 4.37 (t, J=9.6 Hz, 2H), 4.05 (d, J=13.5 Hz, 2H), 3.6-3.8 (m, 1H), 3.04 (t, J=11.1 Hz, 2H), 2.79 (t, J=9.6 Hz, 2H), 1.85 (d, J=10.5, 2H), 1.2-1.4 (m, 2H)

Example 15

Synthesis of 1-(1-(2-methylfuran-3-carbonyl)piperidin-4-yl)-3-(4-(trifluoromethyl)phenyl)urea Scheme

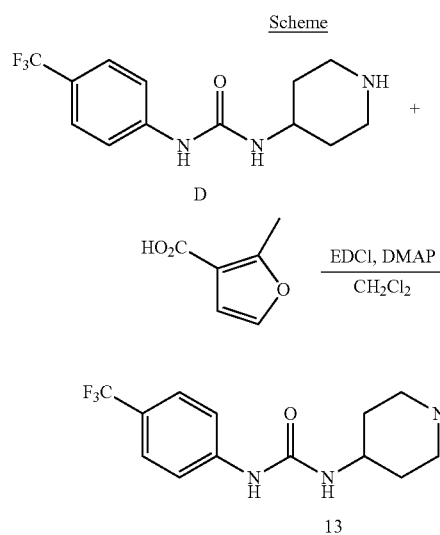

13

The reaction was carried out according to synthetic pathway 1, step 3. Piperidine D (47 mg, 164 µmol) was reacted with 2-methylfuran-3-carboxylic acid (30 mg, 245 µmol). The product was purified by flash chromatography and eluted by ethyl acetate:hexane (8:2). The product was further purified by recrystallization with methanol and water. The white crystals were collected by filtration.

Yield: 48 mg, 121 µmol, 74.5% yield. Purity (H-NMR): ≥95%

$^1$H NMR (d$_6$-DMSO, 300 Mhz): ∂ 8.80 (s, 1H), 7.57 (s, 4H), 6.48 (d, J=1.8 Hz, 1H), 6.35 (d, J=7.8 Hz, 1H), 4.0-4.3 (br, 2H), 3.6-3.9 (m, 1H), 3.0-3.2 (br, 2H), 2.30 (s, 3H), 1.85 (d, J=10.5, 2H), 1.2-1.4 (m, 2H)

Example 16

Synthesis of 1-(1-(3-methylfuran-2-carbonyl)piperidin-4-yl)-3-(4-(trifluoromethyl)phenyl)urea Scheme

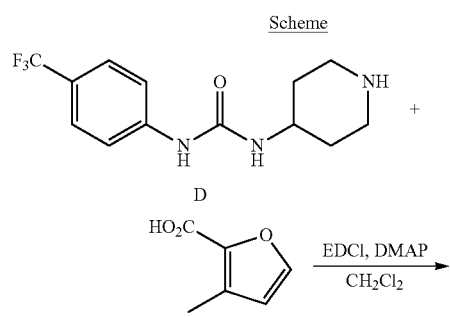

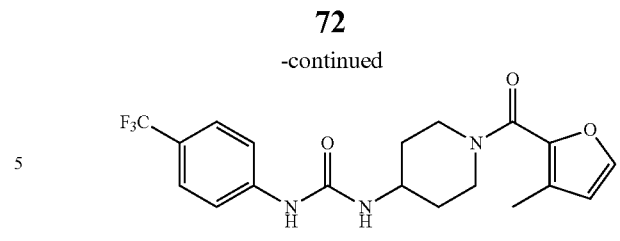

14

The reaction was carried out according to synthetic pathway 1, step 3. Piperidine D (47 mg, 164 µmol) was reacted with 3-methylfuran-2-carboxylic acid (30 mg, 245 µmol). The product was purified by flash chromatography and eluted by ethyl acetate:hexane (8:2). The product was further purified by recrystallization with methanol and water. The white crystals were collected by filtration.

Yield: 45 mg, 114 µmol, 69.9% yield. Purity (H-NMR): ≥95%

$^1$H NMR (d$_6$-DMSO, 300 Mhz): ∂ 8.80 (s, 1H), 7.67 (s, 1H), 7.57 (s, 4H), 6.48 (s, 1H), 6.38 (d, J=7.5 Hz, 1H), 3.9-4.2 (br, 2H), 3.7-3.9 (m, 1H), 3.0-3.2 (br, 2H), 2.14 (s, 3H), 1.89 (d, J=9.9, 2H), 1.3-1.5 (m, 2H)

Example 17

Synthesis of 1-(1-(tetrahydro-2H-pyran-3-carbonyl)piperidin-4-yl)-3-(4-(trifluoromethyl)phenyl)urea Scheme

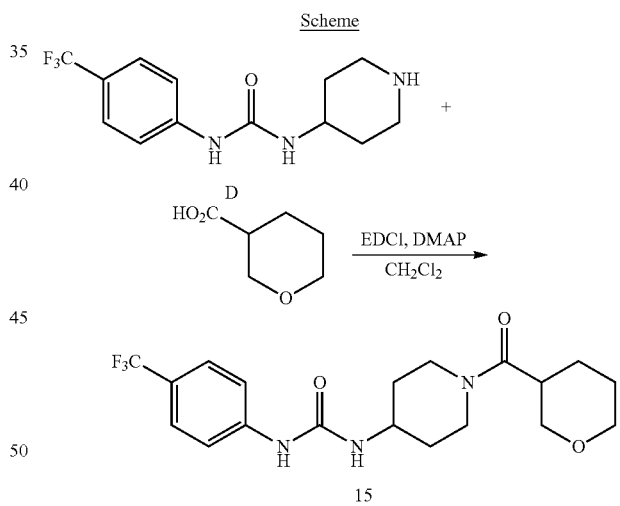

15

The reaction was carried out according to synthetic pathway 1, step 3. Piperidine D (47 mg, 164 µmol) was reacted with tetrahydro-2H-pyran-3-carboxylic acid (32.4 mg, 245 µmol). The product was purified by flash chromatography and eluted by ethyl acetate. The product was further purified by recrystallization with methanol and water. The white crystals were collected by filtration.

Yield: 42 mg, 105 µmol, 64.6% yield. Purity (H-NMR): ≥95%

$^1$H NMR (d$_6$-DMSO, 300 Mhz): ∂ 8.78 (s, 1H), 7.57 (s, 4H), 6.38 (d, J=7.5 Hz, 1H), 4.16 (d, J=12.6 Hz, 1H), 3.6-3.9 (m, 4H), 3.1-3.3 (m, 3H), 2.7-2.9 (m, 2H), 1.7-1.9 (m, 3H), 1.5-1.7 (m, 3H), 1.2-1.4 (m, 2H)

Example 18

Synthesis of 1-(1-(1H-pyrrole-3-carbonyl)piperidin-4-yl)-3-(4-(trifluoromethyl)phenyl)urea

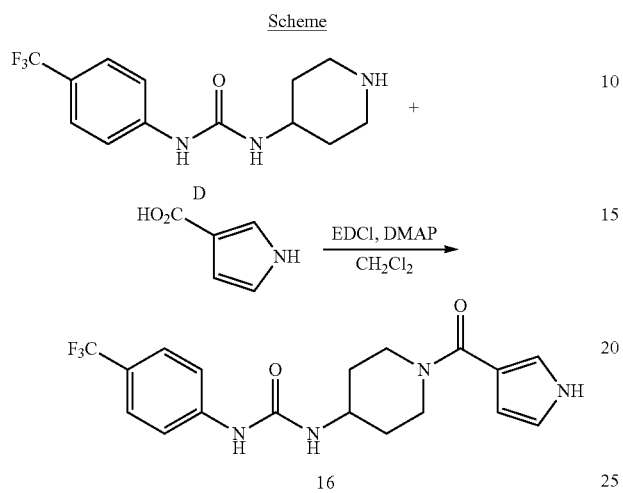

The reaction was carried out according to synthetic pathway 1, step 3. Piperidine D (47 mg, 164 µmol) was reacted with 1H-pyrrole-3-carboxylic acid (27.2 mg, 245 µmol). The product was purified by flash chromatography and eluted by ethyl acetate. The collected fractions were dried in vacuo giving white solid.

Yield: 52 mg, 137 µmol, 83.9% yield. Purity (H-NMR): ≥95%

$^1$H NMR (d$_6$-DMSO, 300 Mhz): ∂ 8.79 (s, 1H), 7.57 (s, 4H), 7.08 (s, 1H), 6.76 (d, J=1.8 Hz, m), 6.34 (d, J=7.8 Hz, 1H), 6.22 (s, 1H), 4.18 (d, J=13.5 Hz, 1H), 3.7-3.9 (m, 1H), 3.09 (t, J=10.2 Hz, 2H), 1.86 (d, J=9.9 Hz, 2H), 1.2-1.4 (m, 2H)

Example 19

Synthesis of 1-(1-(tetrahydrofuran-3-carbonyl)piperidin-4-yl)-3-(4-(trifluoromethoxy)phenyl)urea

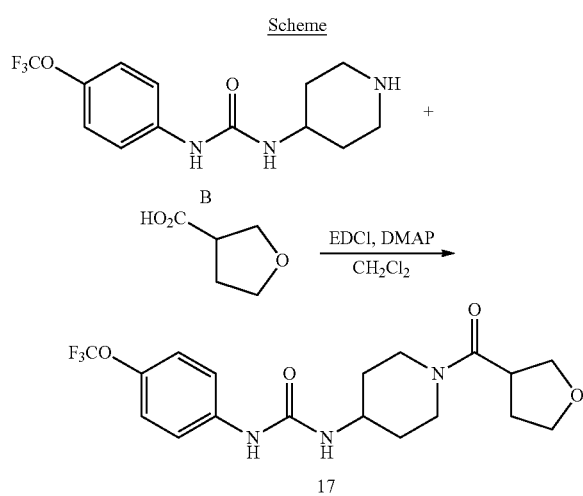

The reaction was carried out according to synthetic pathway 1, step 3. Piperidine B (80 mg, 264 µmol) was reacted with 2-methylfuran-3-carboxylic acid (61 mg, 528 µmol). The product was purified by flash chromatography and eluted by ethyl acetate. The collected fraction was dried in vacuo giving white solid. The product was further purified by recrystallization using methanol and water.

Yield: 59 mg, 144 µmol, 54% yield. Purity (H-NMR): ≥95%

$^1$H NMR (d$_6$-DMSO, 300 Mhz): ∂ 8.55 (s, 1H), 7.47 (d, J=9.3 Hz, 2H), 7.21 (d, J=8.7 Hz, 2H), 6.23 (d, J=7.2 Hz, 1H), 4.18 (d, J=12.9 Hz, 1H), 3.8-3.9 (m, 2H), 3.6-3.8 (m, 3H), 3.3-3.4 (m, 1H), 3.1-3.3 (m, 1H), 2.82 (t, J=12 Hz, 2H), 1.9-2.1 (m, 2H), 1.84 (t, J=12.9 Hz, 2H), 1.2-1.4 (m, 2H).

Example 20

Synthesis of 1-(1-(tetrahydrofuran-3-carbonyl)piperidin-4-yl)-3-(4-(trifluoromethyl)phenyl)urea

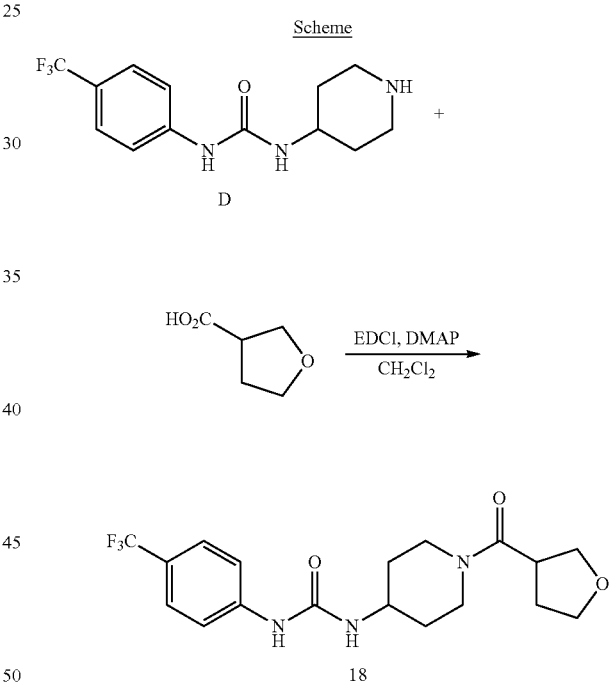

The reaction was carried out according to synthetic pathway 1, step 3. Piperidine D (80 mg, 278 µmol) was reacted with 2-methylfuran-3-carboxylic acid (65 mg, 556 µmol). The product was purified by flash chromatography and eluted by ethyl acetate. The collected fraction was dried in vacuo giving white solid. The product was further purified by recrystallization using methanol and water.

Yield: 64 mg, 166 µmol, 60% yield. Purity (H-NMR): ≥95%

$^1$H NMR (d$_6$-DMSO, 300 Mhz): ∂ 8.78 (s, 1H), 7.57 (s, 4H), 6.33 (d, J=6.9 Hz, 1H), 4.19 (d, J=13.5 Hz, 1H), 3.8-3.9 (m, 2H), 3.6-3.8 (m, 4H), 3.3-3.4 (m, 1H), 3.1-3.3 (m, 1H), 2.83 (t, J=12 Hz, 1H), 1.9-2.1 (m, 2H), 1.84 (t, J=13.8 Hz, 2H), 1.2-1.4 (m, 2H)

Example 21

Synthesis of 1-(3-fluoro-4-(trifluoromethoxy)phenyl)-3-(1-isobutyrylpiperidin-4-yl)urea

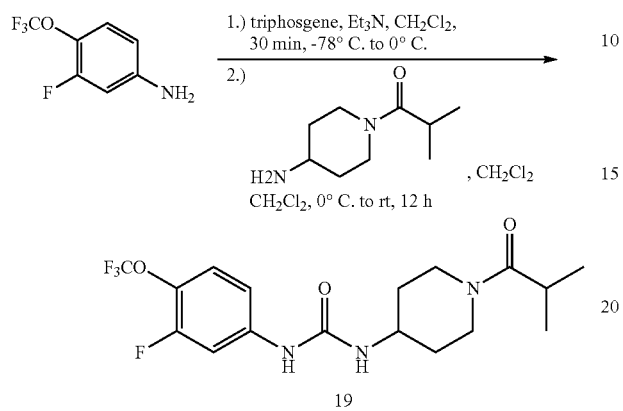

The reaction was carried out according to synthetic pathway 2. The 3-fluoro-4-(trifluoromethoxy)aniline (109 mg, 559 µmol) was reacted with 1-(4-aminopiperidin-1-yl)-2-methylpropan-1-one (143 mg, 838 µmol). The product was purified by flash chromatography using ethyl acetate:hexane (7:3). The product was further purified by recrystallization using methanol and water.

Yield: 150 mg, 383 µmol, 68.6% yield. Purity (H-NMR): ≥95%

$^1$H NMR (d$_6$-DMSO, 600 Mhz): ∂ 8.78 (s, 1H), 7.67 (dd, J=13.89 Hz, 1.2 Hz, 1H), 7.38 (t, J=9.6 Hz, 1H), 7.12 (d, J=9.6 Hz, 1H), 6.35 (d, J=13.8 Hz, 1H), 4.20 (d, J=13.2 Hz, 1H), 3.84 (d, J=13.8 Hz, 1H), 3.7-3.8 (m, 1H), 3.15 (t, J=12 Hz, 1H), 2.8-2.9 (m, 1H), 2.77 (t, J=11.4 Hz, 1H), 1.86 (d, J=10.8 Hz, 1H), 1.79 (d, J=11.4 Hz, 1H), 1.2-1.4 (m, 2H), 0.98 (t, J=7.8 Hz, 6H)

Example 22

Synthesis of 1-(3-fluoro-4-(trifluoromethyl)phenyl)-3-(1-isobutyrylpiperidin-4-yl)urea

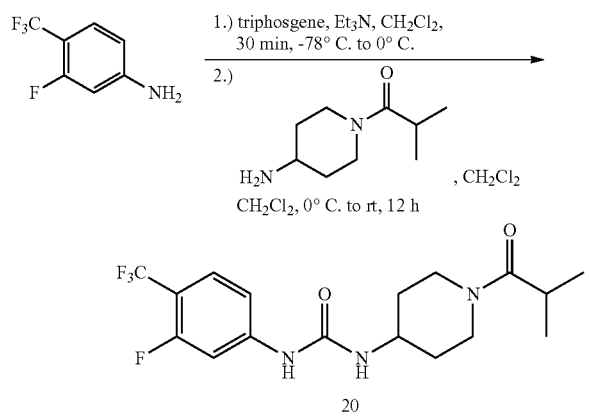

The reaction was carried out according to synthetic pathway 2. The 3-fluoro-4-(trifluoromethoxy)aniline (100 mg, 558 µmol) was reacted with 1-(4-aminopiperidin-1-yl)-2-methylpropan-1-one (142 mg, 838 µmol). The product was purified by flash chromatography using ethyl acetate:hexane (7:3). The product was further purified by recrystallization using methanol and water.

Yield: 120 mg, 320 µmol, 68.6% yield. Purity (H-NMR): ≥95%

$^1$H NMR (d$_6$-DMSO, 300 Mhz): ∂ 9.02 (s, 1H), 7.66 (d, J=14.7 Hz, 1H), 7.58 (t, J=8.7 Hz, 1H), 7.20 (d, J=8.7 Hz, 1H), 6.46 (d, J=7.5 Hz, 1H), 4.20 (d, J=12.9 Hz, 1H), 3.85 (d, J=13.5 Hz, 1H), 3.6-3.8 (m, 1H), 3.16 (t, J=12 Hz, 1H), 2.8-2.95 (m, 1H), 2.77 (t, J=11.4 Hz, 1H), 1.83 (t, J=14.1 Hz, 2H), 1.2-1.4 (m, 2H), 0.98 (d, J=5.7 Hz, 6H)

Example 23

Synthesis of N-(3-fluoro-4-(trifluoromethoxy)phenyl)-2-(1-isobutyrylpiperidin-4-yl)acetamide

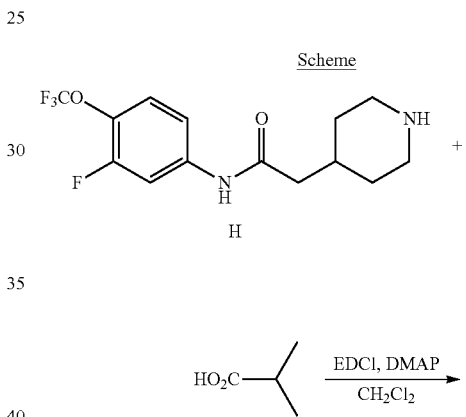

The reaction was carried out according to synthetic pathway 1, step 3. Piperidine H (38 mg, 118 µmol) was reacted with isbutyric acid (12.3 mg, 142.9 µmol). The product was purified by flash chromatography and eluted by ethyl acetate. The collected fraction was dried in vacuo giving white solid.

Yield: 120 mg, 320 µmol, 68.6% yield. Purity (H-NMR): ≥95%

$^1$H NMR (d$_6$-DMSO, 300 Mhz): ∂ 10.28 (s, 1H), 7.85 (dd, J=12.9 Hz, 1.8 Hz, 1H), 7.49 (t, J=9 Hz, 1H), 7.36 (d, J=9.6 Hz, 1H), 4.36 (d, J=12.6 Hz, 1H), 3.91 (d, J=12.9 Hz, 1H), 3.00 (t, J=11.7 Hz, 1H), 2.7-2.9 (m, 1H), 2.5-2.6 (m, 1H), 2.27 (d, J=6.9 Hz, 2H), 1.9-2.1 (m, 1H), 1.70 (t, J=14.4 Hz, 2H), 1.1-1.2 (m, 2H), 0.98 (s, 6H)

Example 24

Synthesis of 2-(1-(2-oxo-2-(4-(3-(4-(trifluoromethyl)phenyl) ureido)piperidin-1-yl)ethyl)cyclohexyl)acetic acid

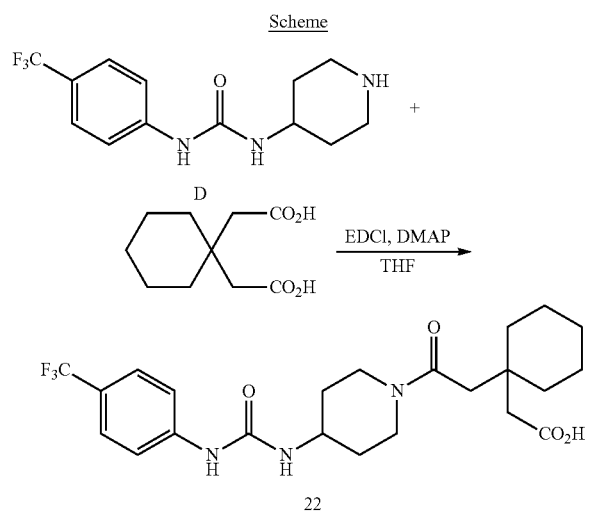

2,2'-(cyclohexane-1,1-diyl)diacetic acid (35 mg, 175 µmol), EDCI (30 mg, 157 µmol) and DMAP (21.2 mg, 157 µmol) were dissolved in THF (20 mL) and piperidine D (75 mg, 261 µmol) suspended in THF (4 mL) was added to the reaction mixture at rt. The reaction mixture was stirred at rt for 12 h and was quenched by addition of HCl solution (1M). The organic layer was collected and the aqueous layer was further extracted by ethyl acetate for three times. The combined organic layers were dried in vacuo and was purified by flash chromatography using 1% methanol in ethyl acetate and monitored by TLC. The collected fractions were combined and dried in vacuo giving a final white precipitates.

Yield: 15 mg, 31.9 µmol, 18.3% yield. Purity (H-NMR): ≥95%

$^1$H NMR (d$_6$-DMSO, 300 Mhz): ∂ 8.75 (s, 1H), 7.56 (s, 4H), 6.35 (d, J=7.8 Hz, 1H), 4.2-4.3 (m, 1H), 3.92 (d, J=12.9 Hz, 1H), 3.6-3.8 (m, 1H), 3.14 (t, J=11.4 Hz, 1H), 2.7-2.9 (m, 1H), 2.55 (s, 2H), 1.7-1.9 (m, 2H), 1.5-1.7 (br, 2H), 1.2-1.5 (m, 6H)

Melting Point (° C.): 171.8-176.7

Example 25

Synthesis of 1-(3-fluoro-4-(trifluoromethoxy)phenyl)-3-(1-propionylpiperidin-4-yl)urea

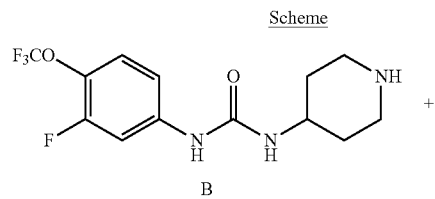

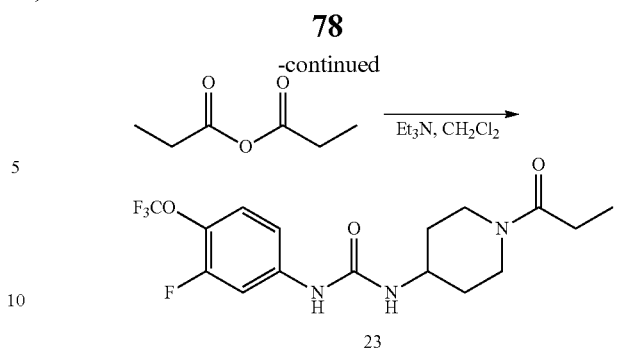

To the suspension of piperidine B (30 mg, 93.5 µmol) and triethylamine (141 mg, 141.7 µmol), propionic anhydride (18.2 mg, 141.7 µmol) was added dropwise. The reaction was stirred at rt for 12 h and was quenched by addition of silica gel (50 mg). The slurry was dried in vacuo and was applied to flash chromatography. The product was eluted by ethyl acetate:hexane (9:1) and monitored by TLC. The collected fractions were dried in vacuo and were recrystallized by methanol and water. The final white crystal was collected by filtration.

Yield: 33 mg, 87.5 µmol, 93% yield. Purity (H-NMR): ≥95%

$^1$H NMR (d$_6$-DMSO, 300 Mhz): ∂ 8.77 (s, 1H), 7.66 (dd, J=13.5 Hz, 2.4 Hz, 1H), 7.39 (t, J=9 Hz, 1H), 7.10 (d, J=9 Hz, 1H), 6.34 (d, J=7.5 Hz, 1H), 4.18 (d, J=12.9 Hz, 1H), 3.6-3.8 (m, 2H), 3.12 (t, J=11.7 Hz, 1H), 2.77 (t, J=11.7 Hz, 1H), 2.31 (q, J=7.5, 2H), 1.82 (d, J=12.3 Hz, 1H), 1.2-1.4 (m, 2H), 0.98 (t, J=7.5 Hz, 6H)

Example 26

Synthesis of 1-(1-(cyclopropanecarbonyl)piperidin-4-yl)-3-(4-(trifluoromethoxy)phenyl)urea

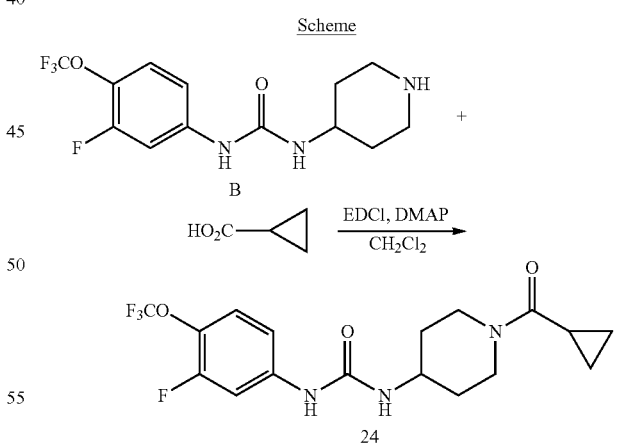

The reaction was carried out according to synthetic pathway 1, step 3. Piperidine B (30 mg, 93.4 µmol) was reacted with cyclopropanecarboxylic acid (12 mg, 140 µmol). The product was purified by flash chromatography and eluted by ethyl acetate:hexane (9:1). The collected fraction was dried in vacuo giving white solid. The product was further purified by recrystallization using methanol and water.

Yield: 31 mg, 93.4 µmol, 85% yield. Purity (H-NMR): ≥95%

$^1$H NMR (d$_6$-DMSO, 300 Mhz): ∂ 8.78 (s, 1H), 7.66 (d, J=13.5 Hz, 1H), 7.39 (t, J=9 Hz, 1H), 7.11 (d, J=8.7 Hz, 1H), 6.36 (d, J=7.8 Hz, 1H), 4.16 (br, 2H), 3.6-3.8 (m, 1H), 3.2-3.3 (m, 1H), 2.7-2.9 (m, 1H), 1.7-2.0 (m, 3H), 1.1-1.4 (m, 2H), 0.6-0.8 (m, 4H)

Example 27

Synthesis of (R)-1-(3-fluoro-4-(trifluoromethoxy)phenyl)-3-(1-(tetrahydrofuran-3-carbonyl)piperidin-4-yl)urea

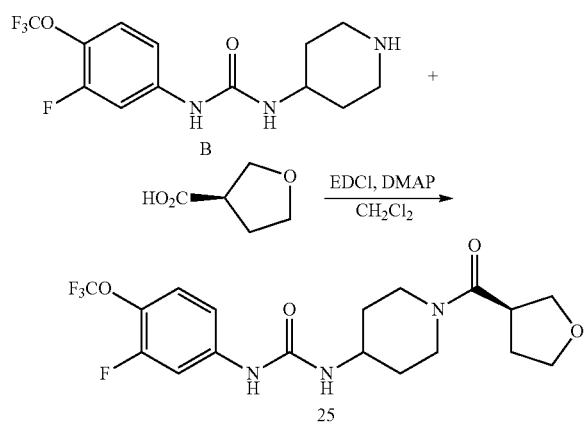

The reaction was carried out according to synthetic pathway 1, step 3. Piperidine B (30 mg, 93.4 μmol) was reacted with (R)-tetrahydrofuran-3-carboxylic acid (16 mg, 140 μmol). The product was purified by flash chromatography and eluted by ethyl acetate. The collected fraction was dried in vacuo giving white solid. The product was further purified by recrystallization using methanol and water (32 mg, 76.3 μmol, 81.7% yield).

Yield: 32 mg, 76.3 μmol, 81.7% yield. Purity (H-NMR): ≥95%

$^1$H NMR (d$_6$-DMSO, 300 Mhz): ∂ 8.79 (s, 1H), 7.66 (dd, J=13.8 Hz, 2.4 Hz, 1H), 7.39 (t, J=8.7 Hz, 1H), 7.11 (d, J=9 Hz, 1H), 6.35 (d, J=7.8 Hz, 1H), 4.18 (d, J=12.9 Hz, 1H), 3.8-3.9 (m, 2H), 3.6-3.8 (m, 4H), 3.3-3.4 (m, 1H), 3.1-3.2 (m, 1H), 2.81 (t, J=12 Hz, 1H), 1.9-2.1 (m, 2H), 1.7-1.9 (m, 2H), 1.1-1.4 (m, 2H)

Example 28

Synthesis of (S)-1-(3-fluoro-4-(trifluoromethoxy)phenyl)-3-(1-(2-methylbutanoyl)piperidin-4-yl)urea

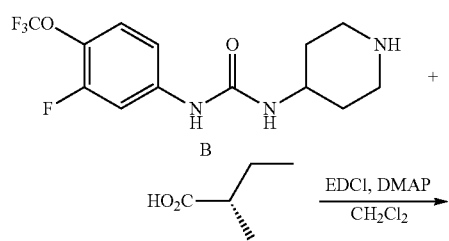

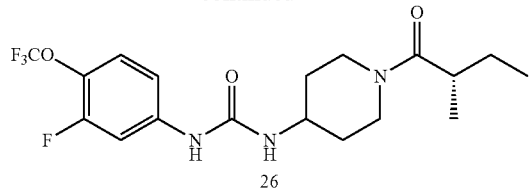

The reaction was carried out according to synthetic pathway 1, step 3. Piperidine B (30 mg, 93.4 μmol) was reacted with (S)-2-methylbutanoic acid (14 mg, 140 μmol). The product was purified by flash chromatography and eluted by ethyl acetate. The collected fraction was dried in vacuo giving white solid. The product was further purified by recrystallization using methanol and water (30 mg, 83.9 μmol, 79.2% yield).

Yield: 30 mg, 83.9 μmol, 79.2% yield. Purity (H-NMR): ≥95%

$^1$H NMR (d$_6$-DMSO, 600 Mhz): ∂ 8.78 (d, J=17.4 Hz, 1H), 7.66 (dd, J=13.8 Hz, 2.4 Hz, 1H), 7.39 (t, J=9 Hz, 1H), 7.11 (dd, J=9 Hz, 1.2 Hz, 1H), 6.3-6.4 (m, 1H), 4.23 (t, J=13.2 Hz, 1H), 3.88 (d, J=10.8 Hz, 1H), 3.6-3.8 (m, 1H), 3.1-3.2 (m, 1H), 2.6-2.8 (m, 2H), 1.8-1.9 (br, 1H), 1.7-1.8 (m, 1H), 1.5-1.6 (m, 1H), 1.1-1.4 (m, 3H), 0.9-1.0 (m, 3H), 0.7-0.9 (m, 3H)

Example 29

Synthesis of (R)-1-(3-fluoro-4-(trifluoromethoxy)phenyl)-3-(1-(tetrahydrofuran-3-carbonyl)piperidin-4-yl)urea

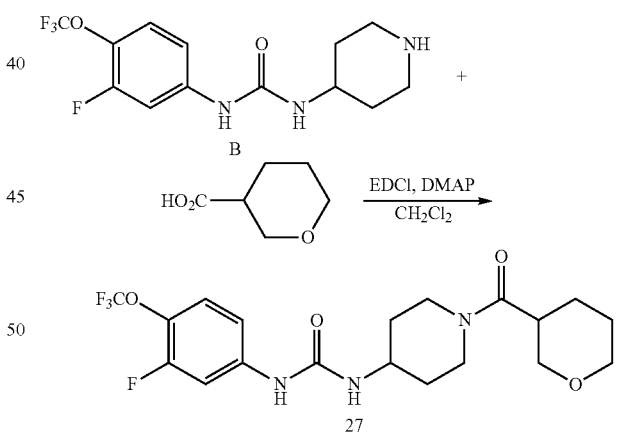

The reaction was carried out according to synthetic pathway 1, step 3. Piperidine B (30 mg, 93.4 μmol) was reacted with tetrahydro-2H-pyran-3-carboxylic acid (18 mg, 140 μmol). The product was purified by flash chromatography and eluted by ethyl acetate. The collected fraction was dried in vacuo giving white solid. The product was further purified by recrystallization using methanol and water.

Yield: 34 mg, 78.4 μmol, 84% yield. Purity (H-NMR): ≥95%

$^1$H NMR (d$_6$-DMSO, 300 Mhz): ∂ 8.78 (s, 1H), 7.66 (dd, J=13.5 Hz, 2.4 Hz, 1H), 7.39 (t, J=8.7 Hz, 1H), 7.11 (d, J=9 Hz, 1H), 6.34 (d, J=7.5 Hz, 1H), 4.16 (d, J=11.4 Hz, 1H), 3.6-4.0 (m, 4H), 3.1-3.3 (m, 2H), 2.7-2.9 (m, 2H), 1.7-1.9 (m, 3H), 1.5-1.6 (m, 3H), 1.1-1.4 (m, 3H)

Example 30

Synthesis of 1-(4-(trifluoromethoxy)phenyl)-3-(1-(1-(trifluoromethyl)cyclopropane-1-carbonyl)piperidin-4-yl)urea

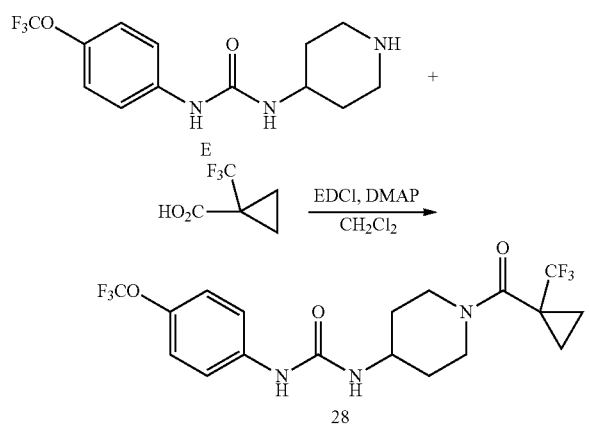

The reaction was carried out according to synthetic pathway 1, step 3. Piperidine E (50 mg, 165.0 μmol) was reacted with 1-(trifluoromethyl)cyclopropane-1-carboxylic acid (30.5 mg, 198 μmol). The product was purified by flash chromatography and eluted by ethyl acetate:hexane (4:1). The collected fraction was dried in vacuo giving white solid. The product was further purified by recrystallization using methanol and water.

Yield: 60 mg, 142 μmol, 71.6% yield. Purity (H-NMR): ≥95%

$^1$H NMR (d$_6$-DMSO, 300 Mhz): ∂ 8.78 (s, 1H), 7.57 (s, 4H), 6.36 (d, J=7.8 Hz, 1H), 4.10 (d, J=12.9 Hz, 2H), 3.6-3.8 (m, 1H), 2.9-3.2 (br, 2H), 1.87 (d, J=9.3 Hz, 2H), 1.2-1.4 (m, 4H), 1.1-1.2 (s, 2H)

Example 31

Synthesis of 1-(3-fluoro-4-(trifluoromethoxy)phenyl)-3-(1-(tetrahydro-2H-pyran-4-carbonyl)piperidin-4-yl)urea

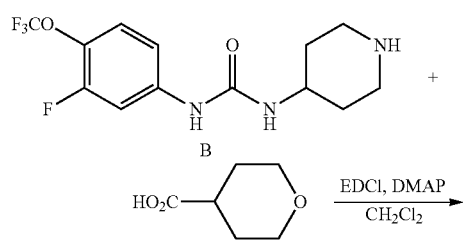

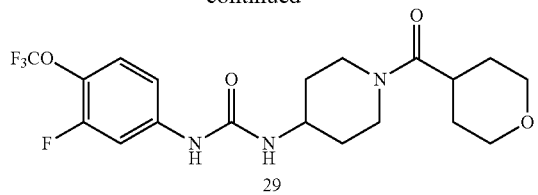

The reaction was carried out according to synthetic pathway 1, step 3. Piperidine B (60 mg, 186.9 μmol) was reacted with tetrahydrofuran-2H-pyran-4-carboxylic acid (48.6 mg, 373.8 μmol). The product was purified by flash chromatography and eluted by ethyl acetate. The collected fraction was dried in vacuo giving white solid. The product was further purified by recrystallization using methanol and water.

Yield: 58 mg, 134 μmol, 71.6% yield. Purity (H-NMR): ≥95%

$^1$H NMR (d$_6$-DMSO, 600 Mhz): ∂ 8.78 (s, 1H), 7.67 (dd, J=13.2 Hz, 2.4 Hz, 1H), 7.37 (t, J=9 Hz, 1H), 7.11 (d, J=9.6 Hz, 1H), 6.35 (d, J=7.2 Hz, 1H), 4.20 (d, J=13.2 Hz, 1H), 3.8-3.9 (m, 3H), 3.7-3.8 (m, 1H), 3.3-3.4 (m, 2H), 3.16 (t, J=12 Hz, 1H), 2.8-2.9 (m, 1H), 2.7-2.9 (m, 1H), 1.7-1.9 (m, 2H), 1.5-1.7 (m, 2H), 1.4-1.5 (m, 2H), 1.2-1.4 (m, 2H)

Example 32

Synthesis of 1-(3-fluoro-4-(trifluoromethoxy)phenyl)-3-(1-(tetrahydro-2H-pyran-4-carbonyl)piperidin-4-yl)urea

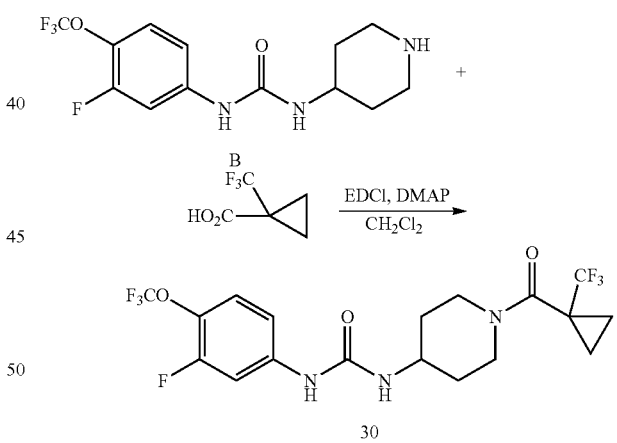

The reaction was carried out according to synthetic pathway 1, step 3. Piperidine B (60 mg, 186.9 μmol) was reacted with 1-(trifluoromethyl)cyclopropane-1-carboxylic acid (57.6 mg, 373.8 μmol). The product was purified by flash chromatography and eluted by ethyl acetate. The collected fraction was dried in vacuo giving white solid. The product was further purified by recrystallization using methanol and water.

Yield: 60 mg, 131 μmol, 70.2% yield. Purity (H-NMR): ≥95%

$^1$H NMR (d$_6$-DMSO, 300 Mhz): ∂ 8.78 (s, 1H), 7.67 (dd, J=13.2 Hz, 2.1 Hz, 1H), 7.39 (t, J=9 Hz, 1H), 7.11 (d, J=8.7 Hz, 1H), 6.37 (d, J=7.5 Hz, 1H), 4.10 (d, J=13.2 Hz, 1H), 3.6-3.8 (m, 1H), 3.0-3.2 (br, 1H), 1.86 (d, J=11.7 Hz, 2H), 1.2-1.4 (m, 4H), 1.1-1.2 (s, 2H)

Example 33

Synthesis of 1-(3-fluoro-4-(trifluoromethyl)phenyl)-3-(1-propionylpiperidin-4-yl)urea

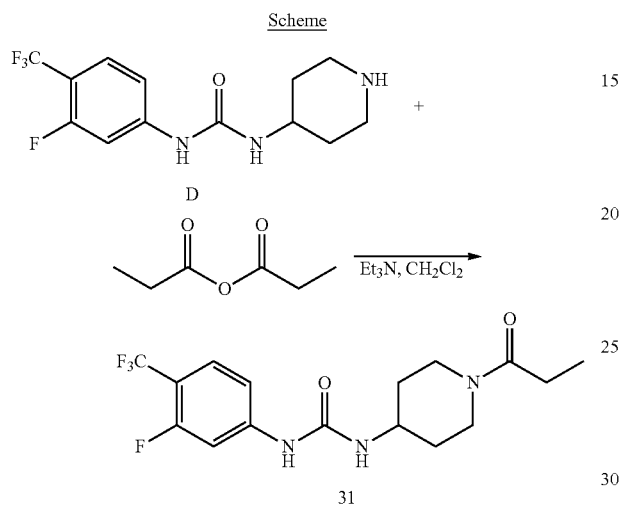

The reaction followed synthesis of inhibitor 23. Briefly, piperidine D (40 mg, 131.1 µmol) was reacted with propionic anhydride (25 mg, 192 µmol). The product was purified by flash chromatography and eluted by ethyl acetate. The collected fractions were dried in vacuo giving white solid.

Yield: 42 mg, 116 µmol, 88.7% yield. Purity (H-NMR): ≥95%

$^1$H NMR (d$_6$-DMSO, 300 Mhz): ∂ 9.50 (s, 1H), 7.65 (d, J=14.1 Hz, 1H), 7.56 (t, J=9 Hz, 1H), 7.19 (d, J=8.7 Hz, 1H), 6.85 (d, J=7.2 Hz, 1H), 4.14 (d, J=12.6 Hz, 1H), 3.6-3.8 (m, 2H), 3.11 (t, J=1.1, 1H), 2.79 (t, J=12.1 Hz, 1H), 2.2-2.4 (m, 2H), 1.79 (t, J=12.6 Hz, 2H), 1.1-1.4 (m, 2H), 0.96 (t, J=7.5 Hz, 3H)

Example 34

Synthesis of 1-(1-(cyclopropanecarbonyl)piperidin-4-yl)-3-(3-fluoro-4-(trifluoromethyl)phenyl)urea

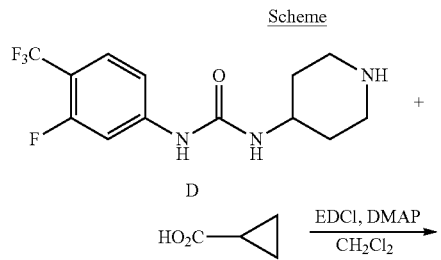

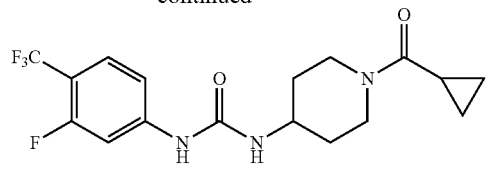

The reaction was carried out according to synthetic pathway 1, step 3. Piperidine D (40 mg, 131.1 µmol) was reacted with cyclopropanecarboxylic acid (17 mg, 197.4 µmol). The product was purified by flash chromatography and eluted by ethyl acetate:hexane (9:1). The collected fraction was dried in vacuo giving white solid.

Yield: 45 mg, 121 µmol, 91.9% yield. Purity (H-NMR): ≥95%

$^1$H NMR (d$_6$-DMSO, 300 Mhz): ∂ 9.03 (s, 1H), 7.65 (d, J=14.1 Hz, 1H), 7.56 (t, J=9 Hz, 1H), 7.19 (d, J=8.7 Hz, 1H), 6.47 (d, J=6.9 Hz, 1H), 4.16 (br, 2H), 3.6-3.8 (m, 1H), 3.2-3.3 (m, 1H), 2.7-2.9 (m, 1H), 1.7-2.0 (m, 3H), 1.1-1.4 (m, 2H), 0.6-0.8 (m, 4H)

Example 35

Synthesis of (R)-1-(3-fluoro-4-(trifluoromethyl)phenyl)-3-(1-(tetrahydrofuran-3-carbonyl)piperidin-4-yl)urea

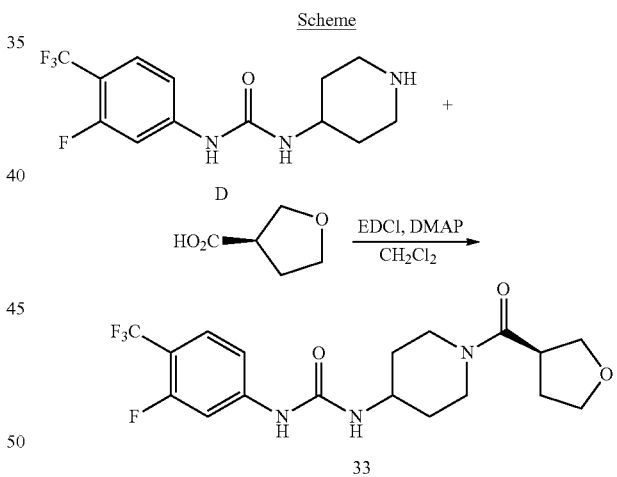

The reaction was carried out according to synthetic pathway 1, step 3. Piperidine D (40 mg, 131.1 µmol) was reacted with (R)-tetrahydrofuran-3-carboxylic acid (23 mg, 197.4 µmol). The product was purified by flash chromatography and eluted by ethyl acetate. The collected fraction was dried in vacuo giving white solid.

Yield: 41 mg, 102 µmol, 77.5% yield. Purity (H-NMR): ≥95%

$^1$H NMR (d$_6$-DMSO, 300 Mhz): ∂ 9.02 (s, 1H), 7.65 (d, J=14.7 Hz, 1H), 7.58 (t, J=9 Hz, 1H), 7.19 (d, J=8.7 Hz, 1H), 6.45 (d, J=6.9 Hz, 1H), 4.20 (d, J=13.2 Hz, 1H), 3.8-3.9 (m, 2H), 3.6-3.8 (m, 4H), 3.3-3.4 (m, 1H), 3.10 (t, J=14.7 Hz, 1H), 2.81 (t, J=12.1 Hz, 1H), 2.00 (q, J=7.5 Hz, 2H), 1.84 (t, J=13.5 Hz, 2H), 1.1-1.4 (m, 2H)

Example 36

Synthesis of (S)-1-(3-fluoro-4-(trifluoromethyl)phenyl)-3-(1-(2-methylbutanoyl)piperidin-4-yl)urea

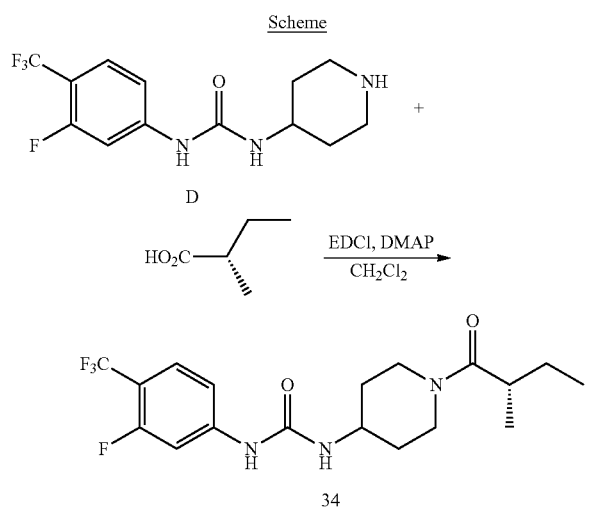

34

The reaction was carried out according to synthetic pathway 1, step 3. Piperidine D (40 mg, 131.1 μmol) was reacted with (S)-2-methylbutanoic acid (20 mg, 197.4 μmol). The product was purified by flash chromatography and eluted by ethyl acetate:hexane (4:1). The collected fraction was dried in vacuo giving white solid.

Yield: 36 mg, 92.4 μmol, 70.5% yield. Purity (H-NMR): ≥95%

$^1$H NMR (d$_6$-DMSO, 300 Mhz): ∂ 9.00 (d, J=4.5 Hz, 1H), 7.66 (d, J=14.1 Hz, 1H), 7.58 (t, J=9 Hz, 1H), 7.19 (d, J=8.7 Hz, 1H), 6.4-6.5 (m, 1H), 4.2-4.3 (br, 1H), 3.87 (d, J=12.9 Hz, 1H), 3.6-3.8 (m, 1H), 3.16 (t, J=12 Hz, 1H), 2.6-2.9 (m, 2H), 1.8-1.9 (m, 2H), 1.4-1.6 (m, 3H), 0.97 (s, 3H), 0.8-0.9 (m, 3H)

Example 37

Synthesis of 1-(3-fluoro-4-(trifluoromethyl)phenyl)-3-(1-(tetrahydro-2H-pyran-3-carbonyl)piperidin-4-yl)urea Scheme

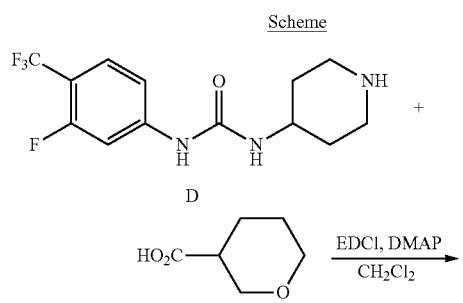

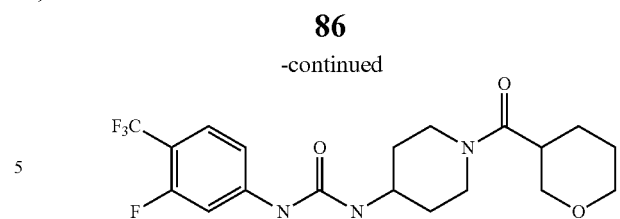

35

The reaction was carried out according to synthetic pathway 1, step 3. Piperidine D (40 mg, 131.1 μmol) was reacted with tetrahydro-2H-pyran-3-carboxylic acid (22.8 mg, 197.4 μmol). The product was purified by flash chromatography and eluted by ethyl acetate. The collected fraction was dried in vacuo giving white solid.

Yield: 41 mg, 98.2 μmol, 74.9% yield. Purity (H-NMR): ≥95%

$^1$H NMR (d$_6$-DMSO, 300 Mhz): ∂ 9.02 (s, 1H), 7.65 (d, J=14.7 Hz, 1H), 7.58 (t, J=8.4 Hz, 1H), 7.18 (d, J=9 Hz, 1H), 6.45 (d, J=6.9 Hz, 1H), 4.16 (d, J=13.5 Hz, 1H), 3.6-4.0 (m, 4H), 3.1-3.4 (m, 3H), 2.7-3.0 (m, 2H), 1.8-2.0 (m, 3H), 1.5-1.8 (s, 3H), 1.1-1.4 (m, 2H)

Example 38

Synthesis of 1-(3-fluoro-4-(trifluoromethyl)phenyl)-3-(1-(1-(trifluoromethyl)cycloproropane-1-carbonyl)piperidin-4-yl)urea Scheme

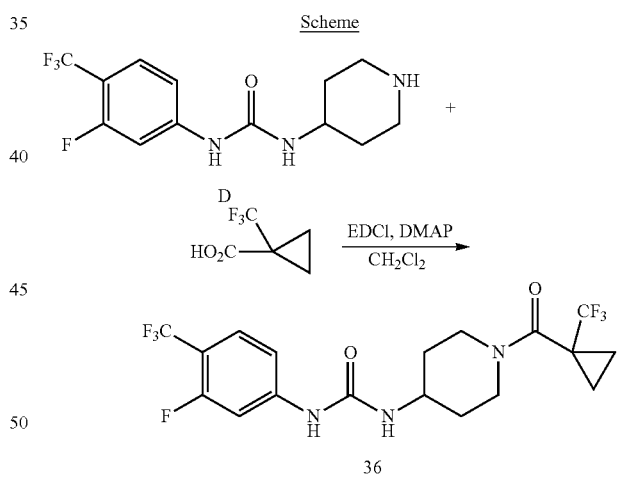

36

The reaction was carried out according to synthetic pathway 1, step 3. Piperidine D (40 mg, 131.1 μmol) was reacted with 1-(trifluoromethyl)cyclopropane-1-carboxylic acid (30 mg, 197.4 μmol). The product was purified by flash chromatography and eluted by ethyl acetate:hexane (9:1). The collected fraction was dried in vacuo giving white solid.

Yield: 46 mg, 104 μmol, 79.5% yield. Purity (H-NMR): ≥95%

$^1$H NMR (d$_6$-DMSO, 300 Mhz): ∂ 9.02 (s, 1H), 7.65 (d, J=14.1 Hz, 1H), 7.58 (t, J=9 Hz, 1H), 7.19 (d, J=8.7 Hz, 1H), 6.48 (d, J=7.2 Hz, 1H), 4.10 (d, J=12.3 Hz, 2H), 3.6-3.8 (m, 1H), 3.0-3.2 (br, 2H), 1.87 (d, J=9.9 Hz, 2H), 1.1-1.5 (m, 6H)

Example 39

Synthesis of 1-(3-fluoro-4-(trifluoromethyl)phenyl)-3-(1-(tetrahydro-2H-pyran-4-carbonyl)piperidin-4-yl)urea Scheme

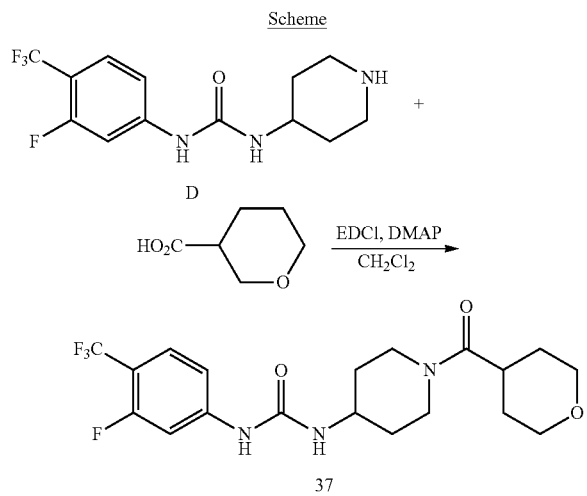

The reaction was carried out according to synthetic pathway 1, step 3. Piperidine D (40 mg, 131.1 μmol) was reacted with tetrahydro-2H-pyran-4-carboxylic acid (22.8 mg, 197.4 μmol). The product was purified by flash chromatography and eluted by ethyl acetate. The collected fraction was dried in vacuo giving white solid.

Yield: 46 mg, 108 μmol, 82.2% yield. Purity (H-NMR): ≥95%

$^1$H NMR (d$_6$-DMSO, 300 Mhz): ∂ 9.02 (s, 1H), 7.66 (d, J=14.1 Hz, 1H), 7.58 (t, J=8.4 Hz, 1H), 7.20 (d, J=8.7 Hz, 1H), 6.45 (d, J=7.5 Hz, 1H), 4.19 (d, J=12.3 Hz, 1H), 3.8-4.0 (m, 3H), 3.6-3.8 (m, 1H), 3.38 (t, J=11.4 Hz, 2H), 3.16 (t, J=12 Hz, 1H), 2.8-3.0 (m, 1H), 2.78 (t, J=11.7 Hz, 1H), 1.84 (t, J=15.3 Hz, 2H), 1.4-1.7 (m, 4H), 1.2-1.4 (m, 2H)

Example 40

Synthesis of 1-(3-fluoro-4-(trifluoromethoxy)phenyl)-3-(1-isobutyrylpiperidin-4-yl)urea Scheme

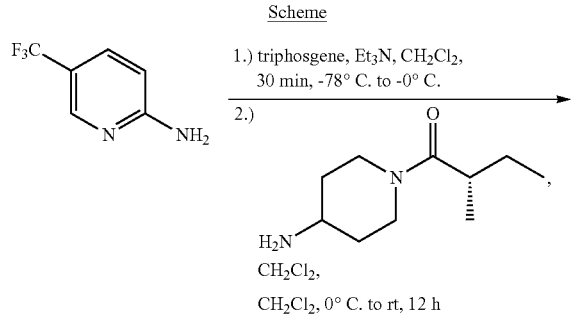

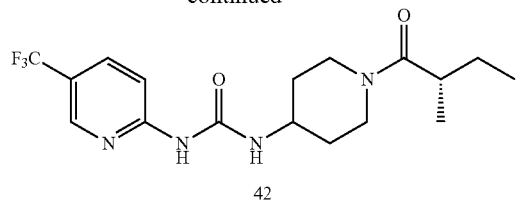

The reaction was carried out according to synthetic pathway 2. The 5-(trifluoromethyl)pyridine-2-aniline (100 mg, 617 μmol) was reacted with (S)-1-(4-aminopiperidin-1-yl)-2-methylbutan-1-one (174 mg, 944 μmol). The product was purified by flash chromatography using ethyl acetate. The product was further purified by recrystallization using methanol and water.

Yield: 153 mg, 411 μmol, 73.6% yield. Purity (H-NMR): ≥95%

$^1$H NMR (d$_6$-DMSO, 300 Mhz): ∂ 8.98 (d, J=7.5 Hz, 1H), 8.66 (s, 1H), 8.12 (d, J=8.7 Hz, 1H), 7.75 (d, J=11.7 Hz, 1H), 6.5-6.6 (m, 1H), 4.2-4.4 (br, 1H), 3.88 (d, J=13.5 Hz, 1H), 3.7-3.8 (m, 1H), 3.16 (t, J=10.8 Hz, 1H), 2.6-2.9 (m, 2H), 1.7-2.0 (m, 2H), 1.4-1.6 (m, 1H), 1.1-1.4 (m, 3H), 0.97 (s, 3H), 0.8-0.9 (m, 3H)

Example 41

Synthesis of 1-(3-fluoro-4-(trifluoromethoxy)phenyl)-3-(1-(morpholine-4-carbonyl)piperidin-4-yl)urea Scheme

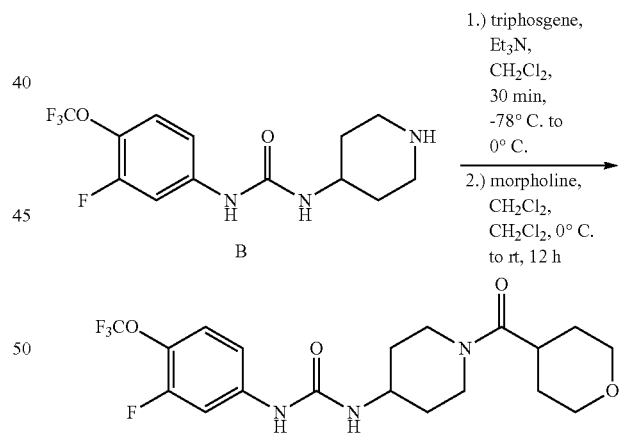

The reaction was carried out according to synthetic pathway 2. The piperidine B (40 mg, 124 μmol) was reacted with morpholine (12 mg, 138 μmol). The product was purified by flash chromatography using 1% methanol in ethyl acetate. The product was further purified by recrystallization using methanol and water.

Yield: 46 mg, 106 μmol, 85.4% yield. Purity (H-NMR): ≥95%

$^1$H NMR (d$_6$-DMSO, 300 Mhz): ∂ 8.77 (s, 1H), 7.66 (dd, J=13.5, 2.4 Hz, 1H), 7.39 (t, J=8.4 Hz, 1H), 7.10 (d, J=8.7 Hz, 1H), 6.33 (d, J=7.5 Hz, 1H), 3.6-3.7 (m, 1H), 3.4-3.6 (m,

5H), 3.11 (t, J=4.2 Hz, 3H), 2.87 (t, J=11.1 Hz, 1H), 1.79 (d, J=10.2 Hz, 2H), 1.2-1.4 (m, 2H)

Example 42

Synthesis of 2-(1-(cyclopropanecarbonyl)piperidin-4-yl)-N-(3-fluoro-4-(trifluoromethoxy)phenyl)acetamide

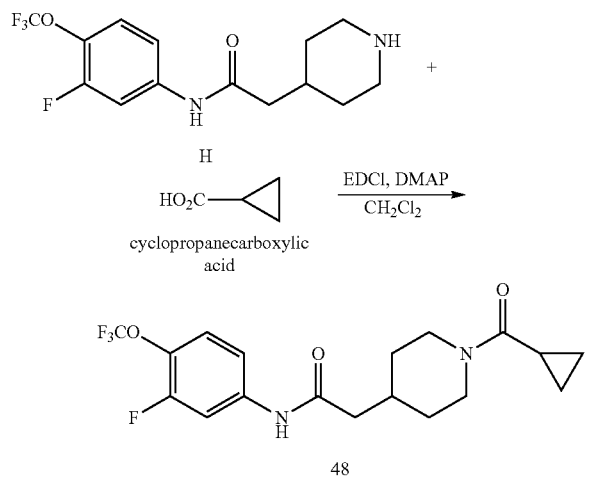

The reaction was carried out according to synthetic pathway 1, step 3. Piperidine H (38 mg, 118 μmol) was reacted with cyclopropanecarboxylic acid (12.3 mg, 142.9 μmol). The product was purified by flash chromatography and eluted by ethyl acetate. The collected fraction was dried in vacuo giving white solid.

Yield: 32 mg, 82.4 μmol, 69.8% yield. Purity (H-NMR): ≥95%

$^1$H NMR (d$_6$-DMSO, 300 Mhz): ∂ 10.29 (s, 1H), 7.85 (dd, J=12.9, 2.1 Hz, 1H), 7.50 (t, J=9 Hz, 1H), 7.35 (d, J=8.7 Hz, 1H), 4.2-4.4 (m, 2H), 3.0-3.2 (m, 1H), 2.57 (t, J=12 Hz, 1H), 2.28 (d, J=6.9 Hz, 2H), 1.9-2.1 (m, 2H), 1.6-1.8 (m, 2H), 1.0-1.2 (m, 2H), 0.69 (m, 4H)

Example 43

Synthesis of ((S)—N-(3-fluoro-4-(trifluoromethoxy)phenyl)-2-(1-(2-methylbutanoyl)piperidin-4-yl)acetamide

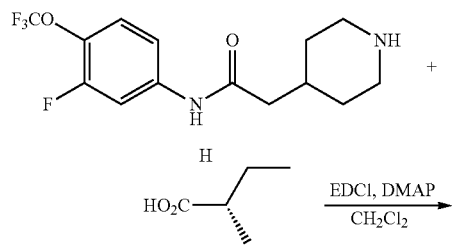

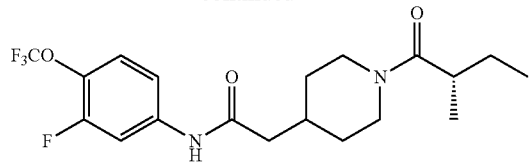

The reaction was carried out according to synthetic pathway 1, step 3. Piperidine H (38 mg, 118 μmol) was reacted with (S)-2-methylbutanoic acid (14 mg, 142.9 μmol). The product was purified by flash chromatography and eluted by ethyl acetate). The collected fraction was dried in vacuo giving white solid (27 mg, 66.8 μmol, 56.6% yield).

Yield: 27 mg, 66.8 μmol, 56.6% yield. Purity (H-NMR): ≥95%

$^1$H NMR (d$_6$-DMSO, 300 Mhz): ∂ 10.28 (s, 1H), 7.84 (dd, J=12.6, 2.4 Hz, 1H), 7.50 (t, J=9 Hz, 1H), 7.36 (d, J=9 Hz, 1H), 4.39 (d, J=12.3 Hz, 1H), 3.95 (d, J=12.6 Hz, 1H), 3.00 (t, J=12.3 Hz, 1H), 2.6-2.8 (m, 1H), 2.27 (d, J=6.9 Hz, 2H), 1.9-2.1 (m, 1H), 1.6-1.8 (m, 2H), 1.5-1.6 (m, 1H), 1.2-1.4 (m, 1H), 1.0-1.2 (m, 2H), 0.96 (t, J=6 Hz, 3H), 0.7-0.9 (m, 3H)

Example 44

Synthesis of N-(3-fluoro-4-(trifluoromethoxy)phenyl)-2-(1-isobutyrylpiperidin-4-yl)acetamide

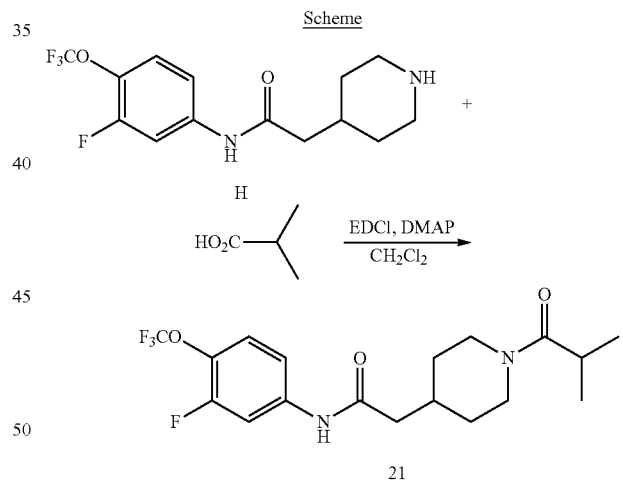

The reaction was carried out according to synthetic pathway 1, step 3. Piperidine H (38 mg, 118 μmol) was reacted with isobutyric acid (12.6 mg, 142.9 μmol). The product was purified by flash chromatography and eluted by ethyl acetate). The collected fraction was dried in vacuo giving white solid.

Yield: 30 mg, 76.8 μmol, 65.1% yield. Purity (H-NMR): ≥95%

$^1$H NMR (d$_6$-DMSO, 300 Mhz): ∂ 10.28 (s, 1H), 7.84 (dd, J=12.9, 1.8 Hz, 1H), 7.49 (t, J=9 Hz, 1H), 7.36 (d, J=9.6 Hz, 1H), 4.36 (d, J=12.6 Hz, 1H), 3.91 (d, J=12.9 Hz, 1H), 3.00 (t, J=11.7 Hz, 1H), 2.8-2.9 (m, 1H), 2.5-2.6 (m, 1H), 2.27 (d, J=6.9 Hz, 2H), 1.9-2.1 (m, 1H), 1.70 (t, J=13.5 Hz, 2H), 0.9-1.2 (m, 8H).

Example 45

Synthesis of (S)-1-(3-chloro-4-(trifluoromethoxy)phenyl)-3-(1-(2-methylbutanoyl)piperidin-4-yl)urea

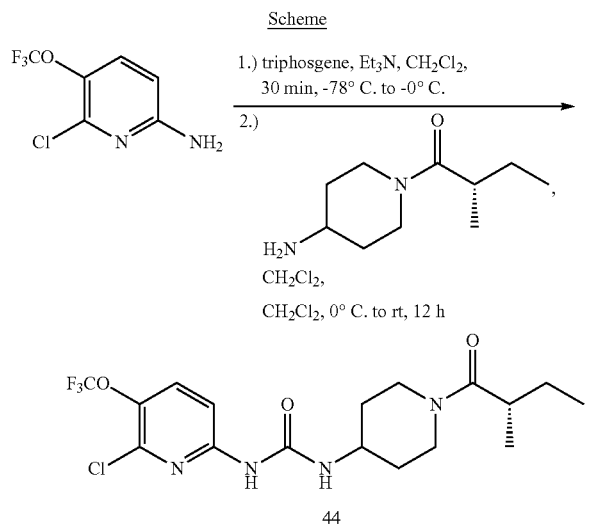

44

The reaction was carried out according to synthetic pathway 2. The 3-chloro-4-(trifluoromethoxy)aniline (50 mg, 236 μmol) was reacted with (S)-1-(4-aminopiperidin-1-yl)-2-methylbutan-1-one (65 mg, 353 μmol). The product was purified by flash chromatography using ethyl acetate. The product was further purified by recrystallization using methanol and water.

Yield: 78 mg, 185 μmol, 78.4% yield. Purity (H-NMR): ≥95%

$^1$H NMR (d$_6$-DMSO, 300 Mhz): ∂ 8.98 (d, J=4.5 Hz, 1H), 8.65 (s, 1H), 8.13 (d, J=8.7 Hz, 1H), 6.4-6.6 (m, 1H), 4.2-4.3 (br, 1H), 3.88 (d, J=13.5 Hz, 1H), 3.6-3.8 (m, 1H), 3.13 (t, J=12 Hz, 1H), 2.6-2.9 (m, 2H), 1.8-1.9 (m, 2H), 1.4-1.6 (m, 1H), 1.2-1.4 (m, 3H), 0.97 (s, 3H), 0.8-0.9 (m, 3H)

Example 46

Synthesis of (S)-1-(3-chloro-4-(trifluoromethoxy)phenyl)-3-(1-(2-methylbutanoyl)piperidin-4-yl)urea

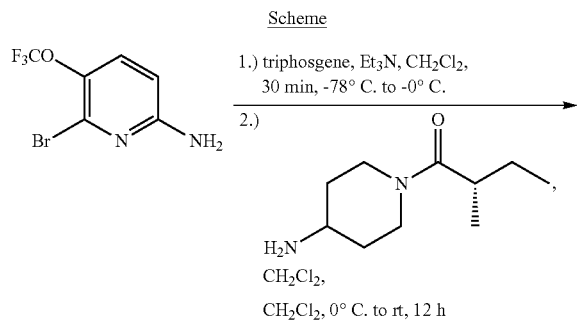

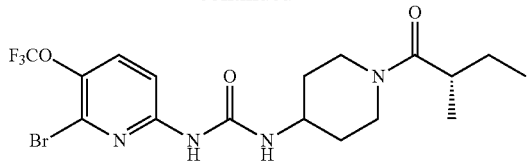 [SMILES: CC[C@H](C)C(=O)N1CCC(NC(=O)Nc2ccc(OC(F)(F)F)c(Br)c2)CC1]

45

The reaction was carried out according to synthetic pathway 2. The 3-bromo-4-(trifluoromethoxy)aniline (55 mg, 234 μmol) was reacted with (S)-1-(4-aminopiperidin-1-yl)-2-methylbutan-1-one (65 mg, 353 μmol). The product was purified by flash chromatography using ethyl acetate. The collected fractions were combined and dried in vacuo.

Yield: 81 mg, 174 μmol, 74.4% yield. Purity (H-NMR): ≥95%

$^1$H NMR (d$_6$-DMSO, 300 Mhz): ∂ 8.70 (d, J=4.5 Hz, 1H), 7.97 (d, J=1.8 Hz, 1H), 7.3-7.4 (m, 2H), 6.4-6.6 (m, 1H), 4.2-4.3 (br, 1H), 3.88 (d, J=11.7 Hz, 1H), 3.6-3.8 (m, 1H), 3.15 (t, J=12.9 Hz, 1H), 2.6-2.9 (m, 2H), 1.7-1.9 (m, 2H), 1.4-1.6 (m, 1H), 1.2-1.4 (m, 3H), 0.97 (s, 3H), 0.8-0.9 (m, 3H)

Example 47

Synthesis of (S)-1-(1-(2-methylbutanoyl)piperidin-4-yl)-3-(4-(trifluoromethoxy)-3-(trifluoromethyl)phenyl)urea

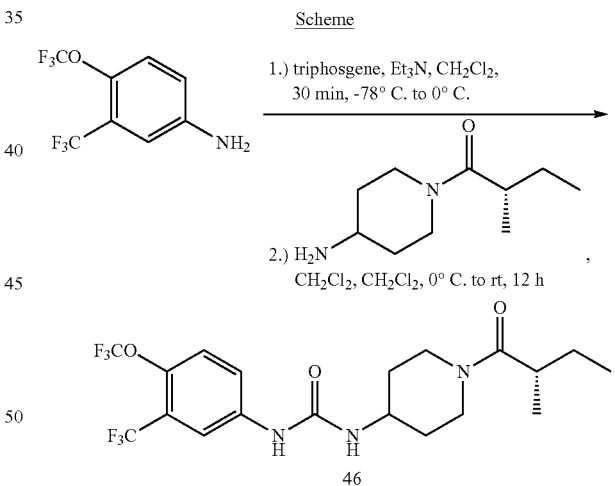

46

The reaction was carried out according to synthetic pathway 2. The 4-(trifluoromethoxy)-3-(trifluoromethyl)aniline (55 mg, 224 μmol) was reacted with (S)-1-(4-aminopiperidin-1-yl)-2-methylbutan-1-one (64 mg, 347 μmol). The product was purified by flash chromatography using ethyl acetate. The product was further purified by recrystallization using methanol and water.

Yield: 73 mg, 160 μmol, 71.6% yield. Purity (H-NMR): ≥95%

$^1$H NMR (d$_6$-DMSO, 300 Mhz): ∂ 8.89 (d, J=8.4 Hz, 1H), 8.06 (d, J=2.4 Hz, 1H), 7.63 (dd, J=9.6, 2.4 Hz, 1H), 7.51 (d, J=11.7 Hz, 1H), 6.42 (t, J=7.2 Hz, 1H), 4.2-4.3 (br, 1H), 3.88 (d, J=13.5 Hz, 1H), 3.6-3.8 (m, 1H), 3.15 (t, J=12.9 Hz, 1H), 2.6-2.8 (m, 2H), 1.7-1.9 (m, 2H), 1.4-1.6 (m, 1H), 1.2-1.4 (m, 3H), 0.9-1.1 (m, 3H), 0.8-0.9 (m, 3H)

Example 48

Synthesis of (S)-1-(1-(2-methylbutanoyl)piperidin-4-yl)-3-(4-(trifluoromethoxy)-3-(trifluoromethyl)phenyl)urea

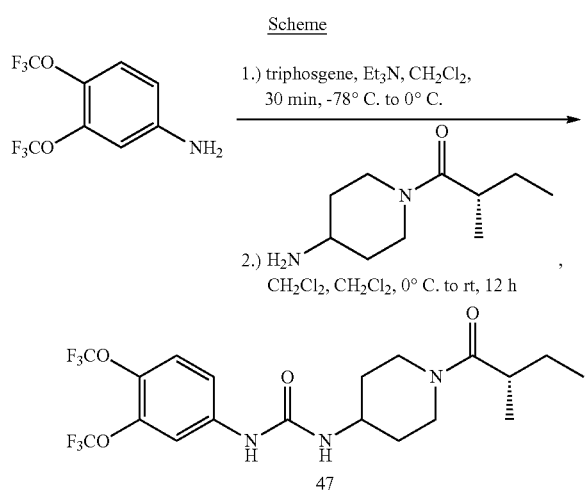

The reaction was carried out according to synthetic pathway 2. The 3,4-bis(trifluoromethoxy)aniline (60 mg, 230 µmol) was reacted with (S)-1-(4-aminopiperidin-1-yl)-2-methylbutan-1-one (64 mg, 347 µmol). The product was purified by flash chromatography using ethyl acetate. The product was further purified by recrystallization using methanol and water (68 mg, 144 µmol, 62.7% yield).

Yield: 68 mg, 144 µmol, 62.7% yield. Purity (H-NMR): ≥95%

$^1$H NMR (d$_6$-DMSO, 300 Mhz): ∂ 8.86 (d, J=7.5 Hz, 1H), 7.91 (s, 1H), 7.47 (d, J=11.7 Hz, 1H), 7.28 (dd, J=8.7, 2.4 Hz, 1H), 6.39 (t, J=7.8 Hz, 1H), 4.2-4.3 (br, 1H), 3.88 (d, J=12.3 Hz, 1H), 3.6-3.8 (m, 1H), 3.15 (t, J=11.4 Hz, 1H), 2.6-2.8 (m, 2H), 1.7-1.9 (m, 2H), 1.4-1.6 (m, 1H), 1.2-1.4 (m, 3H), 0.97 (s, 3H), 0.8-0.9 (m, 3H)

Example 49

Synthesis of ethyl 4-(3-(3-fluoro-4-(trifluoromethoxy)phenyl)ureido)piperidine-1-carboxylate

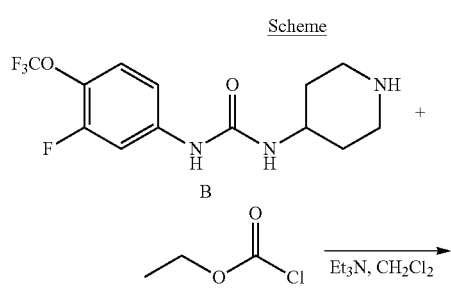

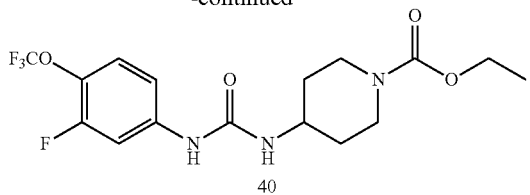

To the suspension of piperidine B (30 mg, 93.5 µmol) and triethylamine (11.6 mg, 115 µmol), ethyl chloroformate (29.6 mg, 274 µmol) was added dropwise. The reaction was stirred at rt for 12 h and was quenched by addition of silica gel (50 mg). The slurry was dried in vacuo and was applied to flash chromatography. The product was eluted by ethyl acetate:hexane (4:1) and monitored by TLC. The collected fractions were dried in vacuo to give the final white powder.

Yield: 87.1% (32 mg, 81.4 µmol) Purity: ≥95% (H-NMR)

$^1$H NMR (d$_6$-DMSO, 600 Mhz): ∂ 8.78 (s, 1H), 7.66 (dd, J=14.1, 2.4 Hz, 1H), 7.38 (t, J=9 Hz, 1H), 7.09 (d, J=12 Hz, 1H), 6.34 (d, J=9 Hz, 1H), 4.02 (q, J=6.9 Hz, 2H), 3.85 (d, J=13.5 Hz, 2H), 3.6-3.8 (m, 1H), 2.8-3.0 (m, 2H), 1.79 (t, J=10.2 Hz, 2H), 1.2-1.4 (m, 2H), 1.18 (t, J=7.2 Hz, 3H)

Example 50

Synthesis of ethyl 4-(3-(3-fluoro-4-(trifluoromethyl)phenyl) ureido)piperidine-1-carboxylate

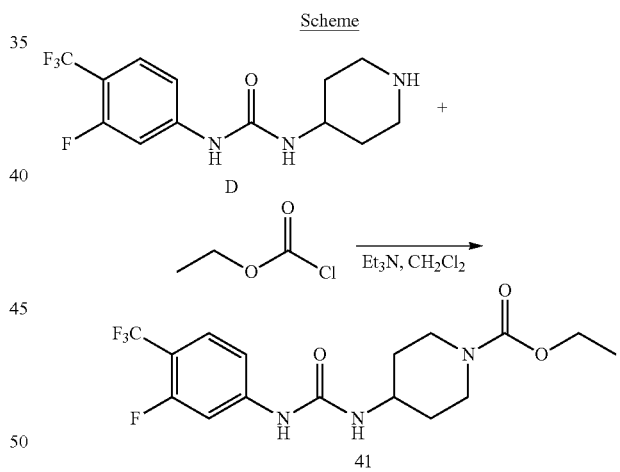

To the suspension of piperidine D (30 mg, 97 µmol) and triethylamine (13.1 mg, 129 µmol), ethyl chloroformate (31.9 mg, 294 µmol) was added dropwise. The reaction was stirred at rt for 12 h and was quenched by addition of silica gel (50 mg). The slurry was dried in vacuo and was applied to flash chromatography. The product was eluted by ethyl acetate:hexane (4:1) and monitored by TLC. The collected fractions were dried in vacuo to give the final white powder.

Yield: 90.2% (33 mg, 87.5 µmol) Purity: ≥95% (H-NMR)

$^1$H NMR (d$_6$-DMSO, 600 Mhz): ∂ 9.02 (s, 1H), 7.65 (d, J=14.1 Hz, 1H), 7.58 (t, J=8.7 Hz, 1H), 7.19 (d, J=9 Hz, 1H), 6.45 (d, J=7.5 Hz, 1H), 4.02 (q, J=6.9 Hz, 2H), 3.85 (d, J=13.5 Hz, 2H), 3.6-3.8 (m, 1H), 2.8-3.0 (m, 2H), 1.80 (dd, J=12.6, 3.3 Hz, 2H), 1.2-1.4 (m, 2H), 1.18 (t, J=7.2 Hz, 3H)

Example 51

Synthesis of 1-(3-fluoro-4-(trifluoromethoxy)phenyl)-3-(1-(2-methylbutanoyl)piperidin-4-yl)urea

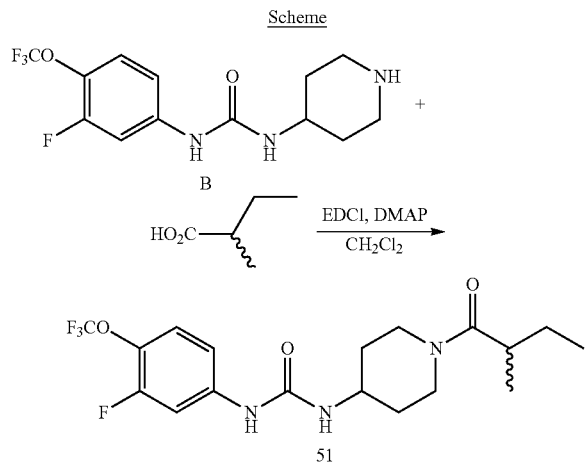

Scheme

The reaction was carried out according to synthetic pathway 1, step 3. Piperidine B (52 mg, 161.8 µmol) was reacted with (S)-2-methylbutanoic acid (24 mg, 243 µmol). The product was purified by flash chromatography and eluted by ethyl acetate. The collected fraction was dried in vacuo giving white solid. The product was further purified by recrystallization using ethyl acetate and hexane.

Yield: 52 mg, 145 µmol, 89.9% yield. Purity (H-NMR): ≥95%

$^1$H NMR ($d_6$-DMSO, 300 Mhz): ∂ 8.75 (d, J=6.9 Hz, 1H), 7.67 (dd, J=13.5 Hz, 2.4 Hz, 1H), 7.39 (t, J=9.3 Hz, 1H), 7.11 (d, J=8.7 Hz, 1H), 6.3-6.4 (m, 1H), 4.23 (m, 1H), 3.88 (d, J=10.8 Hz, 1H), 3.6-3.8 (m, 1H), 3.1-3.2 (m, 1H), 2.6-2.8 (m, 2H), 1.7-1.9 (m, 2H), 1.5-1.6 (m, 1H), 1.1-1.4 (m, 3H), 0.9-1.0 (m, 3H), 0.7-0.9 (m, 3H)

Example 52

Seizure Assay

Pentylenetetrazol (PTZ) Induced Seizure Model

To investigate the central nervous system penetration efficacy of sEH inhibitors a standard acute test involving the administration of pro-convulsant pentylenetetrazol (PTZ) was employed. In the subcutaneous pentylenetetrazol (PTZ) test 80 mg/kg of PTZ is administered by subcutaneous route, time to onset of first clonic seizure (clonus), time to tonic hind limb extension and lethality (tonus) are monitored for a duration of 30 min. Inhibitors of sEH were completely dissolved using PEG400 as a vehicle to give clear solutions. Inhibitors or vehicle were administered by intraperitoneal route 1 h prior to pro-convulsant at a single discriminating dose based on earlier data. This dose of PTZ produces 100% lethality within 30 min upon administration.

Figure 8:
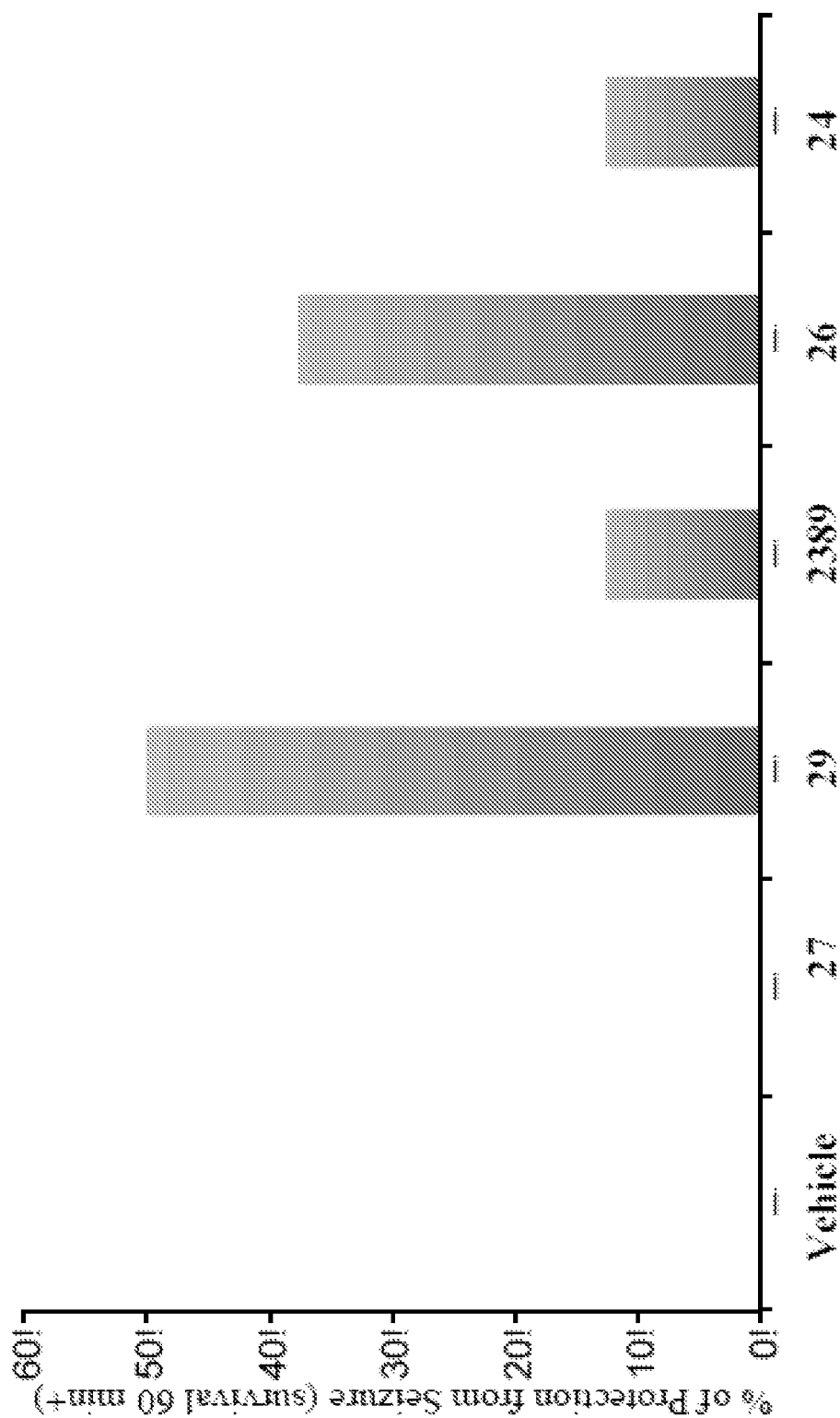
FIG. 8 is a graph showing the CNS protective effects from sEH inhibitors. Several sEH inhibitors protected mice from dying from PTZ induced seizure.

Compound 29 was found to protect mice from convulsions and associated lethality demonstrating that compounds claimed herein can cross blood-brain barrier (FIG. 7). PTZ is a chemical which induces seizures. This assay is considered highly translatable from mice to humans. In this seizure assay, which is completely dependent on the ability of compounds to cross the blood brain barrier, Compound 29 displayed significant efficacy suggesting that this compound readily penetrates the CNS and protect the mice from seizure (FIGS. 7 and 8).

Example 53

FRET-Displacement Assay Procedure

FRET assays to determine $K_i$ for the compounds of Table I were carried out as described previously (Lee et al. *Analytical Biochemistry* 434 (2013) 259-268). In order to prevent leaching of fluorescence impurities from the plastic tube and non-specific binding to sEH inhibitors, the inhibitor stock solution (10 mM, DMSO) was stored in glass vials. In addition, sEH was diluted to desired concentration (20 nM) with sodium phosphate buffer (PB) (100 mM sodium phosphate, pH 7.4, 0.01% gelatin) to avoid loss of protein from non-specific binding to the cuvette surface. All buffer used in this assay was filtered by sterilized filtration unit (Millipore® Durapore PVDF Membrane, pore size: 0.22 um).

Measurement in 96-Well Plates

All the measurement for FRET-based displacement assay in 96-well plate format were done in TECAN Infinite® M1000 Pro 96 well fluorescence plate reader.

Pre-Treatment of 96-Well Plate

In order to prevent non-specific binding of sEH or inhibitor on the 96-well plate, the 96 well plates were pre-incubated with PB with 0.1% gelatin overnight at rt. The gelatin coats the plate and prevents non-specific binding of sEH and sEH inhibitors to the plate. The buffer was discarded and the plate was dried before use.

Assay Procedure

The sEH stock was diluted to the desired concentration (20 nM) by PB (100 mM sodium phosphate, 0.1% gelatin, pH 7.4). ACPU (one equivalent to sEH, 10 mM, Ethanol) was added to the sEH solution and was incubated for 2 h at rt. The sEH-ACPU mixture (20 nM, 100 mM sodium phosphate, 0.1% gelatin, pH 7.4, 150 uL) was added to each well.

The baseline fluorescence ($F_0$) ($\lambda_{excitation}$ at 280 nm, $\lambda_{emission}$ at 450 nm) of the samples was measured after the z-position and gain were optimized automatically by the fluorometers. The z and gain value was noted and will be used for the later fluorescent measurement. Because DMSO has been known to quench fluorescence. 1% DMSO in PB was served as a control ($F_{DMSO}$). The desired concentration of inhibitors which is the concentration that 100% of sEH was bound to inhibitor, was added at the first well and was further diluted by 2-fold across the rest of the wells. Based on our study, 12 datum points which correspond to 12 different concentrations of the inhibitor, provide significant data to calculate the accurate $K_i$ for the inhibitors. The samples were incubated at 30° C. for 1.5 h. Then, the fluorescence ($\lambda_{excitation}$ at 280 nm, $\lambda_{emission}$ at 450 nm) of the samples was measured using the z-position and gain values that previously obtained. The obtained fluorescence signals were transformed as below and were used to calculated the $K_i$ of the inhibitors according to "Curve fitting" section below.

Initiated fluorescence=$F_{DMSO(well\ X)}/F_{0\ (well\ X)}$

Saturated fluorescence=
$F_{at\ the\ saturated\ concentration\ (well\ X)}/F_{0\ (at\ well\ X)}$ Observed fluorescence=$F_{(well\ X)}/F_{0\ (well\ X)}$ Curve Fitting The curve fitting for $K_i$ determination was reported before (Lee et al). The data manipulation and $K_i$ calculation were based on the original paper by Wang (*Febs Letters* 360 (1995) 111-114) with modifications suggested by Roehrl et al (*PNAS* 101 (2004) 7554-7559).

The displacement assay is based on a three-state equilibrium binding model. This is modeled as described below (Eq. 1)

$$[RI]+L \Leftrightarrow R+I+L \Leftrightarrow [RL]+I \quad \text{(Eq. 1)}$$

with [RI] stands for receptor or enzyme-inhibitor complex;

L stands for reporting ligand;

I stands for inhibitors;

[RL] stands for receptor or enzyme-reporting ligand complex.

The three-state equilibrium (Eq. 1) consists of the sEH-inhibitor complex, sEH and sEH-reporting ligand complex. In this study, the relative fluorescence intensity ($F_3$) was plotted against the concentration of sEH inhibitor and the resulting curve was fitted into equation (Eq. 2) derived by Wang for three-state equilibrium.

$$F_3=[2(a^2-3b)^{1/2}\cos(\theta/3)-a]/\{3K_{d1}+[2(a^2-3b)^{1/2}\cos(\theta/3)-a] \quad \text{(Eq. 2)}$$

with $a=K_{d1}+K_{d2}+L+I-R$;

$b=K_{d2}(L-R)+K_{d1}(I-R)+K_{d1}K_{d2}$;

$c=-K_{d1}K_{d2}R$; and $\theta=\arccos\{(-2a^2+9ab-27c)/[2(a^{2\,ab})^{3/2}]\}$.

where $F_3$=Relative Fluorescence=(observed fluorescence–fluorescence at saturation)/(initiated fluorescence–fluorescence at saturation)

I=the concentration of added unlabeled competing ligand;

R=the total concentration of sEH;

L=The total concentration of reporting ligand;

$K_{d1}$=The dissociation constant of reporting ligand (found by fluorescent binding assay), and;

$K_{d2}$=The inhibition constant of inhibitors $k_{off}$ Measurement Procedure

The $k_{off}$ measurement was run as described before.[10] The sEH (8 μM) was pre-incubated with the selected inhibitor (8.8 μM, 100 mM PB buffer, pH 7.4) for 1.5 h at rt. The sEH-inhibitor complex was then diluted 40 times with ACPU (20 μM, 100 mM Sodium phosphate buffer, pH 7.4). The fluorescence ($\lambda_{excitation}$ at 280 nm, $\lambda_{emission}$ at 450 nm) was monitored immediately for every 30 s up to 5100 s. The fluorescence ($\lambda_{emission}$ at 450 nm) data was plotted against time (s). The resulting curve was fitted to single exponential growth and the relative $k_{off}$ was obtained.

Example 54

Nociceptive Assay

Rate Model of Nociceptive Assay of Diabetic Rat

Male Sprague-Dawley rats weighing 250-300 grams were used. Animals were individually housed under standard conditions with free access to food and water, and maintained for at least 1 week before the experiments. Pain was quantified using the von Frey mechanical allodynia test. All the experiments were performed during the daylight photoperiod at the same time of the day.

Rats were first trained to the experimental chamber in two separate sessions. On the day of the induction of neuropathy, the animals' basal response to tests were measured and then streptozocin (55 mg/kg) was administered intravenously to induce a diabetic state. Animals were then followed over time for the development of neuropathic pain which occurs in 7-10 days. Test compounds were then administered subcutaneously approximately one week after the onset of pain symptoms. Pain response was measured over a period of several hours as indicated in the FIG. legends. Compounds were formulated by dissolving them in a carrier to result in amounts that are indicated in FIG. legends. At least six animals per group were used, although for some experiments twelve rats were used. The von Frey test was conducted by stimulating the plantar surface of the rats' hind paw with a calibrated filament connected to a force transducer (IITC Inc, Woodland Hills Calif.). As this filament is applied the amount of force exerted on the paw increases and the animal withdraws its paw when the force reaches its threshold. The force this moment is displayed electronically with a display connected to the force transducer.

In nociceptive assays using type I diabetic rats, the compounds of the present disclosure outperformed a standard drug registered for neuropathic pain, gabapentin and a standard sEH inhibitor APAU. The compounds of the present disclosure reached high levels of efficacy more rapidly. Moreover, the compounds of the present disclosure displayed higher potency and also higher efficacy compared to standards in the field (FIG. 6).

Although the invention has been described with reference to the above example, it will be understood that modifications and variations are encompassed within the spirit and scope of the invention. Accordingly, the invention is limited only by the following claims.

What is claimed is:

1. A compound, wherein the compound is (S)-1-(3-fluoro-4-(trifluoromethoxy)phenyl)-3-(1-(2-methylbutanoyl)piperidin-4-yl)urea (Compound 26)

or pharmaceutically acceptable salt thereof.

2. A compound having the structure:

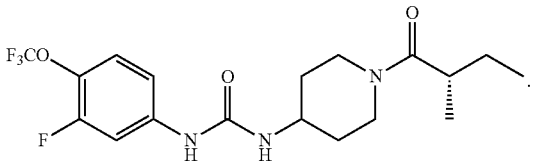 [SMILES: CC[C@H](C)C(=O)N1CCC(NC(=O)Nc2ccc(OC(F)(F)F)c(F)c2)CC1]

* * * * *